US010077315B2

(12) United States Patent
Vu et al.

(10) Patent No.: US 10,077,315 B2
(45) Date of Patent: Sep. 18, 2018

(54) BISPECIFIC ANTIBODIES AGAINST CD3 AND BCMA

(71) Applicant: ENGMAB AG, Wilen (CH)

(72) Inventors: Minh Diem Vu, Wollerau (CH); Klaus Strein, Weinheim (DE); Ekkehard Moessner, Kreuzlingen (CH); Ralf Hosse, Cham (CH); Oliver Ast, Bassersdorf (CH); Anne Freimoser-Grundschober, Zürich (CH); Marina Bacac, Zürich (CH); Tanja Fauti, Zürich (CH); Christian Klein, Bonstetten (CH); Pablo Umana, Wollerau (CH); Samuel Moser, Rotkreuz (CH)

(73) Assignee: ENGMAB SÀRL, Boudry (CH)

( * ) Notice: Subject to any disclaimer, the term of this patent is extended or adjusted under 35 U.S.C. 154(b) by 67 days.

(21) Appl. No.: 14/764,968

(22) PCT Filed: Feb. 5, 2014

(86) PCT No.: PCT/EP2014/052190
§ 371 (c)(1),
(2) Date: Jul. 30, 2015

(87) PCT Pub. No.: WO2014/122144
PCT Pub. Date: Aug. 14, 2014

(65) Prior Publication Data
US 2015/0376287 A1    Dec. 31, 2015

(30) Foreign Application Priority Data

Feb. 5, 2013 (EP) .................................... 13000570
Feb. 5, 2013 (EP) .................................... 13000571

(51) Int. Cl.
| | | |
|---|---|---|
| *A61K 39/395* | (2006.01) | |
| *C07K 16/28* | (2006.01) | |
| *C12N 5/10* | (2006.01) | |
| *C12N 15/63* | (2006.01) | |
| *C07K 16/30* | (2006.01) | |
| *G01N 33/68* | (2006.01) | |
| *C07K 14/705* | (2006.01) | |
| *C07K 14/715* | (2006.01) | |
| *C12N 5/07* | (2010.01) | |
| *A61K 39/00* | (2006.01) | |

(52) U.S. Cl.
CPC ........ *C07K 16/2878* (2013.01); *A61K 39/395* (2013.01); *A61K 39/3955* (2013.01); *C07K 16/2809* (2013.01); *C07K 16/3061* (2013.01); *G01N 33/6863* (2013.01); *A61K 2039/505* (2013.01); *C07K 16/28* (2013.01); *C07K 16/2863* (2013.01); *C07K 2317/31* (2013.01); *C07K 2317/56* (2013.01); *C07K 2317/565* (2013.01); *C07K 2317/66* (2013.01); *C07K 2317/71* (2013.01); *C07K 2317/732* (2013.01); *C07K 2317/76* (2013.01); *C07K 2317/92* (2013.01); *C12N 5/06* (2013.01); *C12N 15/63* (2013.01); *G01N 2333/7151* (2013.01); *G01N 2500/04* (2013.01)

(58) Field of Classification Search
CPC .......... A61K 2039/505; A61K 39/3955; A61K 39/39558; A61K 39/395; A61K 38/177; C07K 2317/76; C07K 2317/92; C07K 2317/56; C07K 2317/565; C07K 16/2878; C07K 2317/73; C07K 2317/55; C07K 2317/52; C07K 2317/94; C07K 16/18; C07K 16/2866; C07K 16/2896; C07K 16/28
See application file for complete search history.

(56) References Cited

U.S. PATENT DOCUMENTS

| | | | |
|---|---|---|---|
| 4,816,567 | A | 3/1989 | Cabilly et al. |
| 5,624,821 | A | 4/1997 | Winter et al. |
| 5,837,242 | A | 11/1998 | Holliger et al. |
| 6,194,551 | B1 | 2/2001 | Idusogie et al. |
| 6,602,684 | B1 | 8/2003 | Umana et al. |
| 7,064,191 | B2 | 6/2006 | Shinkawa et al. |
| 7,214,775 | B2 | 5/2007 | Hanai et al. |
| 7,504,256 | B1 | 3/2009 | Ogawa et al. |

(Continued)

FOREIGN PATENT DOCUMENTS

| | | |
|---|---|---|
| CA | 2785941 A1 | 4/2002 |
| EP | 0307434 B2 | 7/1998 |
| EP | 0623679 B1 | 6/2003 |

(Continued)

OTHER PUBLICATIONS

Co-pending U.S. Appl. No. 14/764,967, inventors Vu, M.D., et al., I.A. filed Feb. 5, 2014 (Not Published).
Hristodorov, D., et al., "With or Without Sugar? (A)glycosylation of Therapeutic Antibodies," Molecular Biotechnology 54(3):1056-1068, Humana Press, United States (2013).
Laabi, Y., et al., "A New Gene, BCM, on Chromosome 16 is Fused to the Interleukin 2 Gene by a t(4;16)(q26;p13) Translocation in a Malignant T Cell Lymphoma," The EMBO Journal 11(11):3897-3904, Wiley Blackwell, England (1992).
Madry, C., et al., "The Characterization of Murine BCMA Gene Defines It as a New Member of the Tumor Necrosis Factor Receptor Superfamily," International Immunology 10(11):1693-1702, Oxford University Press, England (1998).
Rickert, R.C., et al., "Signaling by the Tumor Necrosis Factor Receptor Superfamily in B-Cell Biology and Disease," Immunological Reviews 244(1):115-133, Blackwell, England (2011).
Gras, M.P., et al, "BCMAp: An Integral Membrane Protein in the Golgi apparatus of Human Mature B Lymphocytes," International Immunology 7(7):1093-1106, Oxford University Press, England (1995).

(Continued)

*Primary Examiner* — Bridget E Bunner
(74) *Attorney, Agent, or Firm* — Eckert Seamans Cherin & Mellott LLC

(57) ABSTRACT

A bispecific antibody specifically binding to the two targets human CD3ε and human BCMA, wherein the variable domains of one antibody portion are replaced by each other, and characterized in that the binding of said antibody is not reduced by APRIL and not reduced by BAFF, said antibody does not alter APRIL-dependent NF-κB activation, BAFF-dependent NF-κB activation, and does not alter NF-κB activation without BAFF and APRIL is useful as a therapeutic agent.

5 Claims, 7 Drawing Sheets

Specification includes a Sequence Listing.

(56) References Cited

U.S. PATENT DOCUMENTS

| | | | |
|---|---|---|---|
| 2012/0008266 A1 | 4/2012 | Kalled et al. | |
| 2013/0156769 A1* | 6/2013 | Kufer | C07K 16/2809 424/136.1 |

FOREIGN PATENT DOCUMENTS

| | | |
|---|---|---|
| WO | WO/1996/027011 A1 | 9/1996 |
| WO | WO/1999/012964 A2 | 3/1999 |
| WO | WO/1999/054342 A1 | 10/1999 |
| WO | WO/1999/058572 A1 | 11/1999 |
| WO | WO/2000/040716 A2 | 7/2000 |
| WO | WO/2000/042072 A2 | 7/2000 |
| WO | WO/2000/061739 A1 | 10/2000 |
| WO | WO/2001/024811 A1 | 4/2001 |
| WO | WO/2001/024812 A1 | 4/2001 |
| WO | WO/2001/029246 A1 | 4/2001 |
| WO | WO/2002/030954 A1 | 4/2002 |
| WO | WO/2002/031140 A1 | 4/2002 |
| WO | WO/2002/044215 A2 | 6/2002 |
| WO | WO/2002/066516 A2 | 8/2002 |
| WO | WO/2003/025018 A2 | 3/2003 |
| WO | WO/2003/072713 A2 | 9/2003 |
| WO | WO/2004/058822 A2 | 7/2004 |
| WO | WO/2004/065540 A2 | 8/2004 |
| WO | WO/2005/075511 A1 | 8/2005 |
| WO | WO/2006/113665 A2 | 10/2006 |
| WO | WO/2007/019620 A1 | 2/2007 |
| WO | WO/2007/031875 A2 | 3/2007 |
| WO | WO/2007/039818 A2 | 4/2007 |
| WO | WO/2007/042261 A2 | 4/2007 |
| WO | WO/2007/117600 A2 | 10/2007 |
| WO | WO/2008/119353 A1 | 10/2008 |
| WO | WO/2008/119565 A2 | 10/2008 |
| WO | WO/2008/119566 A2 | 10/2008 |
| WO | WO/2009/080251 A1 | 7/2009 |
| WO | WO/2009/080252 A1 | 7/2009 |
| WO | WO/2009/080254 A1 | 7/2009 |
| WO | WO/2009/132058 A2 | 10/2009 |
| WO | WO/2010/037836 A2 | 4/2010 |
| WO | WO/2010/037837 A2 | 4/2010 |
| WO | WO/2010/037838 A2 | 4/2010 |
| WO | WO/2010/063785 A2 | 6/2010 |
| WO | WO/2010/104949 A2 | 9/2010 |
| WO | WO/2010/145792 A1 | 12/2010 |
| WO | WO/2011/028952 A1 | 3/2011 |
| WO | WO/2011/131746 A2 | 10/2011 |
| WO | WO/2012/004811 A2 | 1/2012 |
| WO | WO/2012/020038 A1 | 2/2012 |
| WO | 2012/066058 A1 | 5/2012 |
| WO | WO/2012/066058 A1 | 5/2012 |
| WO | WO/2012/107416 A2 | 8/2012 |
| WO | WO/2012/116927 A1 | 9/2012 |
| WO | WO/2012/130831 A1 | 10/2012 |
| WO | WO/2012/143498 A1 | 10/2012 |
| WO | WO/2012/146628 A1 | 11/2012 |
| WO | WO/2012/162067 A2 | 11/2012 |
| WO | WO/2012/163805 A1 | 12/2012 |
| WO | WO/2013/026831 A1 | 2/2013 |
| WO | WO/2013/026833 A1 | 2/2013 |
| WO | WO/2013/026835 A1 | 2/2013 |
| WO | WO/2013/026837 A1 | 2/2013 |
| WO | WO/2013/026839 A1 | 2/2013 |
| WO | WO/2013/055958 A1 | 4/2013 |
| WO | 2013/072406 A1 | 5/2013 |
| WO | 2013/072415 A1 | 5/2013 |
| WO | WO/2013/072415 A1 | 5/2013 |
| WO | WO/2013/154760 A1 | 10/2013 |
| WO | WO/2014/023679 A1 | 2/2014 |
| WO | WO/2014/056783 A1 | 4/2014 |
| WO | WO/2014/068079 A1 | 5/2014 |
| WO | WO/2014/089335 A2 | 6/2014 |
| WO | WO/2014/122143 A1 | 8/2014 |
| WO | WO/2014/122144 A1 | 8/2014 |
| WO | WO/2014/140248 A1 | 9/2014 |

OTHER PUBLICATIONS

Ryan, M.C., et al., "Antibody Targeting of B-Cell Maturation Antigen on Malignant Plasma Cells," Molecular Cancer Therapeutics 6(11):3009-3018, American Association of Cancer Research, United States (2007).

Kontermann, R.E., "Dual Targeting Strategies with Bispecific Antibodies," mAbs 4(2):182-197, Taylor and Francis, United States (2012).

Merchant, A.M., et al., "An Efficient Route to Human Bispecific IgG," Nature Biotechnology 16(7):677-681, Nature Publishing Group, United States (1998).

Atwell, S., et al., "Stable Heterodimers from Remodeling the Domain Interface of a Homodimer Using a Phage Display Library," Journal of Molecular Biology 270(1):26-35, Elsevier, England (1997).

Xie, Z., et al., "A New Format of Bispecific Antibody: Highly Efficient Heterodimerization, Expression and Tumor Cell Lysis," Journal of Immunological Methods 296(1-2):95-101, Elsevier, Netherlands (2005).

Salmeron, A., et al., "A Conformational Epitope Expressed upon Association of CD3-epsilon with either CD3-delta or CD3-gamma is the Main Target for Recognition by Anti-CD3 Monoclonal Antibodies," Journal of Immunology 147(9):3047-3052, American Association of Immunologists, United States (1991).

Holliger, P, and Hudson, P.J., "Engineered Antibody Fragments and the Rise of Single Domains," Nature Biotechnology 23(9):1126-1136, Nature America Publishing, United States (2005).

Chan, A.C. and Carter, P.J., "Therapeutic Antibodies for Autoimmunity and Inflammation," Nature Reviews. Immunology 10(5):301-316, Nature Publishing Group, England (2010).

Cuesta, A.M., et al., "Multivalent Antibodies: When Design Surpasses Evolution," Trends in Biotechnology 28(7):355-362, Elsevier Science Publishers, England (2010).

Dimopoulos, M.A. and Terpos, E., "Multiple Myeloma," Annals of Oncology 21(Suppl 7):Vii143-Vii150, Oxford University Press, England (2010).

Sanz, I. and Lee, F.E.,"B Cells as Therapeutic Targets in SLE," Nature Reviews Rheumatology 6(6):326-337, Nature Publishing Group, United States (2010).

Colvin, R.B. and Smith, R.N., "Antibody-Mediated Organ-Allograft Rejection," Nature Reviews Immunology 5(10):807-817, Nature Publishing Group, England (2005).

Trpkov, K., et al., "Pathologic Features of Acute Renal Allograft Rejection Associated with Donor-Specific Antibody, Analysis Using the Banff Grading Schema," Transplantation 61(11):1586-1592, Lippincott Williams and Wilkins, United States (1996).

Regele, H., et al., "Capillary Deposition of Complement Split Product C4d in Renal Allografts is Associated with Basement Membrane Injury in Peritubular and Glomerular Capillaries: A Contribution of Humoral Immunity to Chronic Allograft Rejection," Journal of the American Society of Nephrology 13(9):2371-2380, American Society of Nephrology, United States (2002).

Fotheringham, J., et al., "Transplant Glomerulopathy: Morphology, Associations and Mechanism," Nephron Clinical Practice 113(1):c1-c7, National Academy of Sciences, United States (2009).

Cosio, F.G., et al., "Transplant Glomerulopathy," American Journal of Transplantation 8(3):492-496, Wiley-Blackwell on behalf of the American Society of Transplant Surgeons and the American Society of Transplantation, United States (2008).

Mossner, E., et al., "Increasing the Efficacy of CD20 Antibody Therapy through the Engineering of a New Type II anti-CD20 Antibody with Enhanced Direct and Immune Effector Cell-Mediated B-Cell Cytotoxicity," Blood 115(22):4393-4402, American Society of Hematology, United States (2010).

Salles, G., et al., "Phase 1 Study Results of the Type II Glycoengineered Humanized Anti-CD20 Monoclonal Antibody Obinutuzumab (GA101) in B-cell lymphoma Patients," Blood 119(22):5126-5132, American Society of Hematology, United States (2012).

Gordon, N.C., et al., "BAFF/BLyS Receptor 3 Comprises a Minimal TNF Receptor-like Module that encodes a Highly Focused Ligand-Binding Site," Biochemistry 42(20):5977-5983, American Chemical Society, United States (2003).

(56) References Cited

OTHER PUBLICATIONS

Choi, B.D., et al., "Bispecific Antibodies Engage T Cells for Antitumor Immunotherapy," Expert Opinion on Biological Therapy 11(7):843-853, Taylor and Francis, England (2011).
Wolf, E., et al., "BiTEs: Bispecific Antibody Constructs with Unique Anti-Tumor Activity," Drug Discovery Today 10(18):1237-1244, Elsevier Science Ltd., England (2005).
Kipriyanov, S.M., et al., "Bispecific CD3×CD19 Diabody for T Cell-Mediated Lysis of Malignant Human B Cells," International Journal of Cancer 77(5):763-772, Wiley-Liss, United States (1998).
He, M. and Taussig, M.J., "Rapid Discovery of Protein Interactions by Cell-Free Protein Technologies," Biochemical Society Transactions 35(Pt 5):962-965, Portland Press on Behalf of The Biochemical Society, England (2007).
Woof, J.M. and Burton, D.R., "Human Antibody-Fc Receptor Interactions Illuminated by Crystal Structures," Nature Reviews Immunology 4(2):89-99, Nature Publishing Group, England (2004).
Lukas, T.J., et al., "Inhibition of C1-Mediated Immune Hemolysis by Monomeric and Dimeric Peptides from the Second Constant Domain of Human Immunoglobulin G," Journal of Immunology 127(6):2555-2560, American Association of Immunologists, United States (1981).
Burton, D.R., et al., "The C1q Receptor Site on Immunoglobulin G," Nature 288(5789):338-344, Nature Publishing Group, England (1980).
Thommesen, J.E., et al., "Lysine 322 in the Human IgG3 C(H)2 Domain is Crucial for Antibody Dependent Complement Activation," Molecular Immunology 37(16):995-1004, Pergamon Press, England (2000).
Idusogie, E.E., et al., "Mapping of the C1q Binding Site on Rituxan, A Chimeric Antibody with a Human IgG1 Fc," The Journal of Immunology 164(8):4178-4184, American Association of Immunologists, United States (2000).
Hezareh, M., et al., "Effector Function Activities of a Panel of Mutants of a Broadly Neutralizing Antibody against Human Immunodeficiency Virus type 1," Journal of Virology 75(24):12161-12168, American Society for Microbiology, United States (2001).
Morgan, A., et al., "The N-terminal End of the CH2 Domain of Chimeric Human IgG1 Anti-HLA-DR is Necessary for C1q, Fc(gamma)RI and Fc(gamma)RIII Binding," Immunology 86(2):319-324, Blackwell Scientific Publications, England (1995).
Sondermann, P., et al., "The 3.2-A Crystal Structure of the Human IgG1 Fc Fragment-Fc(gamma)RIII Complex," Nature 406(6793):267-273, Nature Publishing Group, England (2000).
Jefferis, R. and Lund, J., "Interaction Sites on Human IgG-Fc for Fc(gamma)R: Current Models," Immunology Letters 82(1-2):57-65, Elsevier/North-Holland Biomedical Press, Netherlands (2002).
Duncan, A.R., et al., "Localization of the Binding Site for the Human High-Affinity Fc Receptor on IgG," Nature 332(6164):563-564, Nature Publishing Group, England (1988).
Lund, J., et al., "Human Fc(gamma)RI and Fc(gamma)RII Interact with Distinct but Overlapping Sites on Human IgG," Journal of Immunology 147(8):2657-2662, American Association of Immunologists, United States (1991).
Hutchins, J.T., et al., "Improved Biodistribution, Tumor Targeting, and Reduced Immunogenicity in Mice with a (gamma)4 Variant of Campath-1H," Proceedings of the National Academy of Sciences USA 92(26):11980-11984, National Academy of Sciences, United States (1995).
Lund, J., et al., "Oligosaccharide-Protein Interactions in IgG can Modulate Recognition by Fc(gamma) Receptors," FASEB Journal 9(1):115-119, The Federation, United States (1995).
Jefferis, R., et al., "Modulation of Fc(gamma)R and Human Complement Activation by IgG3-core Oligosaccharide Interactions," Immunology Letters 54(2-3):101-104, Elsevier/North-Holland Biomedical Press, Netherlands (1996).
Lund, J., et al., "Multiple Interactions of IgG with its Core Oligosaccharide can Modulate Recognition by Complement and Human Fc(gamma) Receptor I and Influence the Synthesis of Its Oligosaccharide Chains," Journal of Immunology 157(11):4963-4969, American Association of Immunologists, United States (1996).
Armour, K.L., et al., "Recombinant Human IgG Molecules Lacking Fc(gamma) Receptor I Binding and Monocyte Triggering Activities," European Journal of Immunology 29(8):2613-2624, Wiley-VCH, Germany (1999).
Reddy M.P., et al., "Elimination of Fc Receptor-Dependent Effector Functions of a Modified IgG4 Monoclonal Antibody to Human CD4," Journal of Immunology 164(4):1925-1933, American Association of Immunologists, United States (2000).
Xu, D., et al., "In Vitro Characterization of Five Humanized OKT3 Effector Function Variant Antibodies," Cellular Immunology 200(1):16-26, Academic Press, United States (2000).
Idusogie, E.E., et al., "Engineered Antibodies with Increased Activity to Recruit Complement," The Journal of Immunology 166(4):2571-2575, American Association of Immunologists, United States (2001).
Shields, R.L., et al., "High Resolution Mapping of the Binding Site on Human IgG1 for Fc(gamma)RI, Fc(gamma)RII, Fc(gamma)RIII, and FcRn and Design of IgG1 Variants with Improved Binding to the Fc(gamma)R," The Journal of Biological Chemistry 276(9):6591-6604, American Society for Biochemistry and Molecular Biology, United States (2001).
Topp, M.S., et al., "Targeted Therapy with the T-cell-engaging Antibody Blinatumomab of Chemotherapy-refractory Minimal Residual Disease in B-lineage Acute Lymphoblastic Leukemia Patients Results in High Response Rate and Prolonged Leukemia-free Survival," Journal of Clinical Oncology 29(18):2493-2498, American Society of Clinical Oncology, United States (2011).
Umana, P., et al., "Engineered Glycoforms of an Antineuroblastoma IgG1 with Optimized Antibody-Dependent Cellular Cytotoxic Activity," Nature Biotechnology 17(2):176-180, Nature America Publishing, United States (1999).
Davies, J., et al., "Expression of GnTIII in a Recombinant Anti-CD20 CHO Production Cell Line: Expression of Antibodies with Altered Glycoforms Leads to an Increase in ADCC through Higher Affinity for FC gamma RIII," Biotechnology and Bioengineering 74(4):288-294, Wiley, United States (2001).
Shields, R.L., et al., "Lack Fucose on Human IgG1 N-linked Oligosaccharide Improves Binding to Human Fcgamma RIII and Antibody-Dependent Cellular Toxicity." The Journal of Biological Chemistry 277(30):26733-26740, American Society for Biochemistry and Molecular Biology, United States (2002).
Shinkawa, T., et al., "The Absence of Fucose but Not the Presence of Galactose or Bisecting N-acetylglucosamine of Human IgG1 Complex-Type Oligosaccharides Shows the Critical Role of Enhancing Antibody-Dependent Cellular Cytotoxicity." The Journal of Biological Chemistry 278(5):3466-3473, American Society for Biochemistry and Molecular Biology, United States (2003).
Mori, K., et al., "Non-Fucosylated Therapeutic Antibodies: The Next Generation of Therapeutic Antibodies," Cytotechnology 55(2-3):109-114, Kluwer Academic Publishers, Netherlands (2007).
Satoh, M., et al., "Non-Fucosylated Therapeutic Antibodies as Next-Generation Therapeutic Antibodies," Expert Opinion on Biological Therapy 6(11):1161-1173, Taylor and Francis, England (2006).
Morrison, S.L., et al., "Chimeric Human Antibody Molecules: Mouse Antigen-Binding Domains with Human Constant Region Domains," Proceedings of the National Academy of Sciences USA 81(21):6851-6855, National Academy of Sciences, United States (1984).
Riechmann, L., et al., "Reshaping Human Antibodies for Therapy," Nature 332(6162):323-327, Nature Publishing Group, United States (1988).
Van Dijk, M.A. and Van De Winkel, J.G., "Human Antibodies as Next Generation Therapeutics," Current Opinion in Chemical Biology 5(4):368-374, Elsevier, England (2001).
Jakobovits, A., et al., "Analysis of Homozygous Mutant Chimeric Mice: Deletion of the Immunoglobulin Heavy-Chain Joining Region Blocks B-Cell Development and Antibody Production," Proceedings of the National Academy of Sciences USA 90(6):2551-2555, National Academy of Sciences, United States (1993).

(56) References Cited

OTHER PUBLICATIONS

Jakobovits, A., et al., "Germ-Line Transmission and Expression of a Human-Derived Yeast Artificial Chromosome," Nature 362(6417):255-258, Nature Publishing Group, England (1993).
Hoogenboom, H.R. and Winter, G., "By-Passing Immunisation. Human Antibodies from Synthetic Repertoires of Germline VH Gene Segments Rearranged in vitro," Journal of Molecular Biology 227(2):381-388, Elsevier, England (1992).
Marks, J.D., et al., "By-passing immunization. Human Antibodies from V-Gene Libraries Displayed on Phage," Journal of Molecular Biology 222(3):581-597, Academic Press Limited, United States (1991).
Boerner, P., et al., "Production of Antigen-specific Human Monoclonal Antibodies from in Vitro-primed Human Splenocytes," Journal of Immunology 147(1):86-95, The American Association of Immunologists, United States (1991).
Cohen, S.N., et al., "Nonchromosomal Antibiotic Resistance in Bacteria: Genetic Transformation of *Escherichia coli* by R-factor DNA." Proceedings of the National Academy of Sciences USA 69(8):2110-2114. National Academy of Sciences. United States (1972).
Makrides, S.C., "Components of Vectors for Gene Transfer and Expression in Mammalian Cells," Protein Expression and Purification 17(2):183-202, Academic Press, United States (1999).
Geisse, S., et al., "Eukaryotic Expression Systems: A Comparison," Protein Expression and Purification 8(3):271-282, Academic Press, United States (1996).
Kaufman, R.J., "Overview of Vector Design for Mammalian Gene Expression," Molecular Biotechnology 16(2):151-160, Humana Press, United States (2000).
Barnes, L.M., et al., "Advances in Animal Cell Recombinant Protein Production: GS-NS0 Expression System," Cytotechnology 32(2):109-123, Kluwer Academic Publishers, Netherlands (2000).
Barnes, L.M., et al., "Characterization of the Stability of Recombinant Protein Production in the GS-NS0 Expression System," Biotechnology and Bioengineering 73(4):261-270, Wiley, United States (2001).
Durocher, Y., et al., "High-level and High-throughput Recombinant Protein Production by Transient Transfection of Suspension-growing Human 293-EBNA1 Cells," Nucleic Acids Research 30(2):E9, Oxford University Press, England (2002).
Orlandi, R., et al., "Cloning Immunoglobulin Variable Domains for Expression by the Polymerase Chain Reaction," Proceedings of the National Academy of Sciences USA 86(10):3833-3837, National Academy of Sciences, United States (1989).
Carter, P., et al., "Humanization of an Anti-p185HER2 Antibody for Human Cancer Therapy," Proceedings of the National Academy of Sciences USA 89(10):4285-4289, National Academy of Sciences, United States (1992).
Norderhaug, L., et al., "Versatile Vectors for Transient and Stable Expression of Recombinant Antibody Molecules in Mammalian Cells," Journal Immunological Methods 204(1):77-87, Elsevier, Netherlands (1997).
Schlaeger, E.J. and Christensen, K., "Transient Gene Expression in Mammalian Cells Grown in Serum-Free Suspension Culture," Cytotechnology 30(1-3):71-83, Kluwer Academic Publishers, Netherlands (1999).
Schlaeger, E.J., "The Protein Hydrolysate, Primatone RL, is a Cost-Effective Multiple Growth Promoter of Mammalian Cell Culture in Serum-Containing and Serum-Free Media and Displays Anti-Apoptosis Properties," Journal of Immunological Methods 194(2):191-199, Elsevier, Netherlands (1996).
Dreier, T., et al., "Extremely Potent, Rapid and Costimulation-Independent Cytotoxic T-Cell Response against Lymphoma Cells Catalyzed by a Single-Chain Bispecific Antibody," International Journal of Cancer 100(6):690-697. Wiley-Liss, United States (2002).
Klinger, M., et al., "Immunopharmacologic Response of Patients with B-Lineage Acute Lymphoblastic Leukemia to Continuous Infusion of T Cell-Engaging CD19/CD3-Bispecific BiTE Antibody Blinatumomab," Blood 119(26):6226-6233, American Society of Hematology, United States (2012).
Moreaux, J., et al., "BAFF and APRIL Protect Myeloma Cells from Apoptosis Induced by Interleukin 6 Deprivation and Dexamethasone," Blood 103(8):3148-3157, American Society of Hematology, United States (2004).
Edelman, G.M. et al., "The Covalent Structure of an Entire gammaG Immunoglobulin Molecule," Proceedings of the National Academy of Sciences USA 63(1):78-85, National Academy of Sciences, United States (1969).
Mack, M., et al., "A Small Bispecific Antibody Construct Expressed as a Functional Single-Chain Molecule with High Tumor Cell Cytotoxicity," Proceedings of the National Academy of Sciences USA 92(15):7021-7025, National Academy of Sciences, United States (1995).
Ridgway, J.B.B., et al., "Knobs-into-holes' engineering of antibody CH3 domains for heavy chain heterodimerization," Protein Engineering 9(7):617-621, Oxford University Press, England (1996).
International Preliminary Report on Patentability and Written Opinion for International Application No. PCT/EP2014/052190, International Bureau of WIPO, Geneva, Switzerland, dated Aug. 11, 2015, 8 pages.
International Search Report for International Application No. PCT/EP2014/052190, European Patent Office, Netherlands, dated May 13, 2014, 6 pages.
Baker, K. P., et al., Generation and characterization of LymphoStat-B, a human monoclonal antibody that antagonizes the bioactivities of B lymphocyte stimulator, Arthritis Rheum. Nov. 2003;48(11):3253-65.
Bellucci, R., et al., Graft-versus-tumor response in patients with multiple myeloma is associated with antibody response to BCMA, a plasma-cell membrane receptor, Blood. May 15, 2005;105(10):3945-50.
Carpenter, R. O., et al., B-cell maturation antigen is a promising target for adoptive T-cell therapy of multiple myeloma, Clin Cancer Res. Apr. 15, 2013;19(8):2048-60.
Claudio, J. O., et al., A molecular compendium of genes expressed in multiple myeloma, Blood. Sep. 15, 2002;100(6):2175-86.
Hatzoglou, A., et al., TNF Receptor Family Member BCMA (B Cell Maturation) Associates with TNF Receptor-Associated Factor (TRAF) 1, TRAF2, and TRAF3 and Activates NF-κB, Elk-1, c-Jun N-Terminal Kinase, and p38 Mitogen-Activated Protein Kinase, J Immunol Aug. 1, 2000, 165 (3) 1322-1330.
Laabi, Y., et al., The BCMA gene, preferentially expressed during B lymphoid maturation, is bidirectionally transcribed, Nucleic Acids Research, 1994, vol. 22, No. 7 1147-1154.
Novak, A. J., et al., Expression of BCMA, TACI, and BAFF-R in multiple myeloma: a mechanism for growth and survival, Blood. Jan. 15, 2004;103(2):689-94.
Sanchez, E., et al., Serum B-cell maturation antigen is elevated in multiple myeloma and correlates with disease status and survival, Br J Haematol. Sep. 2012;158(6):727-38.
Thompson, J. S., et al., BAFF binds to the tumor necrosis factor receptor-like molecule B cell maturation antigen and is important for maintaining the peripheral B cell population, J Exp Med. Jul. 3, 2000;192(1):129-35.
Vidal-Laliena, M., et al., Characterization of antibodies submitted to the B cell section of the 8th Human Leukocyte DiVerentiation Antigens Workshop by Xow cytometry and immunohistochemistry.
Ju, S., et al., Correlation of expression levels of BLyS and its receptors with multiple, Clinical Biochemistry 42 (2009) 387-399.
Sanchez, E., et al., The clinical significance of B-cell maturation antigen as a therapeutic target and biomarker, Expert Rev Mol Diagn. Apr. 2018;18(4):319-329.
Friedman, K. M., et al., Effective Targeting of Multiple BCMA-Expressing Hematological Malignances by Anti-BCMA CAR T Cells, Hum Gene Ther. May 2018;29(5):585-601.
Coquery, C. M., et al., Regulatory Roles of the Tumor Necrosis Factor Receptor BCMA, Crit Rev Immunol. 2012 ; 32(4): 287-305.

* cited by examiner

Fig. 9
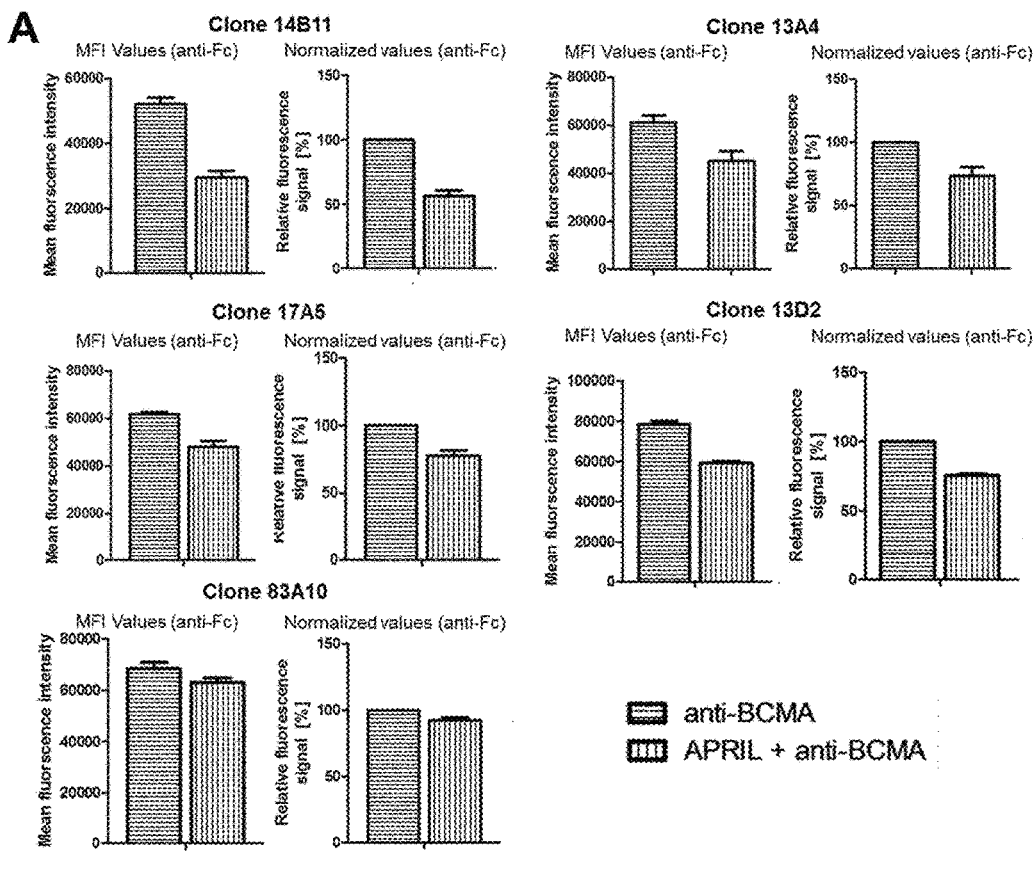
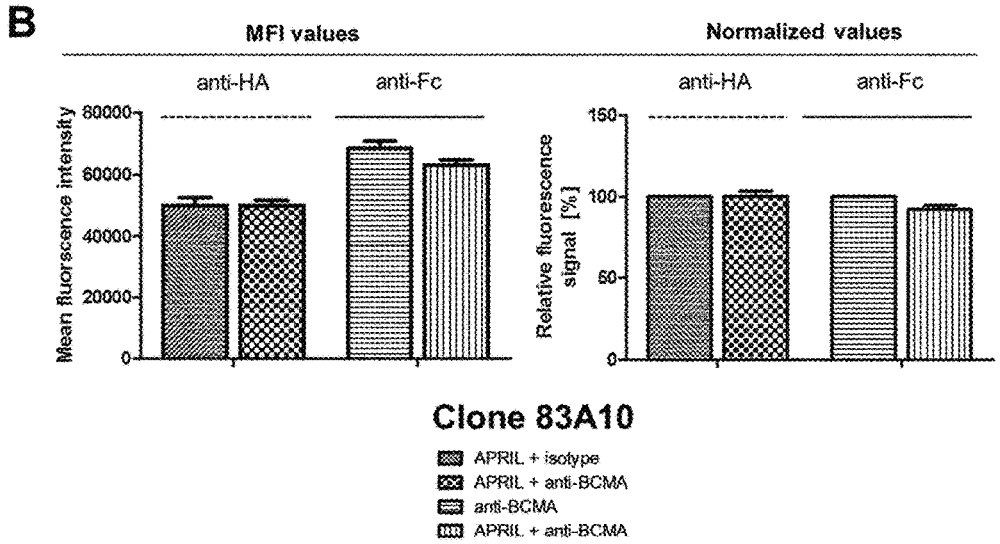

BISPECIFIC ANTIBODIES AGAINST CD3 AND BCMA

REFERENCE TO A SEQUENCE LISTING SUBMITTED ELECTRONICALLY

The content of the electronically submitted sequence listing (Name: 3681_0010003_SL.txt; Size: 36,997 bytes; and Date of Creation: Jul. 27, 2015) is herein incorporated by reference in its entirety.

The present invention relates to novel bispecific antibodies against CD3ε and BCMA, their manufacture and use.

BACKGROUND OF THE INVENTION

Human B cell maturation target, also known as BCMA; TR17_HUMAN, TNFRSF17 (UniProt Q02223), is a member of the tumor necrosis receptor superfamily that is preferentially expressed in differentiated plasma cells [Laabi et al. 1992; Madry et al. 1998]. BCMA is a non glycosylated type III transmembrane protein, which is involved in B cell maturation, growth and survival. BCMA is a receptor for two ligands of the TNF superfamily: APRIL (a proliferation-inducing ligand), the high-affinity ligand to BCMA and the B cell activation factor BAFF, the low-affinity ligand to BCMA (THANK, BlyS, B lymphocyte stimulator, TALL-1 and zTNF4). APRIL and BAFF show structural similarity and overlapping yet distinct receptor binding specificity. The negative regulator TACI also binds to both BAFF and APRIL. The coordinate binding of APRIL and BAFF to BCMA and/or TACI activates transcription factor NF-κB and increases the expression of pro-survival Bcl-2 family members (e.g. Bcl-2, Bcl-xL, Bcl-w, Mcl-1, A1) and the downregulation of pro-apoptotic factors (e.g. Bid, Bad, Bik, Bim, etc.), thus inhibiting apoptosis and promoting survival. This combined action promotes B cell differentiation, proliferation, survival and antibody production (as reviewed in Rickert R C et al., Immunol Rev (2011) 244 (1): 115-133). Antibodies against BCMA are described e.g. in Gras M-P. et al. Int Immunol. 7 (1995) 1093-1106, WO200124811, and WO200124812. The use of anti-BCMA antibodies for the treatment of lymphomas and multiple myeloma are mentioned e.g. in WO2002066516 and WO2010104949.

The TCR/CD3 complex of T-lymphocytes consists of either a TCR alpha (α)/beta (β) or TCR gamma (γ)/delta (δ) heterodimer coexpressed at the cell surface with the invariant subunits of CD3 labeled gamma (γ), delta (δ), epsilon (ε), zeta (ζ) and eta (η). Human CD3ε is described under UniProt P07766 (CD3E_HUMAN). An anti CD3ε antibody described in the state of the art is SP34 (Yang S J, The Journal of Immunology (1986) 137; 1097-1100). SP34 reacts with both primate and human CD3. SP34 is available from Pharmingen. A further anti CD3 antibody described in the state of the art is UCHT-1 (see WO2000041474). A further anti CD3 antibody described in the state of the art is BC-3 (Fred Hutchinson Cancer Research Institute; used in Phase I/II trials of GvHD, Anasetti et al., Transplantation 54: 844 (1992)). SP34 differs from UCHT-1 and BC-3 in that SP-34 recognizes an epitope present on solely the ε chain of CD3 (see Salmeron et al., (1991) J. Immunol. 147: 3047) whereas UCHT-1 and BC-3 recognize an epitope contributed by both the ε and γ chains. The sequence of an antibody with the same sequence as of antibody SP34 is mentioned in WO2008119565, WO2008119566, WO2008119567, WO2010037836, WO2010037837 and WO2010037838. A sequence which is 96% identical to VH of antibody SP34 is mentioned in U.S. Pat. No. 8,236,308 (WO2007042261). VH and VL sequences of a further antibody with the same sequences as of SP34 are shown in SEQ ID NO:7 and 8.

A wide variety of recombinant bispecific antibody formats have been developed in the recent past, e.g. by fusion of, e.g. an IgG antibody format and single chain domains (see Kontermann R E, mAbs 4:2, (2012) 1-16). Bispecific antibodies wherein the variable domains VL and VH or the constant domains CL and CH1 are replaced by each other are described in WO2009080251 and WO2009080252.

An approach to circumvent the problem of mispaired byproducts, which is known as 'knobs-into-holes', aims at forcing the pairing of two different antibody heavy chains by introducing mutations into the CH3 domains to modify the contact interface. On one chain bulky amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway J B, Presta L G, Carter P; and WO1996027011). The percentage of heterodimer could be further increased by remodeling the interaction surfaces of the two CH3 domains using a phage display approach and the introduction of a disulfide bridge to stabilize the heterodimers (Merchant A. M, et al, Nature Biotech 16 (1998) 677-681; Atwell S, Ridgway J B, Wells J A, Carter P., J Mol Biol 270 (1997) 26-35). New approaches for the knobs-into-holes technology are described in e.g. in EP 1870459A1. Although this format appears very attractive, no data describing progression towards the clinic are currently available. One important constraint of this strategy is that the light chains of the two parent antibodies have to be identical to prevent mispairing and formation of inactive molecules. Thus this technique is not appropriate for easily developing recombinant, bispecific antibodies against two targets starting from two antibodies against the first and the second target, as either the heavy chains of these antibodies and/or the identical light chains have to be optimized. Xie, Z., et al, J Immunol Methods 286 (2005) 95-101 refers to a format of bispecific antibody using scFvs in combination with knobs-into-holes technology for the FC part. WO 2012116927 and WO 2010/145792, and mention exchanging the CH1 and CL domains. WO 2009/080254 mentions knob in hole constructs for producing bispecific antibodies.

Antibodies against BCMA are described e.g. in Gras M-P. et al. Int Immunol. 7 (1995) 1093-1106, WO200124811, WO200124812, WO2010104949 and WO2012163805. Antibodies against BCMA and their use for the treatment of lymphomas and multiple myeloma are mentioned e.g. in WO2002066516 and WO2010104949. WO2013154760 relates to chimeric antigen receptors comprising a BCMA recognition moiety and a T-cell activation moiety.

Ryan, M C et al., Mol. Cancer Ther. 6 (2007) 3009-3018 relate selectively targeting of BCMA for plasma cell malignancies. Antibody SG1, with ligand blocking activity could promote cytotoxicity of multiple myeloma (MM) cell lines as naked antibodies or as antibody-drug conjugates (ADC). SG1, an inhibitory BCMA antibody, blocks APRIL-dependent activation of nuclear factor-κB in a dose-dependent manner in vitro. Cytotoxicity of SG1 was assessed as a naked antibody after chimerization with and without Fc mutations that enhance FcγRIIIA binding. Ryan also mentions antibody SG2 which does not significantly inhibit APRIL binding to BCMA. However SG2 showed a 20 fold higher $IC_{50}$ value as SG1 measured as cytotoxic activity of a drug conjugate against BCMA positive myeloma cell lines. Ryan conclude that BCMA antibodies can act on MM cell lines through multiple mechanisms that include inhibition of APRIL-dependent NF-κB activation, promotion of tumor cell lysis by natural killer cell-mediated ADCC activity, and induction of cytotoxicity by ADCs.

Bispecific antibodies against CD3 and BCMA are mentioned in WO2007117600, WO2009132058, WO2012066058, and WO2012143498.

SUMMARY OF THE INVENTION

The invention comprises a bispecific antibody specifically binding to the two targets human CD3ε (further named also as "CD3") and the extracellular domain of human BCMA (further named also as "BCMA"), characterized in that the binding of said antibody in a concentration of 6.25 nM is not reduced by 140 ng/ml murine APRIL for more than 10%, preferably not reduced by for more than 1% measured in an ELISA assay as OD at 450 nm compared to the binding of said antibody to human BCMA without APRIL. Preferably the bispecific antibody is characterized in that the binding of said antibody in a concentration of 50 nM is not reduced by 140 ng/ml murine APRIL for more than 10%, measured in an ELISA assay as OD at 450 nm, compared to the binding of said antibody to human BCMA without APRIL.

Preferably the antibody according to the invention is characterized in showing an EC50 value for binding of anti-BCMA antibodies to H929 cells (ATCC® CRL9068™) of 15 nM or lower.

The invention relates to a bispecific antibody specifically binding to the two targets human CD3ε (further named also as "CD3") and the extracellular domain of human BCMA (further named also as "BCMA"), characterized in that
  i) said bispecific antibody is a fusion protein of a Fab fragment of an anti-CD3 antibody chemically linked at its N-terminus to the C-terminus of a Fab fragment of an anti-BCMA antibody and
  ii) the variable domains VL and VH of the anti-CD3 antibody or the constant domains CL and CH1 are replaced by each other.

Preferably a VH domain of said anti-CD3 antibody is linked to a CH1 or CL domain of said anti-BCMA antibody. Preferably a VL domain of said anti-CD3 antibody is linked to a CH1 or CL domain of said anti-BCMA antibody.

Preferably the bispecific antibody comprises not more than one Fab fragment of an anti-CD3 antibody, not more than two Fab fragments of an anti-BCMA antibody and not more than one Fc part, preferably a human Fc part. Preferably not more than one Fab fragment of an anti-CD3 antibody and not more than one Fab fragment of an anti-BCMA antibody are linked to the Fc part and linking is performed via C-terminal binding of the Fab fragment(s) to the hinge region. Preferably the second Fab fragment of an anti-BCMA antibody is linked via its C-terminus either to the N-terminus of the Fab fragment of an anti-CD3 antibody or to the hinge region of the Fc part. The preferred bispecific antibodies are shown in FIG. 3.

Especially preferred are these bispecific antibodies comprising only the Fab fragments and the Fc part as specified:
  Fab BCMA-Fc-Fab CD3-Fab BCMA (bispecific format 3.1)
  Fc-Fab CD3-Fab BCMA (bispecific format 3.2),
  Fab CD3-Fab BCMA (bispecific format 3.3),
  Fab CD3-Fab BCMA-Fab BCMA (bispecific format 3.4),
Preferably the bispecific antibody comprises a second Fab fragment of said anti-BCMA antibody chemically linked with its C-terminus to the N-terminus of the first Fab fragment of said anti-BCMA antibody. Preferably a VH domain of said first anti-BCMA antibody is linked to a CH1 or CL domain of said second anti-BCMA antibody. Preferably a VL domain of said first anti-BCMA antibody is linked to a CH1 or CL domain of said second anti-BCMA antibody.

Preferably the bispecific antibody comprises a Fc part linked with its N-terminus to the C-terminus of said anti-CD3 antibody. Preferably the bispecific antibody comprises a Fc part linked with its first N-terminus to the C-terminus of said anti-CD3 antibody and a second Fab fragment of said anti-BCMA antibody linked with its C-terminus to the second N-terminus of the Fc part. Preferably the CL domain of the CD3 antibody Fab fragment is linked to the hinge region of the Fc part. Preferably the CH1 domain of the BCMA antibody Fab fragment is linked to the hinge region of the Fc part.

The Fab fragments are chemically linked together by the use of an appropriate linker according to the state of the art. Preferably a $(Gly_4-Ser_1)_3$ linker is used (Desplancq D K et al., Protein Eng. 1994 August; 7(8):1027-33 and Mack M. et al., PNAS Jul. 18, 1995 vol. 92 no. 15 7021-7025).

The antibodies according to the invention mentioned above are preferably characterized by the features mentioned below, especially in regard to that binding of said antibody is not reduced by 100 ng/ml APRIL and preferably by BAFF for more than 20% and does not alter APRIL-dependent NF-κB activation for more than 20%, with and without APRIL and preferably with and without BAFF for more than 20%.

The invention relates to a bispecific antibody specifically binding to the two targets human CD3ε (further named also as "CD3") and the extracellular domain of human BCMA (further named also as "BCMA"), characterized in
  a) comprising the light chain and heavy chain of an antibody specifically binding to one of said targets; and
  b) comprising the light chain and heavy chain of an antibody specifically binding to the other one of said targets, wherein the variable domains VL and VH or the constant domains CL and CH1 are replaced by each other, and characterized in that
  c) the binding of said antibody specifically binding to human BCMA is not reduced by 100 ng/ml APRIL for more than 20% measured in an ELISA assay as OD at 405 nm compared to the binding of said antibody to human BCMA without APRIL,
  d) said antibody does not alter APRIL-dependent NF-κB activation for more than 20%, as compared to APRIL alone, and
  e) said antibody does not alter NF-κB activation without APRIL for more than 20%, as compared without said antibody.

The naked antibody specifically binding to BCMA from which the anti-BCMA antibody portion of the bispecific antibody according to the invention is derived also shows the above mentioned features c) to e).

Preferably the antibody is further characterized in that the binding of said antibody to human BCMA is not reduced by 100 ng/ml APRIL for more than 15%, measured in said ELISA. Preferably the antibody is further characterized in that the binding of said antibody to human BCMA is not reduced by 1000 ng/ml APRIL and not reduced by 1000 ng/ml, for more than 20%, measured in said ELISA. Preferably the antibody is further characterized in that the binding of said antibody to human BCMA is not reduced by 1000 ng/ml APRIL for more than 15%, measured in said ELISA.

Preferably the antibody according to the invention does not alter APRIL-dependent NF-κB activation for more than 15%. Preferably the antibody according to the invention does not alter NF-κB activation without APRIL for more than 15%.

The invention relates to a bispecific antibody specifically binding to the two targets human CD3ε (further named also as "CD3") and the extracellular domain of human BCMA (further named also as "BCMA"), characterized in
  a) comprising the light chain and heavy chain of an antibody specifically binding to one of said targets; and
  b) comprising the light chain and heavy chain of an antibody specifically binding to the other one of said targets, wherein the variable domains VL and VH or the constant domains CL and CH1 are replaced by each other, and characterized in that
  c) the binding of said antibody specifically binding to human BCMA is not reduced by 100 ng/ml APRIL and not reduced by 100 ng/ml BAFF for more than 20% measured in an ELISA assay as OD at 405 nm compared to the binding of said antibody to human BCMA without APRIL or BAFF respectively,
  d) said antibody does not alter APRIL-dependent NF-κB activation for more than 20%, as compared to APRIL alone,
  e) said antibody does not alter BAFF-dependent NF-κB activation for more than 20%, as compared to BAFF alone, and
  f) said antibody does not alter NF-κB activation without BAFF and APRIL for more than 20%, as compared without said antibody.

The naked antibody specifically binding to BCMA from which the anti-BCMA antibody portion of the bispecific antibody according to the invention is derived also shows the above mentioned features c) to f).

Preferably the antibody portion specifically binding to human CD3 is characterized in comprising a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3 of the anti CD3ε antibody (CDR MAB CD3). Preferably the antibody portion specifically binding to human CD3 is characterized in that the variable domains are of SEQ ID NO:7 and 8 (VHVL MAB CD3).

Preferably the antibody portion, preferably the Fab fragment, specifically binding to human BCMA is characterized in comprising a variable domain VH comprising the heavy chain CDRs of SEQ ID NO: 37 to 45, 47 to 55 and 57 to 65 as respectively heavy chain CDR1, CDR2 and CDR3 and a variable domain VL comprising the light chain CDRs of SEQ ID NO: 67 to 75, 77 to 85, and 87 to 95 as respectively light chain CDR1, CDR2 and CDR3 of the anti BCMA antibody. Preferably the antibody portion specifically binding to human BCMA is characterized in that the variable domain VH is selected from the group of SEQ ID NO:17 to 25 and the variable domain VL is selected from the group of SEQ ID NO:27 to 35 respectively.

Preferably the antibody portion, preferably the Fab fragment, specifically binding to human BCMA is characterized in comprising a CDR1H of SEQ ID NO:37, a CDR2H of SEQ ID NO:47, a CDR3H of SEQ ID NO: 57 and a CDR1L of SEQ ID NO:67, a CDR2L of SEQ ID NO:77, a CDR3L of SEQ ID NO: 87 (CDR MAB 13C2). Preferably the antibody portion, preferably the Fab fragment, specifically binding to human BCMA is characterized in comprising a CDR1H of SEQ ID NO:38, a CDR2H of SEQ ID NO:48, a CDR3H of SEQ ID NO: 58 and a CDR1L of SEQ ID NO:68, a CDR2L of SEQ ID NO:78, a CDR3L of SEQ ID NO: 88 (CDR MAB 17A5). Preferably the antibody portion, preferably the Fab fragment, specifically binding to human BCMA is characterized in comprising a CDR1H of SEQ ID NO:39, a CDR2H of SEQ ID NO:49, a CDR3H of SEQ ID NO: 59 and a CDR1L of SEQ ID NO:69, a CDR2L of SEQ ID NO:79, a CDR3L of SEQ ID NO: 89 (CDR MAB 83A10). Preferably the antibody portion, preferably the Fab fragment, specifically binding to human BCMA is characterized in comprising a CDR1H of SEQ ID NO:40, a CDR2H of SEQ ID NO:50, a CDR3H of SEQ ID NO: 60 and a CDR1L of SEQ ID NO:70, a CDR2L of SEQ ID NO:80, a CDR3L of SEQ ID NO: 90 (CDR MAB 13A4). Preferably the antibody portion, preferably the Fab fragment, specifically binding to human BCMA is characterized in comprising a CDR1H of SEQ ID NO:41, a CDR2H of SEQ ID NO:51, a CDR3H of SEQ ID NO: 61 and a CDR1L of SEQ ID NO:71, a CDR2L of SEQ ID NO:81, a CDR3L of SEQ ID NO: 91 (CDR MAB 13D2). Preferably the antibody portion, preferably the Fab fragment, specifically binding to human BCMA is characterized in comprising a CDR1H of SEQ ID NO:42, a CDR2H of SEQ ID NO:52, a CDR3H of SEQ ID NO: 62 and a CDR1L of SEQ ID NO:72, a CDR2L of SEQ ID NO:82, a CDR3L of SEQ ID NO: 92 (CDR MAB 14B11). Preferably the antibody portion, preferably the Fab fragment, specifically binding to human BCMA is characterized in comprising a CDR1H of SEQ ID NO:43, a CDR2H of SEQ ID NO:53, a CDR3H of SEQ ID NO: 63 and a CDR1L of SEQ ID NO:73, a CDR2L of SEQ ID NO:83, a CDR3L of SEQ ID NO: 93 (CDR MAB 14E1). Preferably the antibody portion, preferably the Fab fragment, specifically binding to human BCMA is characterized in comprising a CDR1H of SEQ ID NO:44, a CDR2H of SEQ ID NO:54, a CDR3H of SEQ ID NO: 64 and a CDR1L of SEQ ID NO:74, a CDR2L of SEQ ID NO:84, a CDR3L of SEQ ID NO: 94 (CDR MAB29B11). Preferably the antibody portion, preferably the Fab fragment, specifically binding to human BCMA is characterized in comprising a CDR1H of SEQ ID NO:45, a CDR2H of SEQ ID NO:55, a CDR3H of SEQ ID NO: 65 and a CDR1L of SEQ ID NO:75, a CDR2L of SEQ ID NO:85, a CDR3L of SEQ ID NO: 95 (CDR MAB29F3).

A further embodiment of the invention is characterized in that the bispecific antibody specifically binding to CD3ε and BCMA consists of CDR MAB CD3 and a CDR MAB, selected from the group consisting of 13C2, 17A5, 83A10, 13A4, 13D2, 14B11, 14E1, 29B11 and 29F3 of the bispecific format 3.1. A further embodiment of the invention is characterized in that the bispecific antibody specifically binding to CD3ε and BCMA") consists of CDR MAB CD3 and a CDR MAB, selected from the group consisting of 13C2, 17A5, 83A10, 13A4, 13D2, 14B11, 14E1, 29B11 and 29F3 of the bispecific format 3.2. A further embodiment of the invention is characterized in that the bispecific antibody specifically binding to CD3ε and BCMA") consists of CDR MAB CD3 and a CDR MAB, selected from the group consisting of 13C2, 17A5, 83A10, 13A4, 13D2, 14B11, 14E1, 29B11 and 29F3 of the bispecific format 3.3. A further embodiment of the invention is characterized in that the bispecific antibody specifically binding to CD3ε and BCMA") consists of CDR MAB CD3 and a CDR MAB, selected from the group consisting of 13C2, 17A5, 83A10, 13A4, 13D2, 14B11, 14E1, 29B11 and 29F3 of the bispecific format 3.4.

Preferably the antibody portion, preferably the Fab fragment, specifically binding to human BCMA is characterized in comprising a VH selected from the group consisting of SEQ ID NO: 17 to 25 and/or in comprising a VL selected from the group consisting of SEQ ID NO: 27 to 35.

Preferably the antibody portion, preferably the Fab fragment, specifically binding to human BCMA is characterized in comprising a VH of SEQ ID NO: 17 and a VL of SEQ ID NO: 27 (VHVL MAB 13C2). Preferably the antibody portion, preferably the Fab fragment, specifically binding to human BCMA is characterized in comprising a VH of SEQ ID NO: 18 and a VL of SEQ ID NO: 28 (VHVL MAB 17A5). Preferably the antibody portion, preferably the Fab fragment, specifically binding to human BCMA is characterized in comprising a VH of SEQ ID NO: 19 and a VL of SEQ ID NO: 29 (VHVL MAB 83A10). Preferably the antibody portion, preferably the Fab fragment, specifically binding to human BCMA is characterized in comprising a VH of SEQ ID NO: 20 and a VL of SEQ ID NO: 30 (VHVL MAB 13A4). Preferably the antibody portion, preferably the Fab fragment, specifically binding to human BCMA is characterized in comprising a VH of SEQ ID NO: 21 and a VL of SEQ ID NO: 31 (VHVL MAB13D2). Preferably the antibody portion, preferably the Fab fragment, specifically binding to human BCMA is characterized in comprising a VH of SEQ ID NO: 22 and a VL of SEQ ID NO: 32 (VHVL MAB 14B11). Preferably the antibody portion, preferably the Fab fragment, specifically binding to human BCMA is characterized in comprising a VH of SEQ ID NO: 23 and a VL of SEQ ID NO: 33 (VHVL MAB 14E1). Preferably the antibody portion, preferably the Fab fragment, specifically binding to human BCMA is characterized in comprising a VH of SEQ ID NO: 24 and a VL of SEQ ID NO: 34 (VHVL MAB29B11). Preferably the antibody portion, preferably the Fab fragment, specifically binding to human BCMA is characterized in comprising a VH of SEQ ID NO: 25 and a VL of SEQ ID NO: 35 (VHVL MAB 29F3).

In a further embodiment of the invention, the antibody portion, preferably the Fab fragment, specifically binding to human BCMA is characterized in comprising a CDR1H of SEQ ID NO:46, a CDR2H of SEQ ID NO:56, a CDR3H of SEQ ID NO: 66 and a CDR1L of SEQ ID NO:76, a CDR2L of SEQ ID NO:86, a CDR3L of SEQ ID NO: 96 (CDR MAB 13A7). In a further embodiment of the invention the antibody portion, preferably the Fab fragment, specifically binding to human BCMA is characterized in comprising a VH of SEQ ID NO: 26 and a VL of SEQ ID NO: 36 (VHVL MAB13A7). The binding of antibody MAB 13A7 is reduced by 100 ng/ml APRIL for more than 20% measured in an ELISA assay.

A further embodiment of the invention is characterized in that the bispecific antibody specifically binding to CD3ε and BCMA consists of VHVL MAB CD3 and a VHVL MAB, selected from the group consisting of 13C2, 17A5, 83A10, 13A4, 13D2, 14B11, 14E1, 29B11, and 29F3 of the bispecific format 3.1. A further embodiment of the invention is characterized in that the bispecific antibody specifically binding to CD3ε and BCMA") consists of VHVL MAB CD3 and a VHVL MAB, selected from the group consisting of 13C2, 17A5, 83A10, 13A4, 13D2, 14B11, 14E1, 29B11, and 29F3 of the bispecific format 3.2. A further embodiment of the invention is characterized in that the bispecific antibody specifically binding to CD3ε and BCMA") consists of VHVL MAB CD3 and a VHVL MAB, selected from the group consisting of 13C2, 17A5, 83A10, 13A4, 13D2, 14B11, 14E1, 29B11, 29F3, and 13A7 of the bispecific format 3.3. A further embodiment of the invention is characterized in that the bispecific antibody specifically binding to CD3ε and BCMA") consists of VHVL MAB CD3 and a VHVL MAB, selected from the group consisting of 13C2, 17A5, 83A10, 13A4, 13D2, 14B11, 14E1, 29B11, and 29F3 of the bispecific format 3.4.

Preferably the bispecific antibody according to the invention is characterized in that the CH3 domain of one heavy chain and the CH3 domain of the other heavy chain each meet at an interface which comprises an original interface between the antibody CH3 domains; wherein said interface is altered to promote the formation of the bispecific antibody, wherein the alteration is characterized in that:

a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

Preferably the antibody according to the invention is characterized in that said amino acid residue having a larger side chain volume is selected from the group consisting of arginine (R), phenylalanine (F), tyrosine (Y), tryptophan (W). Preferably the antibody according to the invention is characterized in that said amino acid residue having a smaller side chain volume is selected from the group consisting of alanine (A), serine (S), threonine (T), valine (V). Preferably the antibody according to the invention is characterized in that both CH3 domains are further altered by the introduction of cysteine (C) as amino acid in the corresponding positions of each CH3 domain. Preferably the antibody according to the invention is characterized in that one of the constant heavy chain domains CH3 of both heavy chains is replaced by a constant heavy chain domain CH1; and the other constant heavy chain domain CH3 is replaced by a constant light chain domain CL.

Preferably the antibody is further characterized in that the binding of said antibody to human BCMA is not reduced by 100 ng/ml APRIL and not reduced by 100 ng/ml BAFF for more than 15%, measured in said ELISA. Preferably the antibody is further characterized in that the binding of said antibody to human BCMA is not reduced by 1000 ng/ml APRIL and not reduced by 1000 ng/ml, for more than 20%, measured in said ELISA. Preferably the antibody is further characterized in that the binding of said antibody to human BCMA is not reduced by 1000 ng/ml, APRIL and not reduced by 1000 ng/ml BAFF for more than 15%, measured in said ELISA.

Preferably the antibody according to the invention does not alter APRIL-dependent NF-κB activation for more than 15%. Preferably the antibody according to the invention does not alter BAFF-dependent NF-κB activation for more than 15%. Preferably the antibody according to the invention does not alter NF-κB activation without APRIL and BAFF for more than 15%.

Preferably the antibody according to the invention is characterized in that its binding to BCMA is not reduced by APRIL and preferably not reduced by BAFF for more than 25%, preferably not more than 20%, preferably not more than 10%, measured as binding of said antibody in a concentration of 140 nM, preferably 50 nM, and preferably 5 nM to NCI-H929 cells (ATCC® CRL9068™) in presence or absence of APRIL or respectively BAFF in a concentration of 2.5 µg/ml compared to the binding of said antibody to NCI-H929 cells without APRIL or BAFF respectively.

Preferably the antibody according to the invention is further characterized in that it binds also specifically to cynomolgus BCMA.

A further embodiment of the invention is a method for the preparation of a bispecific antibody according to the invention comprising the steps of
- a) transforming a host cell with vectors comprising nucleic acid molecules encoding the light chain and heavy chain of an antibody specifically binding to the first target and vectors comprising nucleic acid molecules encoding the light chain and heavy chain of an antibody specifically binding to the second target, wherein the variable domains VL and VH or the constant domains CL and CH1 are replaced by each other;
- b) culturing the host cell under conditions that allow synthesis of said antibody molecule; and
- c) recovering said antibody molecule from said culture.

A further embodiment of the invention is a host cell comprising vectors comprising nucleic acid molecules encoding the light chain and heavy chain of an antibody specifically binding to the first target and vectors comprising nucleic acid molecules encoding the light chain and heavy chain of an antibody specifically binding to the second target, wherein the variable domains VL and VH or the constant domains CL and CH1 are replaced by each other.

A further preferred embodiment of the invention is a pharmaceutical composition comprising an antibody according to the invention and a pharmaceutically acceptable excipient.

A further embodiment of the invention is a diagnostic composition comprising an antibody according to the invention.

A further preferred embodiment of the invention is a pharmaceutical composition comprising an antibody according to the invention for use as a medicament. A further preferred embodiment of the invention is a pharmaceutical composition comprising an antibody according to the invention for use as a medicament in the treatment of plasma cell disorders. A further preferred embodiment of the invention is a pharmaceutical composition comprising an antibody according to the invention for use as a medicament in the treatment of Multiple Myeloma. A further embodiment of the invention is an antibody according to the invention for the treatment of plasma cell disorders like Multiple Myeloma MM or other B-cell disorders expressing BCMA. MM is a B-cell malignancy characterized by a monoclonal expansion and accumulation of abnormal plasma cells in the bone marrow compartment. MM also involves circulating clonal B cells with same IgG gene rearrangement and somatic hypermutation. MM arises from an asymptomatic, premalignant condition called monoclonal gammopathy of unknown significance (MGUS), characterized by low levels of bone marrow plasma cells and a monoclonal protein. MM cells proliferate at low rate. MM results from a progressive occurrence of multiple structural chromosomal changes (e.g. unbalanced translocations). MM involves the mutual interaction of malignant plasma cells and bone marrow microenvironment (e.g. normal bone marrow stromal cells). Clinical signs of active MM include monoclonal antibody spike, plasma cells overcrowding the bone marrow, lytic bone lesions and bone destruction resulting from overstimulation of osteoclasts (Dimopulos & Terpos, Ann Oncol 2010; 21 suppl 7: vii143-150). Another B-cell disorder involving plasma cells i.e. expressing BCMA is systemic lupus erythematosus (SLE), also known as lupus. SLE is a systemic, autoimmune disease that can affect any part of the body and is represented with the immune system attacking the body's own cells and tissue, resulting in chronic inflammation and tissue damage. It is a Type III hypersensitivity reaction in which antibody-immune complexes precipitate and cause a further immune response (Inaki & Lee, Nat Rev Rheumatol 2010; 6: 326-337). A further preferred embodiment of the invention is pharmaceutical composition comprising an antibody according to the invention for use as a medicament in the treatment of systemic lupus erythematosus.

In regard to bispecific antibodies against BCMA and CD3 the inventors recognize that a bispecific antibody against BCMA and capable of binding specifically to an activating T cell antigen (BCMA-TCB) which 1) is in an ELISA assay not reduced more than 20% in its binding to BCMA by APRIL concentrations relevant in patients with Multiple Myeloma, 2) preferably is in an ELISA assay not reduced by more than 20% in its binding to BCMA by BAFF concentrations relevant in patients with Multiple Myeloma, avoids that the efficacy of the BCMA-TCB to eradicate BCMA-positive tumor cells in MM patients is negatively affected by the concentration of APRIL and BAFF in the serum or at the tumor (see also FIGS. 1 and 2 and descriptions to FIGS. 1 and 2). In addition the inventors recognize that a bispecific antibody against BCMA and capable of binding specifically to an activating T cell antigen (BCMA-TCB) which 1) is in a H929 cell based flow cytometry assay not reduced more than 25% in its binding to BCMA by APRIL concentrations which can be relevant in patients with Multiple Myeloma, 2) preferably is in a H929 cell based flow cytometry assay not reduced more than 25% in its binding to BCMA by APRIL concentrations which can be relevant in patients with Multiple Myeloma, avoids that the efficacy of the BCMA-TCB to eradicate BCMA-positive tumor cells in MM patients is negatively affected by the concentration of APRIL and BAFF in the serum or at the tumor (see also FIGS. 1 and 2 and descriptions to FIGS. 1 and 2).

In addition, the inventors recognize that a bispecific antibody against BCMA and capable of binding specifically to an activating T cell antigen (BCMA-TCB) which 1) does not block or increase APRIL-dependent NF-κB activation, 2) preferably does not block or increase BAFF-dependent NF-κB activation, and 3) does not induce NF-κB activation without APRIL and preferably without BAFF avoids that the efficacy of the BCMA-TCB to eradicate BCMA-positive tumor cells in MM patients is negatively affected by the concentration of APRIL and BAFF in the serum or at the tumor. In addition as the BCMA-TCB does not induce NF-κB activation without APRIL and preferably without BAFF, activation and increase of survival of BCMA-positive resp. tumor cells does not occur in the case that the BCMA-TCB for whatever reasons does not kill the tumor cells, e.g. by not binding to CD3 but only to tumor cells. In addition receptor internalization may also not occur which could reduce the efficacy of BCMA-TCB.

Because efficacy of antibodies usually increases with tumor occupancy/concentration of TCB, the result with a BCMA-TCB without a BCMA antibody according to this invention could be of considerable inter-patient variability in efficacy (e.g. overall less efficacy, see also FIGS. 1 and 2).

In addition, in patients with high levels of serum APRIL and BAFF (e.g. multiple myeloma patients) it may not be required to increase the dose for an antibody according to this invention as it may not be affected by ligand competition. In contrast, the doses for other ligand-blocking/competing anti-BCMA antibodies may need to be increased in those patients.

Another advantage of the antibody according to the invention is an elimination half-life of about 1 to 12 days which allows at least once or twice/week administration. Preferably the antibody according to the invention is administered once or twice a week preferably via subcutaneous administration (e.g. preferably in the dose range of 0.25 to 2.5, preferably to 25 mg/m$^2$/week). Due to superior cytotoxicity activities of the antibody according to the invention it can be administered at least at the same magnitude of clinical dose range (or even lower) as compared to conventional monospecific antibodies or conventional bispecific antibodies that are not T cell bispecifics (i.e. do not bind to CD3 on one arm). It is envisaged that for an antibody according to the invention subcutaneous administration is preferred in the clinical settings (e.g. in the dose range of 1-100 mg/m$^2$/week).

According to the invention OD can be measured at 405 nm or 450 nm (preferably with the same relative results, comparison without APRIL or BAFF). According to the invention OD can be measured with human or murine APIL or BAFF 450 nm (preferably with the same relative results, comparison without APRIL or BAFF).

DESCRIPTION OF THE FIGURES

FIG. 9. Competition of anti-BCMA antibodies with Δ-APRIL after simultaneous incubation detected by flow cytometry. (A) The mean fluorescence intensity and the relative fluorescence signal (Alexa.Fluor 647 signal) of the anti-BCMA antibody clones 14B11, 13D2, 13A4, 17A5 and 83A10 at the concentration of 20 μg/mL in presence or absence of 2.5 μg/mL Δ-APRIL or (B) the mean fluorescence intensity and the relative fluorescence signal of Δ-APRIL (FITC signal) at a concentration of 2.5 μg/mL Δ-APRIL and the anti-BCMA antibody clone 83A10 (20 μg/mL) (Alexa.Fluor 647 signal) were measured. Detection of anti-BCMA antibody in presence of Δ-APRIL with FITC conjugated anti-human Fc antibody was normalized to the signal of anti-BCMA antibody clone in absence Δ-APRIL. Detection of Δ-APRIL in presence of the anti-BCMA antibody clone with Alexa.Fluor 647 conjugated anti-HA antibody was normalized to Δ-APRIL signal in presence of the isotype control.

DETAILED DESCRIPTION OF THE INVENTION

Figure 1:
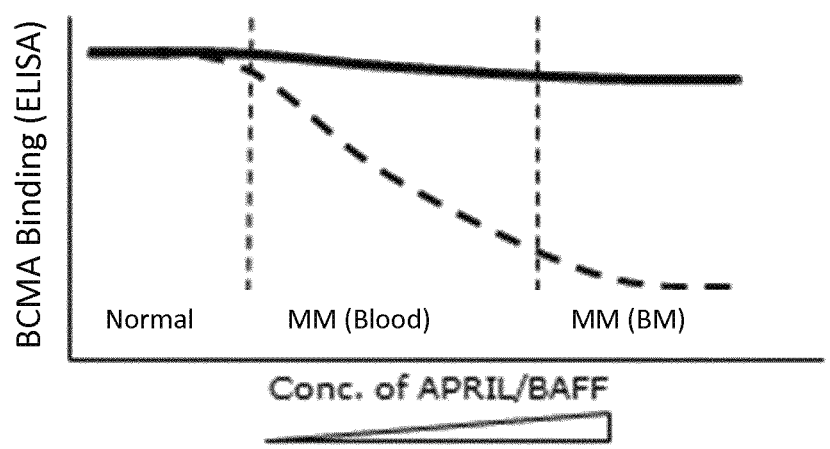
FIG. 1. Superior binding properties of a non-ligand blocking/non-competing anti-BCMA antibody vs. a ligand-blocking/competing anti-BCMA antibody; or a non-ligand blocking/non-competing anti-BCMA containing TCB vs. a ligand-blocking/competing anti-BCMA containing TCB on plate-bound-BCMA cells by ELISA. In this graph, increasing concentrations (i.e. 10, 100, 1000 ng/mL) of soluble APRIL or BAFF representative of the levels found in the blood and bone marrow of multiple myeloma patients does not alter the binding of a non-ligand blocking/non-competing anti-BCMA antibody or non-ligand blocking/non-competing anti-BCMA containing TCB to plate-bound-BCMA (continuous line). In contrast, the high concentrations (i.e. 100 ng/mL to 1000 ng/mL) of soluble APRIL or BAFF representative of the levels found in the blood and bone marrow of multiple myeloma patients reduce the binding of a ligand blocking/competing anti-BCMA antibody or ligand blocking/competing anti-BCMA containing TCB to plate-bound-BCMA (dotted line). The concentration of anti-BCMA antibodies or anti-BCMA containing TCB with different properties is preferably concentration(s) ranging from 0.1 pM to 200 nM as the levels of add-on circulating APRIL or BAFF range from 1 ng/mL (healthy normal) to 100 ng/mL (MM, blood) and beyond (MM, tumor in bone marrow).

The term "BCMA" as used herein relates to human B cell maturation target, also known as BCMA; TR17_HUMAN, TNFRSF17 (UniProt Q02223), which is a member of the tumor necrosis receptor superfamily that is preferentially expressed in differentiated plasma cells. The extracellular domain of BCMA consists according to UniProt of amino acids 1-54 (or 5-51). The term "antibody against BCMA, anti BCMA antibody" as used herein relates to an antibody specifically binding to BCMA.

The term "CD3ε or CD3" as used herein relates to human CD3ε described under UniProt P07766 (CD3E_HUMAN). The term "antibody against CD3, anti CD3 antibody" relates to an antibody binding to CD3ε. Preferably the antibody comprises a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3. Preferably the antibody comprises the variable domains of SEQ ID NO:7 (VH) and SEQ ID NO:8 (VL). The term "antibody against CD3, anti CD3 antibody" as used herein relates to an antibody specifically binding to CD3.

"Specifically binding to CD3 or BCMA" refer to an antibody that is capable of binding CD3 or BCMA (the targets) with sufficient affinity such that the antibody is useful as a therapeutic agent in targeting CD3 or BCMA. In some embodiments, the extent of binding of an anti-CD3 or BCMA antibody to an unrelated, non-CD3 or non-BCMA protein is about 10-fold preferably >100-fold less than the binding of the antibody to CD3 or BCMA as measured, e.g., by surface plasmon resonance (SPR) e.g. Biacore®, enzyme-linked immunosorbent (ELISA) or flow cytometry (FACS). Preferably the antibody that binds to CD3 or BCMA has a dissociation constant (Kd) of $10^{-8}$ M or less, preferably from $10^{-8}$ M to $10^{-13}$ M, preferably from $10^{-9}$ M to $10^{-13}$ M. Preferably the anti-CD3 and/or anti-BCMA antibody binds to an epitope of CD3 and/or BCMA that is conserved among CD3 and/or BCMA from different species, preferably among human and cynomolgus. "Bispecific antibody specifically binding to CD3 and BCMA" or "antibody according to the invention" refers to a respective definition for binding to both targets. An antibody specifically binding to BCMA (or BCMA and CD3) does not bind to other human antigens. Therefore in an ELISA, OD values for such unrelated targets will be equal or lower to that of the limit of detection of the specific assay, preferably >0.3 ng/mL, or equal or lower to OD values of control samples without plate-bound-BCMA or with untransfected HEK293 cells.

The term "APRIL" as used herein relates to recombinant, truncated murine APRIL (amino acids 106-241; NP_076006). APRIL can be produced as described in Ryan, 2007 (Mol Cancer Ther; 6 (11): 3009-18).

The term "BAFF" as used herein relates to recombinant, truncated human BAFF (UniProt Q9Y275 (TN13B_HUMAN) which can be produced as described in Gordon, 2003 (Biochemistry; 42 (20): 5977-5983). Preferably a His-tagged BAFF is used according to the invention. Preferably the His-tagged BAFF is produced by cloning a DNA fragment encoding BAFF residues 82-285 into an expression vector, creating a fusion with an N-terminal His-tag followed by a thrombin cleavage site, expressing said vector and cleaving the recovered protein with thrombin.

Anti-BCMA antibodies are analyzed by ELISA for binding to human BCMA using plate-bound BCMA in the presence and absence of APRIL and/or BAFF. For this assay, an amount of plate-bound BCMA preferably 1.5 μg/mL and concentration(s) preferably ranging from 1 pM to 200 nM of anti-BCMA antibody are used. A BCMA antibody for which its BCMA binding is not inhibited according to the invention is an anti-BCMA antibody "not inhibiting the binding of APRIL and/or BAFF to human BCMA in an ELISA assay".

The term "NF-κB" as used herein relates to recombinant NF-κB p50 (accession number (P19838).

NF-κB activity is measured by a DNA-binding ELISA of an extract of NCI-H929 MM cells (CRL-9068™). NCI-H929 MM cells, untreated or treated with 0.1 μg/mL TNF-α, 100 ng/mL heat-treated HT-truncated-BAFF, 100 ng/mL truncated-BAFF, 0.1 pM to 200 nM isotype control, and with or without 0.1 pM to 200 nM of anti-BCMA antibodies are incubated for 20 min NF-κB activity is assayed using a functional ELISA that detects chemiluminescent signal from p65 bound to the NF-κB consensus sequence (U.S. Pat. No. 6,150,090).

An antibody that does not block APRIL-dependent NF-κB activation for more than 20% and does not reduce APRIL-dependent NF-κB activation for more than 20% and does not increase APRIL-dependent NF-κB activation for more than 20% is considered "not to alter APRIL-dependent NF-κB activation" for more than 20% as compared to APRIL-induced NF-κB activation without an antibody according to the invention (control group); 20% representing the mean standard variability between experiments. Preferably an antibody according to the invention does not alter APRIL-dependent NF-κB activation for more than 15%.

An antibody that does not block BAFF-dependent NF-κB activation for more than 20% and does not reduce BAFF-dependent NF-κB activation for more than 20% and does not increase BAFF-dependent NF-κB activation for more than 20% is considered "not to alter BAFF-dependent NF-κB activation" for more than 20% as compared to BAFF-induced NF-κB activation without an antibody according to the invention (control group); 20% representing the mean standard variability between experiments. Preferably an antibody according to the invention does not alter BAFF-dependent NF-κB activation for more than 15%.

An antibody that does not block NF-κB activation without APRIL and BAFF for more than 20% and does not reduce NF-κB activation without APRIL and BAFF for more than 20% and does not increase NF-κB activation without APRIL and BAFF for more than 20% is considered "not to alter NF-κB activation without APRIL and BAFF" for more than 20% as compared to APRIL-induced NF-κB activation without an antibody according to the invention (control group); 20% representing the mean standard variability between experiments. Preferably an antibody according to the invention does not alter NF-κB activation without APRIL and BAFF for more than 15%.

Also if an antibody according to the invention is used in large excess, preferably up to 500 nM or 1000 nM binding of said antibody is not reduced by 100 ng/ml APRIL and preferably by BAFF for more than 20% and does not alter APRIL-dependent NF-κB activation for more than 20%, with and without APRIL and preferably with and without BAFF for more than 20%.

The term "target" as used herein means either BCMA or CD3. The term "first target and second target" means either CD3 as first target and BCMA as second target or means BCMA as first target and CD3 as second target.

The term "antibody" as used herein refers to a monoclonal antibody. An antibody consists of two pairs of a "light chain" (LC) and a "heavy chain" (HC) (such light chain (LC)/heavy chain pairs are abbreviated herein as LC/HC). The light chains and heavy chains of such antibodies are polypeptides consisting of several domains. Each heavy chain comprises a heavy chain variable region (abbreviated herein as HCVR or VH) and a heavy chain constant region. The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain VL and a light chain constant domain CL. The variable domains VH and VL can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The "constant domains" of the heavy chain and of the light chain are not involved directly in binding of an antibody to a target, but exhibit various effector functions.

The term "antibody" includes e.g. mouse antibodies, human antibodies, chimeric antibodies, humanized antibodies and genetically engineered antibodies (variant or mutant antibodies) as long as their characteristic properties are retained. Especially preferred are human or humanized antibodies, especially as recombinant human or humanized antibodies.

The terms "bispecific antibody" and "antibody according to the invention" as used herein refer to an antibody in which one of the two pairs of heavy chain and light chain (HC/LC) is specifically binding to CD3 and the other one is specifically binding to BCMA.

There are five types of mammalian antibody heavy chains denoted by the Greek letters: α, δ, ε, γ, and μ (Janeway C A, Jr et al (2001). Immunobiology. 5th ed., Garland Publishing). The type of heavy chain present defines the class of antibody; these chains are found in IgA, IgD, IgE, IgG, and IgM antibodies, respectively (Rhoades R A, Pflanzer R G (2002). Human Physiology, 4th ed., Thomson Learning). Distinct heavy chains differ in size and composition; α and γ contain approximately 450 amino acids, while μ and ε have approximately 550 amino acids. Each heavy chain has two regions, the constant region and the variable region. The constant region is identical in all antibodies of the same isotype, but differs in antibodies of different isotype. Heavy chains γ, α and δ have a constant region composed of three constant domains CH1, CH2, and CH3 (in a line), and a hinge region for added flexibility (Woof J, Burton D Nat Rev Immunol 4 (2004) 89-99); heavy chains μ and ε have a constant region composed of four constant domains CH1, CH2, CH3, and CH4 (Janeway C A, Jr et al (2001). Immunobiology. 5th ed., Garland Publishing). The variable region of the heavy chain differs in antibodies produced by different B cells, but is the same for all antibodies produced by a single B cell or B cell clone. The variable region of each heavy chain is approximately 110 amino acids long and is composed of a single antibody domain.

In mammals there are only two types of light chain, which are called lambda (λ) and kappa (κ). A light chain has two successive domains: one constant domain CL and one variable domain VL. The approximate length of a light chain is 211 to 217 amino acids. Preferably the light chain is a kappa (κ) light chain, and the constant domain CL is preferably derived from a kappa (K) light chain (the constant domain CK).

The terms "monoclonal antibody" or "monoclonal antibody composition" as used herein refer to a preparation of antibody molecules of a single amino acid composition.

The "antibodies" according to the invention can be of any class (e.g. IgA, IgD, IgE, IgG, and IgM, preferably IgG or IgE), or subclass (e.g., IgG1, IgG2, IgG3, IgG4, IgA1 and IgA2, preferably IgG1), whereby both antibodies, from which the bivalent bispecific antibody according to the invention is derived, have an Fc part of the same subclass (e.g. IgG1, IgG4 and the like, preferably IgG1), preferably of the same allotype (e.g. Caucasian).

A "Fab fragment of an antibody" as used herein is a fragment on an antibody that binds to antigens. It is composed of one constant and one variable domain of each of the heavy chain (CH1 and VH) and the light chain (CL and VL). According to the invention the domains of the heavy and light chain of a Fab fragment are not chemically linked together and are therefore no scFvs (single chain variable fragments).

A "Fc part of an antibody" is a term well known to the skilled artisan and defined on the basis of papain cleavage of antibodies. The antibodies according to the invention contain as Fc part, preferably a Fc part derived from human origin and preferably all other parts of the human constant regions. The Fc part of an antibody is directly involved in complement activation, C1q binding, C3 activation and Fc receptor binding. While the influence of an antibody on the complement system is dependent on certain conditions, binding to C1q is caused by defined binding sites in the Fc part. Such binding sites are known in the state of the art and described e.g. by Lukas, T J., et al., J. Immunol. 127 (1981) 2555-2560; Brunhouse, R., and Cebra, J. J., MoI. Immunol. 16 (1979) 907-917; Burton, D. R., et al., Nature 288 (1980) 338-344; Thommesen, J. E., et al., MoI. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation, C1q binding and C3 activation, whereas IgG4 do not activate the complement system, do not bind C1q and do not activate C3. Preferably the Fc part is a human Fc part. Preferably the Fc part is a human IgG1Fc part.

Preferably the antibody according to the invention comprises as Fc part an Fc variant of a wild-type human IgG Fc region, said Fc variant comprising an amino acid substitution at position Pro329 and at least one further amino acid substitution, wherein the residues are numbered according to the EU index of Kabat, and wherein said antibody exhibits a reduced affinity to the human FcγRIIIA and/or FcγRIIA and for FcγRI compared to an antibody comprising the wildtype IgG Fc region, and wherein the ADCC induced by said antibody is reduced to at least 20% of the ADCC induced by the antibody comprising a wild-type human IgG Fc region. In a specific embodiment Pro329 of a wild-type human Fc region in the antibody according to the invention is substituted with glycine or arginine or an amino acid residue large enough to destroy the proline sandwich within the Fc/Fcγ receptor interface, that is formed between the proline329 of the Fc and tryptophane residues Trp 87 and Tip 110 of FcγRIII (Sondermann et al.: Nature 406, 267-273 (20 Jul. 2000)). In a further aspect of the invention the at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region. Such Fc variants are described in detail in WO2012130831.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the targets noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon target challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH)) as used herein denotes each of the pair of light and heavy chains which is involved directly in binding the antibody to the target. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the target binding site. The antibody heavy and light chain CDR3 regions play a particularly important role in the binding specificity/affinity of the antibodies according to the invention and therefore provide a further object of the invention.

The terms "hypervariable region" or "target-binding portion of an antibody" when used herein refer to the amino acid residues of an antibody which are responsible for target-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to target binding. CDR and FR regions are determined according to the standard definition of Kabat et al., Sequences of Proteins of Immunological Interest, 5th ed., Public Health Service, National Institutes of Health, Bethesda, Md. (1991).

The constant heavy chain domain CH1 by which the heavy chain domain CH3 is replaced can be of any Ig class (e.g. IgA, IgD, IgE, IgG, and IgM), or subclass (e.g., IgG1, IgG2, IgG3, IgG4, IgA1 and IgA2). The constant light chain domain CL by which the heavy chain domain CH3 is replaced can be of the lambda ($\lambda$) or kappa ($\kappa$) type, preferably the kappa ($\kappa$) type.

The term "target" or "target molecule" as used herein are used interchangeable and refer to human BCMA and human CD3ε.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of a target that is bound by an antibody.

In general there are two vectors encoding the light chain and heavy chain of said antibody specifically binding to the first target, and further two vectors encoding the light chain and heavy chain of said antibody specifically binding to the second target. One of the two vectors is encoding the respective light chain and the other of the two vectors is encoding the respective heavy chain. However in an alternative method for the preparation of a bispecific antibody according to the invention, only one first vector encoding the light chain and heavy chain of the antibody specifically binding to the first target and only one second vector encoding the light chain and heavy chain of the antibody specifically binding to the second target can be used for transforming the host cell.

The term "nucleic acid or nucleic acid molecule", as used herein, is intended to include DNA molecules and RNA molecules. A nucleic acid molecule may be single-stranded or double-stranded, but preferably is double-stranded DNA.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen S N, et al, PNAS 1972, 69 (8): 2110-2114.

Recombinant production of antibodies using transformation is well-known in the state of the art and described, for example, in the review articles of Makrides, S. C, Protein Expr. Purif. 17 (1999) 183-202; Geisse, S., et al., Protein Expr. Purif. 8 (1996) 271-282; Kaufman, R J., Mol. Biotechnol. 16 (2000) 151-161; Werner, R. G., et al., Arzneimittelforschung 48 (1998) 870-880 as well as in U.S. Pat. No. 6,331,415 and U.S. Pat. No. 4,816,567.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The bispecific antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NSO cells, SP2/0 cells, HEK293 cells, COS cells, yeast, or E. coli cells, and the antibody is recovered from the cells (supernatant or cells after lysis). The bispecific antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed., Current Protocols in Molecular Biology, Greene Publishing and Wiley Interscience, New York (1987).

Expression in NSO cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA or RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and target binding, but may improve the yield of the recombinant production, protein stability or facilitate the purification.

T cell bispecific (TCB) binders have very high concentration/tumor-cell-receptor-occupancy dependent potency in cell killing (e.g. $EC_{50}$ in in vitro cell killing assays in the sub- or low picomolar range; Dreier et al. Int J Cancer 2002), T-cell bispecific binder (TCB) are given at much lower doses than conventional monospecific antibodies. For example, blinatumomab (CD19×CD3) is given at a continuous intravenous dose of 5 to 15 $\mu g/m^2$/day (i.e. only 0.35 to 0.105 $mg/m^2$/week) for treatment of acute lymphocytic leukemia or 60 $\mu g/m^2$/day for treatment of Non Hodgkin Lymphoma, and the serum concentrations at these doses are in the range of 0.5 to 4 ng/ml (Klinger et al., Blood 2012; Topp et al., J Clin Oncol 2011; Goebeler et al. Ann Oncol 2011). Because low doses of TCB can exert high efficacy in patients, it is envisaged that for an antibody according to the invention subcutaneous administration is possible and preferred in the clinical settings (preferably in the dose range of 0.25 to 2.5 $mg/m^2$/week). Even at these low concentrations/doses/receptor occupancies, TCB can cause considerable adverse events (Klinger et al., Blood 2012). Therefore it is critical to control tumor cell occupancy/coverage. In patients with high and variable levels of serum APRIL and BAFF (e.g. multiple myeloma patients, Moreaux et al. 2004; Blood 103(8): 3148-3157) number of TCB bound to the tumor cells resp. tumor cell occupancy may be considerably influenced by APRIL/BAFF. But by using said antibody of this invention, tumor cell occupancy respectively efficacy/safety it may not be required to increase the dose for an antibody according to this invention as said antibody may not be affected by APRIL/BAFF ligand competition. Another advantage of the antibody according to the invention is based on the inclusion of an Fc portion, which increases the elimination half-life to ~12 days and allows at least once or twice/week administrations as compared to TCBs without an Fc portion (e.g. blinatumomab) which are required to be given intravenously and continuously with a pump carried by patients.

TABLE 1

Antibody sequences

| BCMA antibody | SEQ ID NO: | | | | | | | |
|---|---|---|---|---|---|---|---|---|
| | VH | VL | CDR1H | CDR2H | CDR3H | CDR1L | CDR2L | CDR3L |
| 13C2 | 17 | 27 | 37 | 47 | 57 | 67 | 77 | 87 |
| 17A5 | 18 | 28 | 38 | 48 | 58 | 68 | 78 | 88 |
| 83A10 | 19 | 29 | 39 | 49 | 59 | 69 | 79 | 89 |
| 13A4 | 20 | 30 | 40 | 50 | 60 | 70 | 80 | 90 |
| 13D2 | 21 | 31 | 41 | 51 | 61 | 71 | 81 | 91 |
| 14B11 | 22 | 32 | 42 | 52 | 62 | 72 | 82 | 92 |
| 14E1 | 23 | 33 | 43 | 53 | 63 | 73 | 83 | 93 |
| 29B11 | 24 | 34 | 44 | 54 | 64 | 74 | 84 | 94 |
| 29F3 | 25 | 35 | 45 | 55 | 65 | 75 | 85 | 95 |
| 13A7 | 26 | 36 | 46 | 56 | 66 | 76 | 86 | 96 |

The following examples, sequence listing and figures are provided to aid the understanding of the present invention, the true scope of which is set forth in the appended claims. It is understood that modifications can be made in the procedures set forth without departing from the spirit of the invention.

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, 5th ed., NIH Publication No. 91-3242.

Gene Synthesis

Desired gene segments are prepared from oligonucleotides made by chemical synthesis. The 600-1800 bp long gene segments, which are flanked by singular restriction endonuclease cleavage sites, are assembled by annealing and ligation of oligonucleotides including PCR amplification and subsequently cloned via the indicated restriction sites e.g. Kpnl/Sad or Ascl/Pacl into a pPCRScript (Stratagene) based pGA4 cloning vector. The DNA sequences of the subcloned gene fragments are confirmed by DNA sequencing. Gene synthesis fragments are ordered according to given specifications at Geneart (Regensburg, Germany).

DNA Sequence Determination

DNA sequences were determined by double strand sequencing.

DNA and Protein Sequence Analysis and Sequence Data Management

The GCG's (Genetics Computer Group, Madison, Wis.) software package version 10.2 and Infomax's Vector NT1 Advance suite version 8.0 is used for sequence creation, mapping, analysis, annotation and illustration.

Expression Vectors a) For the expression of the described antibodies variants of expression plasmids for transient expression (e.g. in HEK293 EBNA or HEK293-F) cells based either on a cDNA organization with a CMV-Intron A promoter or on a genomic organization with a CMV promoter are applied. Beside the antibody expression cassette the vectors contain an origin of replication which allows replication of this plasmid in E. coli, and—a β-lactamase gene which confers ampicillin resistance in E. coli. The transcription unit of the antibody gene is composed of the following elements:

unique restriction site(s) at the 5' end—the immediate early enhancer and promoter from the human cytomegalovirus,
followed by the Intron A sequence in the case of the cDNA organization,
a 5'-untranslated region of a human antibody gene,
a immunoglobulin heavy chain signal sequence,
the human antibody chain (wildtype or with domain exchange) either as cDNA or as genomic organization with an the immunoglobulin exon-intron organization
a 3' untranslated region with a polyadenylation signal sequence, and
unique restriction site(s) at the 3' end.

The fusion genes comprising the described antibody chains as described below are generated by PCR and/or gene synthesis and assembled with known recombinant methods and techniques by connection of the according nucleic acid segments e.g. using unique restriction sites in the respective vectors. The subcloned nucleic acid sequences are verified by DNA sequencing. For transient transfections larger quantities of the plasmids are prepared by plasmid preparation from transformed E. coli cultures (Nucleobond AX, Macherey-Nagel).

b) Generation of Antibody and Antigen Expression Vectors

The variable region of heavy and light chain DNA sequences were subcloned in frame with either the human IgG1 constant heavy chain or the hum IgG1 constant light chain pre-inserted into the respective recipient mammalian expression vector. The antibody expression was driven by a chimeric MPSV promoter comprising a CMV enhancer and a MPSV promoter followed by a 5' UTR, an intron and a kappa MAR element. The transcription is terminated by a synthetic polyA signal sequence at the 3' end of the CDS. All vectors carry a 5'-end DNA sequence coding for a leader peptide which targets proteins for secretion in eukaryotic cells. In addition each vector contains an EBV OriP sequence for episomal plasmid replication in EBV EBNA expressing cells.

The antigens that have been used for the phage display selection campaigns and to characterize the binding properties of the selected antibodies were expressed from mammalian antigen expression vectors with pre-inserted DNA sequences coding for C-terminal tags. An Avi tag has been used for in vivo or in vitro biotinylation of the respective antigen. For purification and homo- or heterodimerization of the antigen a hum IgG1 Fc wt or Fc knob was fused to the C-terminus of the antigen expression cassette. The antigen expression was driven by a chimeric MPSV promoter comprising a CMV enhancer and a MPSV promoter followed by a 5' UTR, an intron and a kappa MAR element. The transcription was terminated by a synthetic polyA signal sequence at the 3' end of the CDS. All vectors carry a 5'-end DNA sequence coding for a leader peptide which targets proteins for secretion in eukaryotic cells. In addition each vector contains an EBV OriP sequence for episomal plasmid replication in EBV EBNA expressing cells.

Cell Culture Techniques

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Expression in HEK293 Cells

Bispecific antibodies are expressed by transient co-transfection of the respective expression plasmids in adherently growing HEK293-EBNA or in HEK293-F cells growing in suspension as described below.

a) Transient Transfections in HEK293-EBNA System

Bispecific antibodies are expressed by transient co-transfection of the respective expression plasmids (e.g. encoding the heavy and modified heavy chain, as well as the corresponding light and modified light chain) in adherently growing HEK293-EBNA cells (human embryonic kidney cell line 293 expressing Epstein-Barr-Virus nuclear target; American type culture collection deposit number ATCC #CRL-10852, Lot. 959 218) cultivated in DMEM (Dulbecco's modified Eagle's medium, Gibco) supplemented with 10% Ultra Low IgG FCS (fetal calf serum, Gibco), 2 mM L-Glutamine (Gibco), and 250 µg/ml Geneticin (Gibco). For transfection FuGENE™ 6 Transfection Reagent (Roche Molecular Biochemicals) is used in a ratio of FuGENE™ reagent (µl) to DNA (µg) of 4:1 (ranging from 3:1 to 6:1). Proteins are expressed from the respective plasmids using a molar ratio of (modified and wildtype) light chain and heavy chain encoding plasmids of 1:1 (equimolar) ranging from 1:2 to 2:1, respectively. Cells are feeded at day 3 with L-Glutamine ad 4 mM, Glucose [Sigma] and NAA [Gibco]. Bispecific antibody containing cell culture supernatants are harvested from day 5 to 11 after transfection by centrifugation and stored at −200 C. General information regarding the recombinant expression of human immunoglobulins in e.g. HEK293 cells is given in: Meissner, P. et al., Biotechnol. Bioeng. 75 (2001) 197-203.

b) Transient Transfections in HEK293-F System

Bispecific antibodies are generated by transient transfection of the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serumfree FreeStyle 293 expression medium (Invitrogen) are transfected with a mix of the four expression plasmids and 293fectin or fectin (Invitrogen). For 2 L shake flask (Corning) HEK293-F cells are seeded at a density of $1.0 \times 10^6$ cells/mL in 600 mL and incubated at 120 rpm, 8% CO2. The day after the cells are transfected at a cell density of ca. $1.5 \times 10^6$ cells/mL with ca. 42 mL mix of A) 20 mL Opti-MEM (Invitrogen) with 600 μg total plasmid DNA (1 μg/mL) encoding the heavy or modified heavy chain, respectively and the corresponding light chain in an equimolar ratio and B) 20 ml Opti-MEM+1.2 mL 293 fectin or fectin (2 μl/mL). According to the glucose consumption glucose solution is added during the course of the fermentation. The supernatant containing the secreted antibody is harvested after 5-10 days and antibodies are either directly purified from the supernatant or the supernatant is frozen and stored.

Protein Determination

The protein concentration of purified antibodies and derivatives is determined by determining the optical density (OD) at 280 nm, using the molar extinction coefficient calculated on the basis of the amino acid sequence according to Pace et al., Protein Science, 1995, 4, 2411-1423.

Antibody Concentration Determination in Supernatants

The concentration of antibodies and derivatives in cell culture supernatants is estimated by immunoprecipitation with Protein A Agarose-beads (Roche). 60 μL Protein A Agarose beads are washed three times in TBS-NP40 (50 mM Tris, pH 7.5, 150 mM NaCl, 1% Nonidet-P40). Subsequently, 1-15 mL cell culture supernatant is applied to the Protein A Agarose beads pre-equilibrated in TBS-NP40. After incubation for at 1 h at room temperature the beads are washed on an Ultrafree-MC-filter column (Amicon] once with 0.5 mL TBS-NP40, twice with 0.5 mL 2× phosphate buffered saline (2×PBS, Roche) and briefly four times with 0.5 mL 100 mM Na-citrate pH 5.0. Bound antibody is eluted by addition of 35 μl NuPAGE® LDS Sample Buffer (Invitrogen). Half of the sample is combined with NuPAGE® Sample Reducing Agent or left unreduced, respectively, and heated for 10 min at 70° C. Consequently, 5-30 μl are applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants is quantitatively measured by affinity HPLC chromatography. Briefly, cell culture supernatants containing antibodies and derivatives that bind to Protein A are applied to an Applied Biosystems Poros A/20 column in 200 mM $KH_2PO_4$, 100 mM sodium citrate, pH 7.4 and eluted from the matrix with 200 mM NaCl, 100 mM citric acid, pH 2.5 on an Agilent HPLC 1100 system. The eluted protein is quantified by UV absorbance and integration of peak areas. A purified standard IgG1 antibody served as a standard.

Alternatively, the concentration of antibodies and derivatives in cell culture supernatants is measured by Sandwich-IgG-ELISA. Briefly, StreptaWell High Bind Strepatavidin A-96 well microtiter plates (Roche) are coated with 100 μL/well biotinylated anti-human IgG capture molecule F(ab')2<h-Fcγ> BI (Dianova) at 0.1 μg/mL for 1 h at room temperature or alternatively over night at 4° C. and subsequently washed three times with 200 μL/well PBS, 0.05% Tween® (PBST, Sigma). 100 μL/well of a dilution series in PBS (Sigma) of the respective antibody containing cell culture supernatants is added to the wells and incubated for 1-2 h on a micro titerplate shaker at room temperature. The wells are washed three times with 200 μL/well PBST and bound antibody is detected with 100 μl F(ab')2<hFcγ>POD (Dianova) at 0.1 μg/mL as detection antibody for 1-2 h on a microtiterplate shaker at room temperature. Unbound detection antibody is washed away three times with 200 μL/well PBST and the bound detection antibody is detected by addition of 100 μL ABTS/well. Determination of absorbance is performed on a Tecan Fluor Spectrometer at a measurement wavelength of 405 nm (reference wavelength 492 nm).

Protein Purification

Proteins are purified from filtered cell culture supernatants referring to standard protocols. In brief, antibodies are applied to a Protein A Sepharose column (GE healthcare) and washed with PBS. Elution of antibodies is achieved at pH 2.8 followed by immediate neutralization of the sample. Aggregated protein is separated from monomeric antibodies by size exclusion chromatography (Superdex 200, GE Healthcare) in PBS or in 20 mM Histidine, 150 mM NaCl pH 6.0. Monomeric antibody fractions are pooled, concentrated if required using e.g. a MILLIPORE Amicon Ultra (30 MWCO) centrifugal concentrator, frozen and stored at −20° C. Part of the samples are provided for subsequent protein analytics and analytical characterization e.g. by SDS-PAGE, size exclusion chromatography or mass spectrometry.

SDS-PAGE

The NuPAGE® Pre-Cast gel system (Invitrogen) is used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer is used.

Analytical Size Exclusion Chromatography

Size exclusion chromatography for the determination of the aggregation and oligomeric state of antibodies is performed by HPLC chromatography. Briefly, Protein A purified antibodies are applied to a Tosoh TSKgel G3000SW column in 300 mM NaCl, 50 mM $KH_2PO_4/K_2HPO_4$, pH 7.5 on an Agilent HPLC 1100 system or to a Superdex 200 column (GE Healthcare) in 2×PBS on a Dionex HPLC-System. The eluted protein is quantified by UV absorbance and integration of peak areas. BioRad Gel Filtration Standard 151-1901 served as a standard.

Mass Spectrometry

The total deglycosylated mass of crossover antibodies is determined and confirmed via electrospray ionization mass spectrometry (ESI-MS). Briefly, 100 μg purified antibodies are deglycosylated with 50 mil N-Glycosidase F (PNGaseF, ProZyme) in 100 mM $KH_2PO_4/K_2HPO_4$, pH 7 at 37° C. for 12-24 h at a protein concentration of up to 2 mg/ml and subsequently desalted via HPLC on a Sephadex G25 column (GE Healthcare). The mass of the respective heavy and light chains is determined by ESI-MS after deglycosylation and reduction. In brief, 50 μg antibody in 115 μl are incubated with 60 μl IM TCEP and 50 μl 8 M Guanidine-hydrochloride subsequently desalted. The total mass and the mass of the reduced heavy and light chains is determined via ESI-MS on a Q-Star Elite MS system equipped with a NanoMate® source.

EXAMPLES

Example 1—Generation of Anti-BCMA Antibodies

Example 1A. Production of Antigens and Tool Reagents

Example 1A1. Recombinant, Soluble, Human BCMA Extracellular Domain a) Recombinant, soluble, human BCMA extracellular domain ("BCMA ECD") is produced as described in Ryan, 2007 (Mol Cancer Ther; 6 (11): 3009-18). Briefly, the human BCMA extracellular domain (ECD; amino acids 5-51; NP_001183) is amplified with forward primer 5-AAGCTT GGATCCATGTTGCAGATGGCTGGGCAGTGCTCC-3 (SEQ ID NO:11) incorporating a BamH1 site (bold, underlined) and reverse primer 5-GAATTC GCGGCCGCTCATCCTTTCACTGAATTGGTCACACTTGCA-3 (SEQ ID NO:12) incorporating a stop codon (italic) and NotI site (bold, underlined) using IMAGE clone 687194 (Invitrogen) as a PCR template. The PCR product is cloned into an expression vector comprising a glutathione S-transferase gene upstream of glutathione S-transferase (GST), transformed into an E. coli strain comprising T7 RNA polymerase gene under the control of the lacUV5 promoter and the induced protein is purified at 4° C. on an ÄKTA-explorer (GE Healthcare). The cell pellet is lysed in 1:15 w/v of B-PER buffer (Pierce) containing protease inhibitor and lysozyme. The extract is supplemented with 1 to 2 μg/mL DNase I (Sigma), stirred for an additional 20 min, and adjusted to pH 7.5. The soluble fusion protein is collected after centrifugation at 31,000×g for 20 min (Beckman) and loaded onto a glutathione Sepharose 4 FF column (GE Healthcare) preequilibrated with B-PER buffer. The column is washed with 4 column volumes (CV) B-PER buffer, 3 CV each of wash buffers 1 and 2 (Pierce), followed by a final column wash with 5 CV 50 mmol/L Tris (pH 8.0), 0.15 mol/L NaCl. The GST-tagged BCMA is eluted with 20 mmol/L reduced glutathione in 50 mmol/L Tris (pH 8.0) and dialyzed against PBS (pH 7.4) using a 3500 MWCO slide-A-lyzer (Pierce). For GST tag removal, BCMA:GST is treated with thrombin in 50 mmol/L Tris (pH 8.0), 0.15 mol/L NaCl, while bound to the glutathione Sepharose. Released thrombin is then captured by a benzamidine Sepharose column (GE Healthcare). The GST-cleaved BCMA is eluted from the column with 3 to 5 CV 50 mmol/L Tris (pH 8.0), 0.15 mol/L NaCl, and dialyzed against PBS (pH 7.4). Thrombin removal is confirmed by analyzing fractions for thrombin activity using the chromogenic substrate S-2238 (Chromogenix, DiaPharma). Protein concentration is determined by A280. All purified proteins are analyzed by SDS-PAGE and by TSK-Gel G3000SW HPLC size exclusion chromatography (Tosoh Bioscience).

A biotinylated variant of BCMA ECD ("BCMA-ECD-biot") is produced as described above using the same procedures with the following modifications. A DNA sequence encoding an Avi-His tag is added, via PCR amplification, in frame downstream at the 3' end of the first PCR product described above. This new, second PCR product is then subcloned into the pGEX4T1 expression vector and then co-transformed in bacteria together with a vector for expression of BirA enzyme for in vivo biotinylation of the Avi tag. The remaining production and purification steps are performed as indicated above for BCMA-ECD.

b) The extracellular domains of human, cynomolgus and murine BCMA that were used as antigens for phage display selections were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). The extracellular domains of human, cynomolgus and murine BCMA comprised methionine 4 to asparagine 53, methionine 4 to asparagine 52, and alanine 2 to threonine 49, respectively. These were N-terminally fused to the hinge of a human IgG1 enabling heterodimerization with an unfused human IgG1 Fc portion (hole chain) by knobs-into-holes technology.

Example 1A2. Recombinant, Truncated Murine APRIL a) Recombinant, truncated murine APRIL is produced as described in Ryan, 2007 (Mol Cancer Ther; 6 (11): 3009-18). Briefly, murine APRIL (residues 106-241; NP_076006) is amplified from IMAGE clone 5290965 (Invitrogen) and cloned into a bacterial expression vector fused at the COOH terminus to Gene-specific forward primer 5-ACGTT AGATCTCCACTCAGTCCTGCATCTTGTTCCAGTTAAC-3 (SEQ ID NO:13) and reverse primer 5-AACGTT GCGGCCGCTAGTTTCACAAACCCCAGG-3 (SEQ ID NO:14) are used for amplification. The BglII and NotI sites (bold, underlined) in the forward and reverse primers, respectively, are used to clone the resulting PCR fragment a bacterial expression vector fused at the COOH terminus to thioredoxin.thioredoxin The construct is transformed into an Escherichia coli strain K-12 comprising a mutation in the thioredoxin reductase gene and cultured at 25° C. until A600 ~0.6, induced with 1 mmol/L isopropyl-L-thio-β-D-galactopyranoside, and then cultured overnight at 25° C. The E. coli cell paste is resuspended and stirred at 4° C. in a 1:10 w/v of B-PER lysis buffer containing complete EDTA-free protease inhibitors. The mixture is then diluted with 5× stock buffer to a final concentration of 50 mmol/L Tris-HCl, 0.4 mol/L NaCl, 1% Triton-X100, 5% glycerol, and 10 mmol/L imidazole (pH 8-9). The sample is supplemented with lysozyme, DNase I, and 2 mmol/L MgCl2 (Sigma), stirred for 30 min, adjusted to 4 mmol/L EDTA, stirred for 20 min, and then centrifuged to remove the cell debris. The sample is adjusted to 40 mmol/L MgCl2 and stirred for 30 min before loading onto a Ni-IMAC column (GE Healthcare). The column is sequentially washed with 3 to 5 CV of 10 mmol/L imidazole in 20 mmol/L Tris-HCl (pH 8.0), 2 to 3 CV of 0.5% v/v Triton X-100 in 20 mmol/L Tris-HCl (pH 8.0), then with 5 to 10 CV of 70 mmol/L imidazole in 20 mmol/L Tris-HCl (pH 8.0). The truncated-APRIL is eluted with a linear gradient from 70 to 500 mmol/L imidazole in 20 mmol/L Tris-HCl, 5% glycerol (pH 8.0). Pooled protein fractions are dialyzed against PBS buffer containing 50 mmol/L imidazole, 0.1 mol/L L-Arg, 5% glycerol, 1 mmol/L EDTA (pH 8.0). The protein concentration is determined spectrophotometrically [E280 (1%)=0.94].

b) Recombinant, truncated, murine APRIL that was used as tool (competitor) for the phage display selections and ELISAs was transiently expressed as N-terminal monomeric Fc-fusion in HEK EBNA cells. Murine APRIL comprised histidine 106 to leucine 241. It was N-terminally fused to the hinge of a human IgG1 enabling heterodimerization with an unfused human IgG1 Fc portion (hole chain) by knobs-into-holes technology.

Example 1A3. Recombinant, Truncated Human BAFF

Recombinant, truncated human is produced as describe in Gordon, 2003 (Biochemistry; 42 (20): 5977-5983). Briefly, a DNA fragment encoding BAFF residues 82-285 is cloned into a pBr322 vector comprising a His-Tag at the N-terminus and a subsequent thrombin cleavage site, creating a fusion with an N-terminal His-tag followed by a thrombin cleavage site. An E. coli strain comprising T7 RNA polymerase gene under the control of the lacUV5 promoter is cultured to mid-log phase at 37° C. in LB medium with 50 mg/L carbenicillin and then cooled to 16° C. prior to induction with 1.0 mM IPTG. Cells are harvested by centrifugation after 12 h of further growth and stored at −80° C. The cell pellet is resuspended in 50 mM Tris, pH 8.0, and 500 mM NaCl and sonicated on ice. After centrifugation, the supernatant is loaded onto a Ni-NTA agarose column (Qiagen). The column is washed with 50 mM Tris, pH 8.0, 500 mM NaCl, and 20 mM imidazole and then eluted with a step gradient in the same buffer with 250 mM imidazole. BAFF-containing fractions are pooled, thrombin is added, and the sample is dialyzed overnight against 20 mM Tris, pH 8.0, and 5 mM $CaCl_2$ at 4° C. The protein is further purified on a monoQ (Pharmacia) column and finally on an S-200 size exclusion column in 20 mM Tris, 150 mM NaCl, and 5 mM $MgCl_2$.

Example 1B. Recombinant Cells Expressing Human BCMA on their Surface

Recombinant cells expressing human BCMA on their surface ("HEK293-BCMA cells") are generated as described in Ryan, 2007 (Mol Cancer Ther; 6 (11): 3009-18). Briefly, full-length human BCMA is amplified using forward primer 5-GAATTC AAGCTTGCCACCATGTTGCAGATGGCTGGGCAGTGCTCC-3 (SEQ ID NO:15) including a HindIII restriction site (bold, underlined) and Kozak consensus sequence and reverse primer 5-GAATTC TCTAGATTACCTAGCAGAAATTGATTTCTCTATCTCCGTAGCA-3 (SEQ ID NO:16) including a 3 stop codon and XbaI restriction site (bold, underlined) using IMAGE clone 687194 (Invitrogen) as a PCR template. The amplification product is cloned into an E. coli expression vector, comprising human cytomegalovirus (CMV) immediate early enhancer/promoter, a polyhistidine (6xHis), and a neomycin resistance gene, linearized and transfected into human embryonic kidney 293 (HEK293) cells. These cells are selected which express human BCMA on their surface high expressing stable clones are chosen by fluorescence-activated cell sorting analysis.

Figure 4:
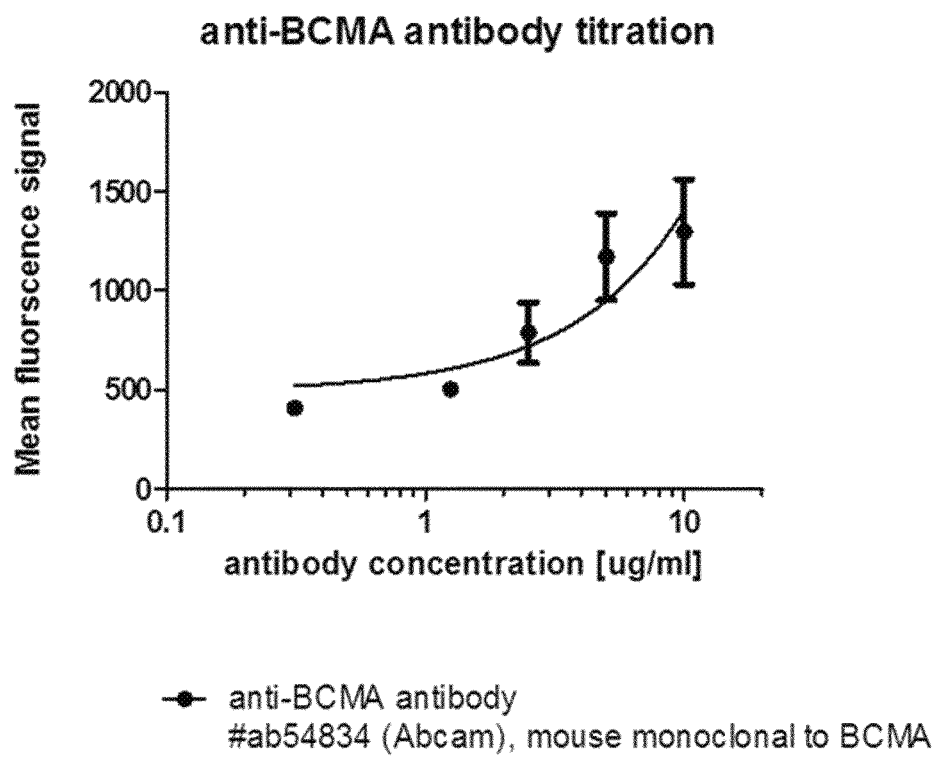
FIG. 4. BCMA expression on multiple myeloma cell lines. Increase of median fluorescence intensity upon binding of increasing concentrations of the anti-BCMA antibody (from 0.3 to 10 µg/mL) to H929 cells as detected by flow cytometry.

Example 1C. Human Myeloma Cell Line Expressing BCMA on their Surface a) Cell origin and culture conditions. Human MM cell line NCI-H929 is acquired from the American Type Culture Collection (ATCC CRL-9068). NCI-H929 cells are grown in RPMI 1640 supplemented with 10% fetal calf serum, 2 mM L-Glutamine, 1 mM Sodiumpyruvate. U266B1 (ATCC TIB-196) a human B lymphocyte myeloma cell line cultured in RPMI high Glucose, 10% FCS, 1% Glutamine, 1% Sodiumpyruvate, 10 mM HEPES). RPMI 8226 (ATCC CCL-155), a human B lymphocyte myeloma cell line cultured in DMEM, 10% FCS, 1% Glutamine. MKN45 (DSMZ ACC 409), a human gastric adenocarcinoma cell line cultured in DMEM containing 10% FCS and 1% Glutamine. BCMA expression on MM cell lines is confirmed by flow cytometry using fluorochrome-conjugated anti-human BCMA antibodies (BD Biosciences).

b) BCMA expression was assessed on three human myeloma cell lines (H929, RPMI-8226 and U266B1) by flow cytometry. Briefly, cells were harvested, washed, counted for viability, resuspended at 50 000 cells/well of a 96-well round bottom plate and incubated with anti human BCMA antibody (Abcam, #ab54834, mouse IgG1) at 10 µg/ml for 30 min at 4° C. (to prevent internalization). A mouse IgG1 was used as isotype control (BD Biosciences, #554121). Cells were then centrifuged (5 min at 350×g), washed twice and incubated with the FITC-conjugated anti mouse secondary antibody for 30 min at 4° C. At the end of incubation time, cells were centrifuged (5 min at 350×g), washed twice with FACS buffer, resuspended in 100 ul FACS buffer and analyzed on a CantoII device running FACS Diva software. FIG. 4 shows increase of median fluorescence intensity upon binding of increasing concentrations of the anti-BCMA antibody to H929 cells. Quantification of BCMA receptor number on membrane surface of H929, RPMI-8226 and U266B1 myeloma cell lines was assessed by QFIKIT analysis (Dako, #K0078, following manufacturer's instructions).

TABLE 2

Quantification of BCMA receptor number on membrane surface of H929, RPMI-8226 and U266B1 myeloma cell lines.

| Myeloma cell lines | BCMA receptor no |
|---|---|
| H929 | 6085 |
| RPMI-8226 | 6253 |
| U266(B1) | 2865 |

Example 1D. Obtaining Anti-BCMA Antibodies Via Immunization

Anti-BCMA antibodies are generated by immunization of rats with BCMA ECD as described in Ryan, 2007 (Mol Cancer Ther; 6 (11): 3009-18). Briefly, Sprague-Dawley rats are immunized subcutaneously with keyhole limpet hemocyanin-conjugated BCMA ECD (amino acids 5-54; NP_001183) using TiterMax® adjuvant (Sigma). Keyhole limpet hemocyanin conjugation is performed with a lysine residue using Imject mcKLHV (Pierce). Due to the high sequence homology between human and mouse BCMA proteins, rats are preferred for antibody production. B cells are harvested from immunized spleens and fused to P3-X63.Ag8 myeloma cells using a standard polyethylene glycol fusion protocol (Goding 1996; Monoclonal antibodies: principles and practice. $3^{rd}$ ed. Academic Press). Hybridomas are cultured in 80% Iscove's modified Dulbecco's medium supplemented with 10% fetal clone I, 4 mmol/L L-glutamine, 10% cloning factor and also including penicillin, streptomycin and 1× sodium hypoxanthine, aminopterin, and thymidine. ELISA testing is performed to detect binding of hybridoma culture supernatants to BCMA. Positive BCMA-binding hybridomas are further screened by flow cytometry for cell-based binding to BCMA transfectants (HEK293-BCMA cells). Chosen hybridomas undergo two rounds of limiting dilution cloning and are further expanded for purification. In addition, antibodies from those same chosen hybridomas are converted to chimeric antibodies with human constant regions by standard methods. Briefly, cDNAs encoding the heavy and light chain variable regions are amplified bz RT-PCR out of mRNA from the hybridomas and then joined in frame with cDNAs coding the heavy constant region of human IgG1 and the human kappa light chain constant region, respectively. These cDNAs are cloned into mammalian transient expression vectors and plasmid DNA is produced in E. coli and purified for transfection. HEK293 cells are transfected by a standard transfection method (calcium phosphate-based transfection) and 7 days later IgG1 antibodies are purified from culture supernatants by affinity chromatography on a Protein A column followed by isolation of the monomeric antibody fraction via size exclusion chromatography.

Example 1E. Obtaining Anti-BCMA Antibodies Out of an In Vitro, Recombinant Library Example 1E1. Construction of Generic Fab-Libraries Generic antibody libraries in the Fab-format are constructed on the basis of human germline genes using the following V-domain pairings: Vk3_20 kappa light chain with VH3_23 heavy chain for the DP47-3 library and Vk1_17 kappa light chain with VH1_69 heavy chain for the DP88-3 library. Both libraries are randomized in CDR3 of the light chain (L3) and CDR3 of the heavy chain (H3) and are assembled from 3 fragments per library by splicing by overlapping extension (SOE) PCR. Fragment 1 comprises the 5' end of the antibody gene including randomized L3, fragment 2 is a central constant fragment spanning from L3 to H3, whereas fragment 3 comprises randomized H3 and the 3' portion of the antibody gene. The following primer combinations are used to generate library fragments for DP47-3 library: fragment 1 (LMB3-LibL1b_new), fragment 2 (MS63-MS64), fragment 3 (Lib2H-fdseqlong). See Table 1 of WO2012020038. The following primer combinations are used to generate library fragments for the DP88-3 library: fragment 1 (LMB3-RJH_LIB3), fragment 2 (RJH31-RJH32) and fragment 3 (LIB88_2-fdseqlong). See tables 3 and 4 of WO2012020038.

The PCR protocol for the production of library fragments includes: 5 min of initial denaturation at 94° C.; cycles of 1 min at 94° C., 1 min at 58° C., and 1 min at 72° C.; and terminal elongation for 10 min at 72° C. For assembly PCR, equimolar ratios of the 3 fragments are used as template. The assembly PCR protocol includes: 3 min of initial denaturation at 94° C.; and 5 cycles of 30 seconds at 94° C., 1 min at 58° C., and 2 min at 72° C. At this stage, primers complementary to sequence outside fragments 1-3 are added and an additional 20 cycles are performed prior to a terminal elongation for 10 min at 72° C. After assembly of sufficient amounts of full length randomized Fab constructs, the Fab constructs are digested with NcoI/NotI for the DP47-3 library and with NcoI/NheI for the DP88-3 library alongside with similarly treated acceptor phagemid vector. For the DP47-3 library, 22.8 µg of Fab library is ligated with 16.2 µg of phagemid vector. For the DP88-3 library, 30.6 µg of Fab library is ligated with 30.6 µg of phagemid vector.

Purified ligations are used for 68 transformations for the DP47-3 library and 64 transformations for the DP88-3 library, respectively, to obtain final DP47-3 and DP88-3 libraries. Phagemid particles displaying the Fab libraries are rescued and purified by PEG/NaCl purification to be used for selection of anti-BCMA Fab clones.

Example 1E2. Selection of Anti-BCMA Fab Clones a) Selections are carried out against BCMA-ECD-biot. The antigen is biotinylated in vivo upon expression. Selections are carried out in solution according to the following protocol: (i) binding of $~10^{12}$ phagemid particles of library DP88-3 and 100 nM BCMA-ECD-biot for 0.5 hours in a total volume of 1 ml; (ii) capture of BCMA-ECD-biot and attached phage by the addition of $5.4 \times 10^7$ streptavidin-coated magnetic beads for 10 min; (iii) washing of beads using 5×1 ml PBS/Tween®20 and 5×1 ml PBS; (iv) elution of phage particles by the addition of 1 mL 100 mM TEA (triethylamine) for 10 min and neutralization by the addition of 500 µL 1M Tris/HCl pH 7.4; and (v) re-infection of log-phase E. coli TG1 cells (Zymo Research), infection with helper phage VCSM13 (Stratagene) and subsequent PEG/NaCl precipitation of phagemid particles to be used in subsequent selection rounds.

Selections are carried out over 3 rounds using constant BCMA-ECD-biot concentrations at 100 nM. In round 2, capture of antigen:phage complexes is performed on neutravidin plates instead of streptavidin beads. Specific binders are identified by ELISA as follows using: 100 µl of 100 nM BCMA-ECD-biot is coated in each well of neutravidin plates.

Fab-containing bacterial supernatants are added and binding Fabs are detected via their Flag-tags by using an anti-Flag/HRP secondary antibody. Once identified, anti-BCMA ECD clones are bacterially expressed in a 0.5 liter culture volume, affinity purified and further characterized by SPR-analysis using a BIACORE® instrument.

b) Anti-BCMA Fabs were established by phage display from synthetic Fab libraries consisting of VL and VH pairings derived from different V-domain families. Clones 13C2, 17A5, 83A10, 13D2, 14B11, 14E1, 29B11, and 29F3 were generated from Vk3_20/VH3_23 sublibrary, clone 13A4 from Vk2D_28/VH5_1 sublibrary, and clone 13A7 from Vk2D_28/VH3_23 sublibrary, respectively (Table 3). These libraries are based on entirely human frameworks with sequence diversity in CDR3 of VL (3 different lengths) and VH domains (6 different lengths).

TABLE 3

Anti-BCMA clones and respective VL/VH pairings

| Fab clone | VL domain | VH domain |
|---|---|---|
| 13C2 | Vk3_20 | VH3_23 |
| 17A5 | Vk3_20 | VH3_23 |
| 83A10 | Vk3_20 | VH3_23 |
| 13A4 | Vk2D_28 | VH5_1 |
| 13D2 | Vk3_20 | VH3_23 |
| 14B11 | Vk3_20 | VH3_23 |
| 14E1 | Vk3_20 | VH3_23 |
| 29B11 | Vk3_20 | VH3_23 |
| 29F3 | Vk3_20 | VH3_23 |
| 13A7 | Vk2D_28 | VH3_23 |

Selection rounds (biopanning) were performed in solution according to the following pattern: 1. pre-clearing of ~$10^{12}$ phagemid particles per library pool in immunotubes coated with 10 ug/ml of an unrelated human IgG to deplete the libraries of antibodies recognizing the Fc-portion of the antigens, 2. incubation of the non-Fc-binding phagemid particles with 100 nM biotinylated BCMA for 0.5 h in the presence of 100 nM unrelated non-biotinylated Fc knobs-into-holes construct for further depletion of Fc-binders in a total volume of 2 ml, 3. capture of biotinylated BCMA and specifically binding phage by splitting up and transferring the panning reaction into 16 wells on a neutravidin or streptavidin pre-coated microtiter plate for 20 min on a shaker, 4. washing of respective wells 10-30× with PBS/Tween 20 and 10-30× with PBS using a plate washer, 5. optional competitive washing step by addition of 230 nM murine APRIL to displace Fab clones that recognize the binding site of the natural ligand thus selecting for APRIL-non-competing phage antibodies, 6. elution of phage particles by addition of 125 ul 100 mM TEA (triethylamine) per well for 5-10 min and neutralization by addition of an equal volume of 1M Tris/HCl pH 7.4, 7. re-infection of log-phase *E. coli* TG1 cells with the eluted phage particles, infection with helperphage VCSM13, incubation on a shaker at 30° C. overnight and subsequent PEG/NaCl precipitation of phagemid particles to be used in the next selection round.

Selections were carried out over 3 to 5 rounds using constant antigen concentrations of 100 nM. Apart from selection campaigns during which only human BCMA was used as antigen, additional selection campaigns were carried out during which also cynomolgus or murine BCMA were used in an alternating fashion with human BCMA in order to select for cross-reactive antibodies. Moreover, as an alternative to streptavidin plate-based capture, capture of antigen: phage complexes was performed by addition of 5.4×$10^7$ streptavidin-coated magnetic beads to the panning reaction followed by washing steps using respective magnets under the conditions described above.

Specific binders were identified by surface plasmon resonance-screening of Fab-containing bacterial culture supernatants using BioRad's ProteOn XPR36 biosensor. In brief, after infection of log-phase *E. coli* TG1 cells with the eluted phage particles, single colony forming units (cfu) were plated and picked for inoculation of 1 ml expression cultures in 96-deep well plates. Fabs were captured from the supernatants on a ProteOn GLM chip that was derivatized with 8.000-10.000 RU of a goat anti-human IgG, F(ab')2 fragment specific polyclonal antibody (Jackson ImmunoResearch, #109-005-006) in vertical orientation. Subsequently, human, cynomolgus and murine BCMA as well as an unrelated Fc knobs-into-holes construct were injected as analytes in horizontal orientation. Clones that exhibited significant binding responses to BCMA and did not bind the Fc-portion of the antigens, were bacterially expressed in a 0.5 liter culture volume, affinity purified and kinetically characterized by SPR-analysis using a one-shot-kinetics protocol on BioRad's ProteOn XPR36 biosensor.

Example 1F. BCMA Binding Assays: Surface Plasmon Resonance a) To measure binding affinities of BCMA antibody to immobilized BCMA, surface plasmon resonance measurements are performed on a Biacore® 3000 instrument (Pharmacia Biosensor). The receptor BCMA (BCMA-ECD) is coupled to the sensor chip at a level of 400 resonance units using the amine coupling protocol as provided by manufacturer. Alternative BCMA-ECD-biot is coupled to a streptavidin-sensor chip, also at a level of 400 resonance units, using the protocol as provided by the manufacturer. In all experiments, flow cell 1 is used as the reference cell. Sensorgrams are recorded for Fab solutions ranging in concentration from 0.1 pM to 200 nM. Nonlinear regression analysis is used to calculate kinetic constants and binding constants simultaneously with the use of the manufacturer's software. Fab clones with monovalent binding affinities to BCMA-ECD of 100 nM are converted into IgGs by standard methods. Briefly, cDNAs encoding the heavy and light chain variable regions are joined in frame with cDNAs coding the heavy constant region of human IgG1 and the human kappa light chain constant region, respectively. These cDNAs are cloned into mammalian transient expression vectors and plasmid DNA is produced in *E. coli* and purified for transfection. HEK293 cells are transfected by a standard transfection method (calcium phosphate-based transfection) and 7 days later IgG1 antibodies are purified from culture supernatants by affinity chromatography on a Protein A column followed by isolation of the monomeric antibody fraction via size exclusion chromatography.

b) Affinities (KD) of anti-BCMA Fab clones were measured by surface plasmon resonance using a ProteOn XPR36 instrument (Biorad) at 25° C. with biotinylated human, cynomolgus and murine BCMA immobilized on NLC chips by neutravidin capture (Table 4). An unrelated biotinylated Fc knobs-into-holes construct was immobilized in a similar fashion as negative control Immobilization of antigens (ligand): Recombinant antigens were diluted with PBST (10 mM phosphate, 150 mM sodium chloride pH 7.4, 0.005% Tween 20) to 10 ug/ml, then injected at 40 ul/minute for 300 s in vertical orientation. Injection of analytes: For one-shot kinetics measurements, injection direction was changed to horizontal orientation, two-fold dilution series of purified Fab (varying concentration ranges) were injected simultaneously at 40 ul/min along channels 1-5, with association times of 200 or 300 s, and dissociation times of 300 s. Buffer (PBST) was injected along the sixth channel to provide an "in-line" blank for referencing. Association rate constants (kon) and dissociation rate constants (koff) were calculated using a simple one-to-one Langmuir binding model in ProteOn Manager v3.1 software by simultaneously fitting the association and dissociation sensorgrams. The equilibrium dissociation constant (KD) was calculated as the ratio koff/kon. Regeneration was performed in horizontal orientation using 10 mM glycine-HCl pH 1.5 at a flow rate of 100 ul/min for a contact time of 18 s.

TABLE 4

| Monovalent affinities of anti-BCMA Fab clones: | | | |
|---|---|---|---|
| Fab clone | $K_D$ human BCMA [nM] | $K_D$ cynomolgus BCMA [nM] | $K_D$ murine BCMA [nM] |
| 13C2 | 196 | — | 144 |
| 17A5 | 45 | — | 74 |
| 83A10 | 76 | 1510 | 1134 |
| 13A4 | 1.8 | — | — |
| 13D2 | 86 | weak | weak |
| 14B11 | 383 | — | — |
| 14E1 | 91 | weak | weak |
| 29B11 | 224 | — | weak |
| 29F3 | 87 | — | weak |
| 13A7 | 235 | — | — | c) Assessment of binding of anti-BCMA antibodies to recombinant BCMA by surface plasmon resonance (SPR) as follow. All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). The avidity of the interaction between anti-BCMA antibodies and recombinant BCMA Fc(kih) (human, cynomolgus and murine) was determined. Biotinylated recombinant human, cynomolgus and murine BCMA Fc(kih) were directly coupled on a SA chip following instructions (Biacore, Freiburg/Germany). The immobilization level ranged from 200 to 700 RU. The anti-BCMA antibodies were passed at a 2-fold concentration range (1.95 to 500 nM) with a flow of 30 µL/minutes through the flow cells over 120 seconds. The dissociation was monitored for 180 seconds. Bulk refractive index differences were corrected for by subtracting the response obtained on the reference flow cell. Here, the anti-BCMA antibodies were flown over an empty surface previously activated and deactivated as described in the standard amine coupling kit. Apparent kinetic constants were derived using the Biacore T200 Evaluation Software (vAA, Biacore AB, Uppsala/Sweden), to fit rate equations for 1:1 Langmuir binding by numerical integration, despite the bivalency of the interaction for comparison purposes.

The affinity of the interaction between anti-BCMA antibodies and recombinant human BCMA Fc(kih) was also determined. Anti-human Fab antibody (GE Healthcare) was directly coupled on a CM5 chip at pH 5.0 using the standard amine coupling kit (Biacore, Freiburg/Germany). The immobilization level was about 6500 RU. Anti-BCMA antibody was captured for 90 seconds at 25 nM. Recombinant human BCMA Fc(kih) was passed at a 4-fold concentration range (1.95 to 500 nM) with a flow of 30 µL/minutes through the flow cells over 120 seconds. The dissociation was monitored for 120 seconds. Bulk refractive index differences were corrected for by subtracting the response obtained on reference flow cell. Here, recombinant BCMA was flown over a surface with immobilized anti-human Fab antibody but on which HBS-EP has been injected rather than anti-BCMA antibody. Kinetic constants were derived using the Biacore T100 Evaluation Software (vAA, Biacore AB, Uppsala/Sweden), to fit rate equations for 1:1 Langmuir binding by numerical integration (Table 5). Binding of 83A10 anti-BCMA antibody to recombinant cynomolgus BCMA Fc(kih) and murine BCMA Fc(kih) was also measured (Table 6).

TABLE 5

Affinity constants determined by fitting rate equations for 1:1 Langmuir binding

| Ligand | Analyte | Kon (1/Ms) | Koff (1/s) | KD (M) |
| --- | --- | --- | --- | --- |
| 13C2 anti-BCMA IgG | huBCMA Fc(kih) | 2.4E+05 | 1.1E−02 | 4.7E−08 |
| 17A5 anti-BCMA IgG | huBCMA Fc(kih) | 2.2E+05 | 1.9E−03 | 8.7E−09 |
| 83A10 anti-BCMA IgG | huBCMA Fc(kih) | 6.2E+05 | 2.5E−03 | 4.1E−09 |
| 29F3 anti-BCMA IgG | huBCMA Fc(kih) | 3.2E+05 | 6.8E−03 | 2.1E−08 |
| 13A7 anti-BCMA IgG | huBCMA Fc(kih) | 8.0E+04 | 7.9E−03 | 1.0E−07 |
| 13A4 anti-BCMA IgG | huBCMA Fc(kih) | 7.2E+04 | 3.6E−04 | 5.1E−09 |
| 13D2 anti-BCMA IgG | huBCMA Fc(kih) | 3.6E+05 | 9.3E−03 | 2.6E−08 |
| 14B11 anti-BCMA IgG | huBCMA Fc(kih) | 1.5E+05 | 1.6E−02 | 1.1E−07 |
| 14E1 anti-BCMA IgG | huBCMA Fc(kih) | 4.0E+05 | 8.1E−03 | 2.0E−08 |
| 29B11 anti-BCMA IgG | huBCMA Fc(kih) | 1.7E+05 | 6.6E−03 | 4.0E−08 |

TABLE 6

Binding of recombinant BCMA Fc(kih) to 83A10 anti-BCMA antibody.

| Ligand | Analyte | Kon (1/Ms) | Koff (1/s) | KD (M) |
| --- | --- | --- | --- | --- |
| 83A10 anti-BCMA IgG | huBCMA Fc(kih) | 6.2E+05 | 2.5E−03 | 4.1E−09 |
| 83A10 anti-BCMA IgG | cyBCMA Fc(kih) | 2.8E+05 | 2.0E−02 | 7.2E−08 |
| 83A10 anti-BCMA IgG | muBCMA Fc(kih) | 2.0E+05 | 4.0E−02 | 2.0E−07 | a) cynomolgus BCMA Fc(kih).
b) murine BCMA Fc(kih)

Example 1G. BCMA-Signaling Assay: NF-κB Activation a) As described in Ryan, 2007 (Mol Cancer Ther; 6 (11): 3009-18), NCI-H929 cells are washed and incubated in RPMI supplemented with 0.25% fetal bovine serum for 24 h before treatment. The cells are then untreated or treated with 0.1 µg/mL TNF-α, 100 ng/mL, preferably 1000 ng/mL heat-treated HT-truncated-APRIL, 100 ng/mL, preferably 1000 ng/mL truncated-APRIL, 0.1 pM to 200 nM isotype control, or 0.1 pM to 200 nM anti-BCMA antibodies for 20 min. To evaluate ligand blockade, cells pre-treated for 20 min with 0.1 pM to 200 nM of anti-BCMA antibodies or an isotype control antibody are treated with 1 µg/mL of truncated-APRIL. Cells are then harvested, washed, and lysed with 50 mmol/L Tris-HCl (pH 7.5), 1% NP$_4$0, 150 mmol/L NaCl, 1 mmol/L EDTA, 1 mmol/L EGTA supplemented with protease, and phosphatase inhibitors. Protein extracts are then analyzed for NF-κB activity using a TransAM® chemiluminescent assay kit (Active Motif) and the luminescent signal reading is performed with a Fusion HT plate reader (Packard Instruments).

b) Briefly, H929 cells were starved in RPMI 1640 with 0.25% FCS for 24 h at 37° C. in cell incubator. At the end of the starvation time, cells were harvested, counted and cell viability evaluated using ViCell. Viable cells were adjusted to 4×106 cells per ml in BSA-containing FACS Stain Buffer (BD Biosciences). 30 µl of this cell suspension were further aliquoted per well into a round-bottom 96-well plate and pre-incubated with anti-BCMA antibodies (15 or 50 ug/ml) or isotype control antibodies (10, and 40 ug/ml) for 20 min in cell incubator. Cells were then supplemented with 1 ug/ml recombinant mouse Δ-APRIL tagged with hemagglutinin (HA) (R&D Systems Europe, #7907-AP-010) for 40 min at 37° C. Heat inactivated Δ-APRIL (HI APRIL) was used in the assay to confirm the specificity of Δ-APRIL-induced NFkB signal (heat inactivation was performed by treatment of Δ-APRIL at 60° C. for 1 h). At the end of incubation time, cells were harvested, washed, lysed, and processed according to the manufacturer's protocol of the Nuclear Extract Kit (Active Motif, #40410). Protein extracts were analyzed for NF-κB activity using a TransAm© NFκB p65 Chemi Assay kit (Active Motif, #40097) following manufacturer's instructions. Luminescent signal was read using the Spectra Max M5 luminometer (Molecular Devices).

Example 1H. Screening Anti-BCMA Antibodies to Select Antibodies not Affected by 100 ng/mL, Preferably 1000 ng/mL of APRIL or BAFF in their Binding to BCMA and that Neither Promote Nor Block Signaling Via the BCMA Intracellular Domain The invention relates to the generation of an anti-human BCMA antibody that 1) binds to human BCMA, 2) binding to BCMA is not affected by 100 ng/mL, preferably 1000 ng/mL of APRIL and BAFF, 3) does not block or reduce >20%, preferably >15% or increase >20%, preferably >15% APRIL-dependent NF-κB activation, 4) does not block or reduce >20%, preferably >15% or increase >20%, preferably >15% BAFF-dependent NF-κB activation, 5) does not induce NF-κB activation by itself, without APRIL or BAFF. Table 10 shows the screening paradigm for selection of a BCMA antibody with desired new properties: non-ligand binding/blocking, non-ligand competing. Antibodies are selected whose binding to BCMA is not blocked by APRIL or by BAFF.

Example 1H1. Binding to BCMA on HEK293-BCMA Cells, Plate-Bound-BCMA or BCMA-Positive Multiple Myeloma Cell Lines (Flow Cytometry and ELISA)

a) Anti-BCMA antibodies coming either from the immunization approach and/or from the screening of the recombinant in vitro library described above are analyzed by flow cytometry for binding to human BCMA on HEK293-BCMA cells. Briefly, cultured cells are harvested, counted and cell viability is evaluated using the Trypan Blue exclusion method. Viable cells are then adjusted to $2 \times 10^6$ cells per ml in BSA-containing FACS Stain Buffer (BD Biosciences). 90 µl of this cell suspension are further aliquoted per well into a round-bottom 96-well plate. 10 µl of the anti-BCMA antibodies or corresponding IgG control are added to the cell-containing wells to obtain final concentrations of 0.1 pM to 200 nM. All constructs and control IgG are used at the same molarity. After incubation for 30 min at 4° C., the cells are centrifuged (5 min, 350×g), washed with 150 µl/well FACS Stain Buffer (BD Biosciences), resuspended and incubated for an additional 30 min at 4° C. with 12 µl/well fluorochrome-conjugated AffiniPure F(ab')2 Fragment goat anti-human IgG Fcγ Fragment Specific (Jackson Immuno Research Lab; working solution: 1:20). Cells are then washed with Stain Buffer (BD Biosciences) 120 µl/well and pelleted down by centrifugation at 350×g for 5 min. A second washing step is performed using FACS Stain Buffer 150 µl/well. The samples are resuspended in 200 µl/well FACS Stain Buffer and acquired and analyzed using an LSR II flow cytometer with FACSDiva® software (BD Biosciences). The mean fluorescence intensity (MFI) is plotted as a function of anti-BCMA antibody concentration to obtain the binding curve and to calculate the effective antibody concentration to reach 50% of maximal binding ($EC_{50}$). Anti-BCMA antibodies that bind to BCMA on cells as judged from this assay are selected for the next screening step, namely the competition BCMA binding assay against APRIL and BAFF (step (Example 1H2) below).

Figure 5:
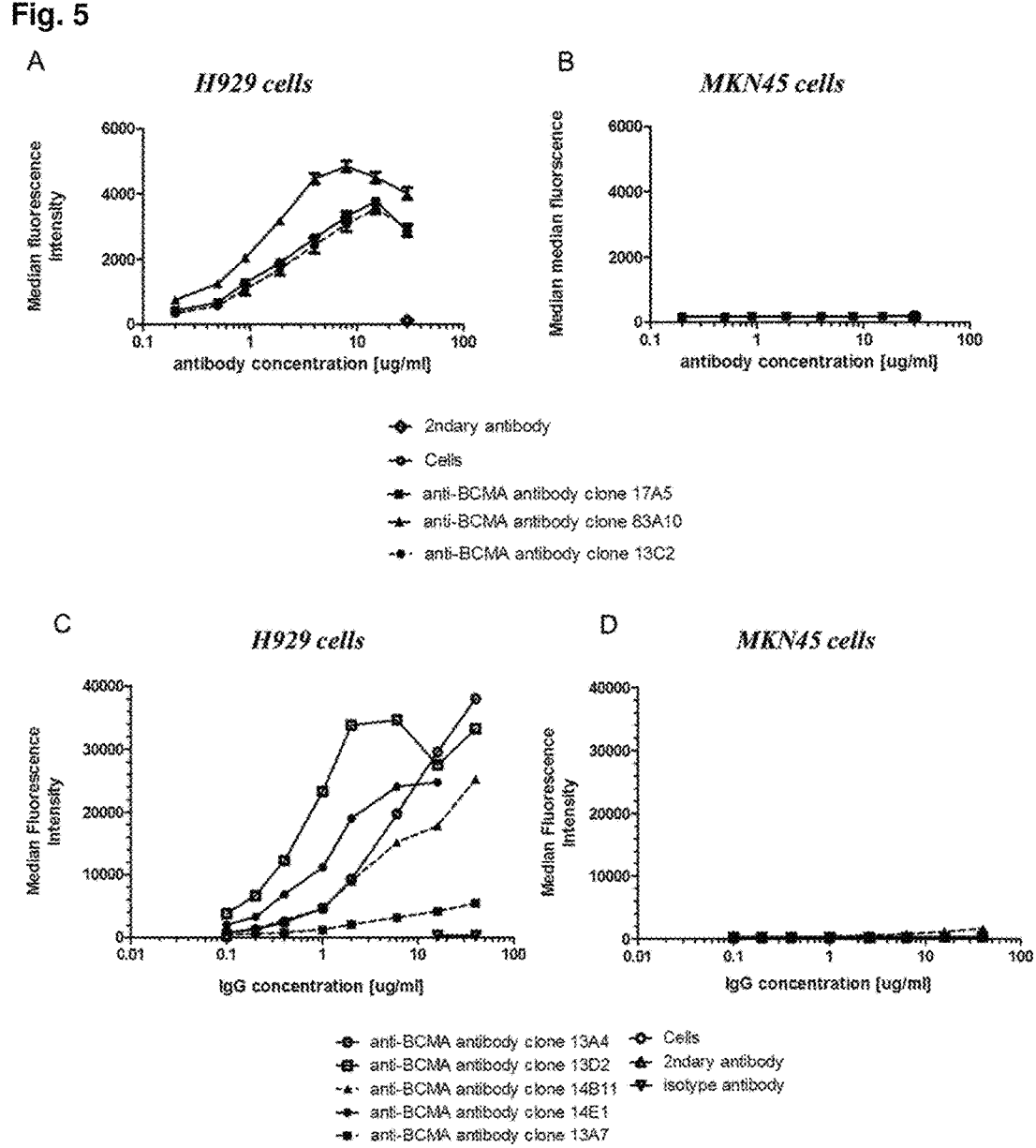
FIG. 5. Binding of anti-BCMA antibodies on BCMA-positive multiple myeloma cells. Mean fluorescence intensity for anti-BCMA IgG clones plotted in function of anti-BCMA antibody concentrations (from 0.2 to 40 µg/mL); (A) clones 13C2, 17A5, 83A10 on H929 cells, (B) clones 13C2, 17A5, 83A10 on MKN45 cells, (C) clones 13A4, 13D2, 14E1, 13A7, 14B11 on H929 cells (D) clones 13A4, 13D2, 14E1, 13A7, 14B11 on MKN45 cells.

The properties of antibodies that show binding to human BCMA on HEK293-BCMA cells are confirmed using an ELISA method as described by Ryan et al. (2007). Briefly, immunosorb 96-well plates are coated with 1.5 µg/mL of GST-BCMA-ECD, washed with PBS+1% Tween (PBS-T), and blocked with PBS-T plus 1% serum albumin BCMA-coated plates are incubated with hybridoma culture supernatants for 2 h at room temperature, washed 5 times with PBS-T, and incubated with peroxidase-conjugated goat-anti-rat IgG. Following incubation with secondary antibody, plates are washed, incubated with 3,3,5,5-tetramethylbenzidine substrate, and stopped with an equal volume of 1 mol/L $H_2SO_4$.

b) Anti-BCMA IgG antibodies (clones 13C2, 17A5, 83A10, 13A4, 13D2, 14E1, 13A7, 14B11) were analyzed by flow cytometry for binding to human BCMA on BCMA-expressing H929 cells. MKN45 (human gastric adenocarcinoma cell line that does not express BCMA) was used as negative control. Briefly, cultured cells are harvested, counted and cell viability was evaluated using ViCell. Viable cells are then adjusted to $2 \times 10^6$ cells per ml in BSA-containing FACS Stain Buffer (BD Biosciences). 100 µl of this cell suspension were further aliquoted per well into a round-bottom 96-well plate and incubated with 30 µl of the anti-BCMA antibodies or corresponding IgG control for 30 min at 4° C. All anti-BCMA antibodies (and isotype control) were titrated and analyzed in final concentration range between 0.1-40 ug/ml. Cells were then centrifuged (5 min, 350×g), washed with 120 µl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells were then washed twice with Stain Buffer (BD Biosciences), fixed using 100 ul BD Fixation buffer per well (#BD Biosciences, 554655) at 4° C. for 20 min, resuspended in 120 µl FACS buffer and analyzed using BD FACS CantoII. FIG. 5 shows the mean fluorescence intensity for anti-BCMA IgG clones plotted in function of anti-BCMA antibody concentration; (A) clones 13C2, 17A5, 83A10 on H929 cells, (B) clones 13C2, 17A5, 83A10 on MKN45 cells, (C) clones 13A4, 13D2, 14E1, 13A7, 14B11 on H929 cells (D) clones 13A4, 13D2, 14E1, 13A7, 14B11 on MKN45 cells. EC50 values (denoting the antibody concentration required to reach 50% of the maximal binding) for the binding of clones 13C2, 17A5, 83A10 to H929 cells are summarized in Table 7.

TABLE 7

| EC50 values for binding of anti-BCMA antibodies to H929 multiple myeloma cells | | | |
|---|---|---|---|
| | Anti-BCMA antibody clone 13C2 | Anti-BCMA antibody clone 83A10 | Anti-BCMA antibody clone 17A5 |
| EC50 (nM) | 13.9 | 12.5 | 9.0 |
| EC50 (ug/ml) | 2.0 | 1.8 | 1.3 |

Example 1H2. 100 ng/mL, Preferably 1000 ng/mL of APRIL or BAFF does not Alter BCMA Antibody Binding to Human-BCMA (Flow Cytometry and ELISA)

a) Anti-BCMA antibodies selected from step (Example 1H1) above are then analyzed by flow cytometry for binding to human BCMA on HEK293-BCMA cells in the presence and absence of 100 ng/mL, preferably 1000 ng/mL APRIL or BAFF. Viable HEK293-BCMA cells are adjusted to $2 \times 10^6$ cells per ml in BSA-containing FACS Stain Buffer (BD Biosciences). 90 µl of this cell suspension are further aliquoted per well into a round-bottom 96-well plate. 10 µl of the anti-BCMA antibodies or corresponding IgG control are added to the cell-containing wells to obtain final concentrations of 0.1 pM to 200 nM. All constructs and control IgG are used at the same molarity. After incubation for 30 min at 37° C., in the presence and absence of 100 ng/ml, preferably 1000 ng/mL of APRIL and BAFF, respectively, the cells are centrifuged (5 min, 350×g), washed with 150 µl/well FACS Stain Buffer (BD Biosciences), resuspended and incubated for an additional 30 min at 4° C. with 12

µl/well fluorochrome-conjugated AffiniPure F(ab')2 Fragment goat anti-human IgG Fcγ Fragment Specific (Jackson Immuno Research Lab; working solution: 1:20). Cells are then washed with Stain Buffer (BD Biosciences) 120 µl/well and pelleted down by centrifugation at 350×g for 5 min. A second washing step is performed using FACS Stain Buffer 150 µl/well. The samples are resuspended in 200 µl/well FACS Stain Buffer and acquired and analyzed using an LSR II flow cytometer with FACSDiva® software (BD Biosciences). The mean fluorescence intensity is plotted as a function of anti-BCMA antibody concentration to obtain the binding curve and to calculate the effective antibody concentration to reach 50% of maximal binding ($EC_{50}$). One binding curve is done in the presence of APRIL, another in its absence, and the same is done for presence and absence of BAFF. Those antibodies whose binding to BCMA is not affected by 100 ng/ml, preferably 1000 ng/mL of APRIL and also is not affected by 100 ng/ml, preferably 1000 ng/mL of BAFF are selected for next steps below. Representative binding curves for antibodies that are non-competing with the ligands APRIL and BAFF for binding to BCMA and for antibodies that are competing with these ligands for binding to BCMA are shown in FIG. 1.

Figure 6:
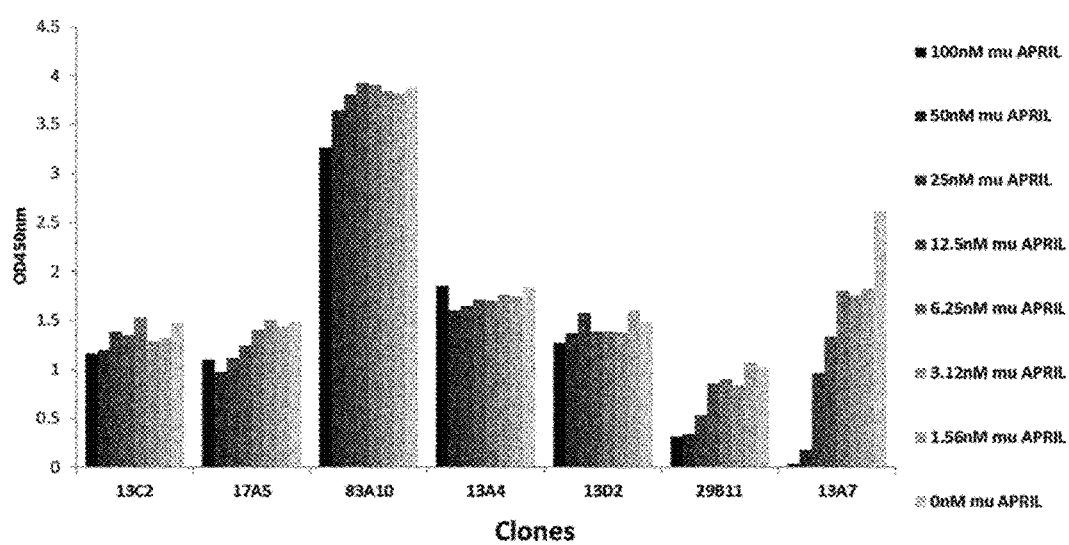
FIG. 6. Competition ELISA. ELISA results of 7 selected anti-BCMA Fab clones (13C2, 17A5, 83A19, 13A4, 13D2, 29B11, 13A7), at saturating concentrations of 500 or 1000 nM, binding to immobilized human BCMA in the presence of a concentration range of murine APRIL (from 1.56 to 100 nM) are shown. In case of non-competition, signals remain constant within the variability of the assay across the concentration range and signals in the presence of murine APRIL are comparable to those from the control wells where no murine APRIL was added. In case of competition a concentration dependent reduction of the signal is measured.

The properties of antibodies that show binding to human BCMA on HEK293-BCMA cells in the presence of 100 ng/mL, preferably 1000 ng/mL APRIL or BAFF are confirmed using an ELISA method as described by Ryan et al. (2007). Briefly, immunosorb 96-well plates are coated with 1.5 µg/mL of GST-BCMA-ECD, washed with PBS+1% Tween® (PBS-T), and blocked with PBS-T plus 1% serum albumin BCMA-coated plates are incubated with hybridoma culture supernatants for 2 h at room temperature, washed 5 times with PBS-T, and incubated with peroxidase-conjugated goat-anti-rat IgG. Following incubation with secondary antibody, plates are washed, incubated with 3,3,5,5-tetramethylbenzidine substrate, and stopped with an equal volume of 1 mol/L $H_2SO_4$. For plate-based ligand blockade, plates are coated with 1 µg/mL of GST-BCMA-ECD as described above. Coated plates are preincubated with purified antibodies at the specified concentrations, washed with PBS-T, and then incubated with 3 µg/mL of recombinant human MegaAPRIL (Alexis Biochemicals) or recombinant human BAFF (R&D Systems). APRIL or BAFF binding is detected using peroxidase-conjugated anti-FLAG followed by development with 3,3',5,5'-tetramethylbenzidine as described above.

b) Identification of non-APRIL-competing anti-BCMA Fabs or antibodies by ELISA. Binding of Fabs to immobilized human BCMA was assessed in the presence of increasing concentrations of murine APRIL. 25 nM biotinylated human BCMA (100 µl/well) were coated on a neutravidin plate and incubated on a shaker for 1 h at room temperature. 500 nM or 1000 nM purified Fabs were added to saturate the coated human BCMA for 1 h at room temperature. The plate was washed 3 times with PBS and murine APRIL was added at eight different concentrations using a two-fold dilution series in PBS buffer, ranging from 0 to 100 nM, and incubated on a shaker for 30 min. The plate was washed 3 times with PBS and anti-FLAG-HRP secondary antibody (1:4000) was added for 1 h. Again, the plate was washed 3 times with PBS and developed by adding 100 µl/well BM Blue POD (Roche). The reaction was stopped by adding 50 ul/well 1M $H_2SO_4$ and the OD was read at 450 nm (reference at 650 nm) for a final read-out of $OD_{450-650}$. Results for selected Fabs are shown in FIG. 6. The reduction (%) in OD values measured with the anti-BCMA clones in the absence vs. presence of 50 nM (1000 ng/mL) or 6.25 nM (140 ng/mL) muAPRIL (murine APRIL) is summarized in Table 8.

TABLE 8

Reduction in OD values measured (450 nm) in absence vs. presence of muAPRIL

Figure 7:
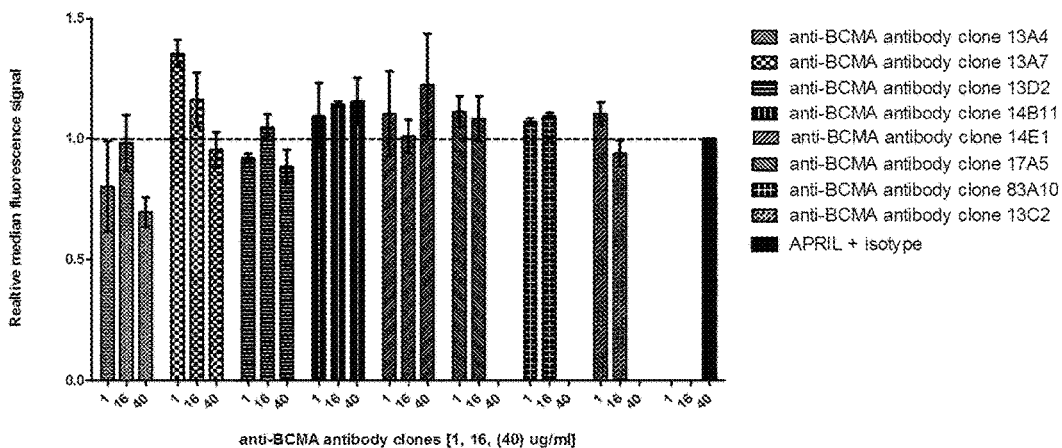
FIG. 7. Binding competition by FACS. Competition of Δ-APRIL with anti-BCMA antibodies detected by flow cytometry. Relative median fluorescence intensity of Δ-APRIL (FITC signal) used at a concentration of 1000 ng/mL detected in function of concentrations (1, 16, and 40 µg/mL) of anti-BCMA antibody clones 13A4, 13D2, 14E1, 14B11 on H929 cells. The median fluorescence intensity upon binding of Δ-APRIL in presence of the isotype control was set to one; the other signals were normalized to it. The detection of APRIL binding to BCMA-positive H929 cells in the presence of anti-BCMA antibodies was measured via anti-HA fluorochrome-conjugated antibody.
Figure 8:
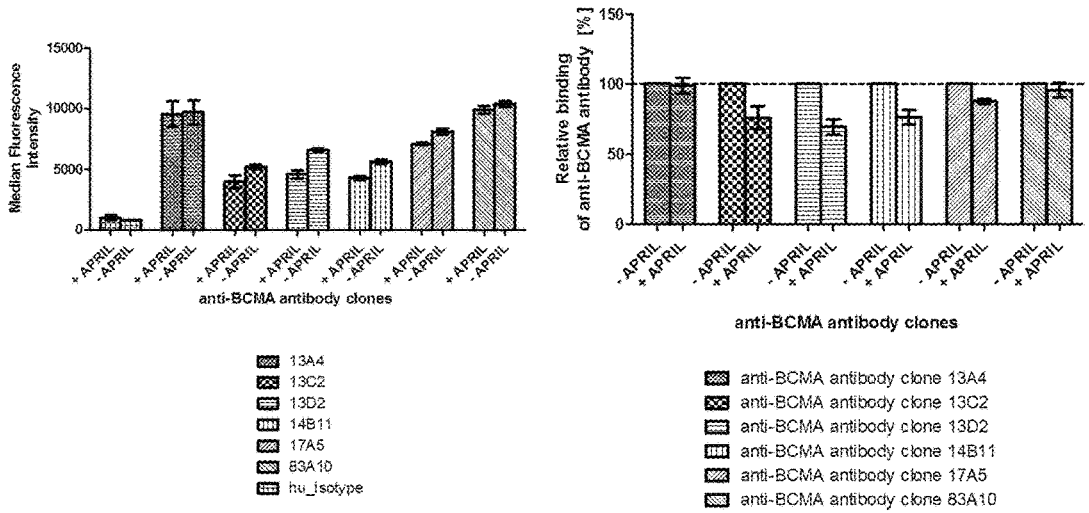
FIG. 8. Binding competition by FACS. Competition of anti-BCMA antibodies with Δ-APRIL detected by flow cytometry. The relative median fluorescence intensity of anti-BCMA antibody (Alexa.Fluor 647 signal) used at a concentration of 40 µg/mL for anti-BCMA antibody clones 13A4, 13C7, 13D2, 14B11, 17A5, 83A10 on RPMI cells detected in absence or presence of Δ-APRIL 1000 ng/mL. The median fluorescence intensity upon binding of anti-BCMA antibodies in absence of Δ-APRIL was set to one; the other signals respective to the anti-BCMA antibody in presence of Δ-APRIL were normalized to it. The detection of anti-BCMA antibodies binding to BCMA-positive RPMI cells in the presence of Δ-APRIL was measured via anti-human Fc fluorochrome-conjugated antibody.

| muAPRIL | Reduction (↓) in OD values in presence of muAPRIL Anti-BCMA antibody clones | | | | | | |
|---|---|---|---|---|---|---|---|
| (nM and ng/mL) | 13C2 | 17A5 | 83A10 | 13A4 | 13D2 | 29B11 | 13A7 |
| 50 nM/1000 ng/mL | 18.9% | 34.5% | 6.3% | 13.1% | 7.3% | 67.3% | 93.2% |
| 6.25 nM/140 ng/mL | no ↓ | 5.6% | no ↓ | 7.7% | 6.4% | 12.1% | 31.3% | c) Competition of Δ-APRIL with anti-BCMA antibodies detected by flow cytometry. The assessment of the eventual competition between Δ-APRIL and anti-BCMA antibodies was performed on H929 cells by quantifying the binding of Δ-APRIL in presence of increasing concentrations of anti-BCMA antibodies (clones 13C2, 17A5, 83A10, 13A4, 13D2, 14E1, 13A7, 14B11). Briefly, cultured cells were harvested, counted and cell viability evaluated using ViCell. Viable cells were adjusted to 1×10⁶ cells per ml in BSA-containing FACS Stain Buffer (BD Biosciences). 100 µl of this cell suspension are further aliquoted per well into a round-bottom 96-well plate and incubated with 30 µl of the anti-BCMA antibodies or corresponding IgG control for 30 min at 4° C. All anti-BCMA antibodies (and isotype control) are titrated and analyzed at final concentrations of 1, 16 and 40 ug/ml. Cells are then centrifuged (5 min, 350×g), washed with 120 µl/well FACS Stain Buffer (BD Biosciences), resuspended and incubated with 1 ug/ml recombinant mouse Δ-APRIL tagged with hemagglutinin (HA) (R&D Systems Europe, #7907-AP-010) for additional 30 min at 4° C. Cells are then washed once with 120 µl/well FACS Buffer and incubated with FITC-conjugated anti-HA antibody (Sigma Aldrich, #H7411) for 30 min at 4° C. At the end of incubation time, cells are washed with 120 µl/well FACS Buffer, fixed using 100 ul BD Fixation buffer per well (#BD Biosciences, 554655) at 4° C. for 20 min, resuspended in 80 µl FACS buffer and analyzed using BD FACS Fortessa. FIG. 7 shows the relative median fluorescence intensity of Δ-APRIL (FITC signal) detected in function of increasing concentrations of anti-BCMA antibody clones 13A4, 13D2, 14E1, 13A7, 14B11 on H929 cells. The median fluorescence intensity upon binding of Δ-APRIL in presence of the isotype control was set to one; the other signals were normalized to it.

d) Competition of anti-BCMA antibodies with Δ-APRIL detected by flow cytometry. The assessment of the eventual competition between Δ-APRIL and anti-BCMA antibodies was performed on RPMI cells by quantifying the binding of anti-BCMA antibodies (clones 13A4, 13C2, 13D2, 14B11, 17A5, 83A10,) in presence or absence of Δ-APRIL. Briefly, cultured cells were harvested, counted and cell viability evaluated using ViCell. Viable cells were adjusted to 1×10$^6$ cells per ml in BSA-containing FACS Stain Buffer (BD Biosciences). 100 μl of this cell suspension were further aliquoted per well into a round-bottom 96-well plate and incubated with 30 μl of the anti-BCMA antibodies or corresponding IgG control for 20 min at 4° C. All anti-BCMA antibodies and isotype control were analyzed at final concentrations 40 ug/ml. Cells were then centrifuged (5 min, 350×g), washed with 120 μl/well FACS Stain Buffer (BD Biosciences), resuspended and incubated with 1 ug/ml recombinant mouse Δ-APRIL tagged with hemagglutinin (HA) (R&D Systems Europe, #7907-AP-010) for additional 40 min at 4° C. Cells were then washed once with 120 μl/well FACS Buffer and incubated with with Alexa.Fluor 647-conjugated anti-human Fc antibody (Jackson Immuno Research Lab, #109-606-008) for 30 min at 4° C. At the end of incubation time, cells were washed with 120 μl/well FACS Buffer, fixed using 100 ul BD Fixation buffer per well (#BD Biosciences, 554655) at 4° C. for 20 min, resuspended in 80 μl FACS buffer and analyzed using BD FACS Fortessa. FIG. 8 shows the relative median fluorescence intensity of anti-BCMA antibody (Alexa.Fluor 647 signal) clones 13A4, 13C7, 13D2, 14B11, 17A5, 83A10 on RPMI cells detected in absence or presence of 1000 ng/mL of Δ-APRIL. The median fluorescence intensity upon binding of anti-BCMA antibodies in absence of Δ-APRIL was set to one; the other signals respective to the anti-BCMA antibody in presence of Δ-APRIL were normalized to it.

e) Competition of anti-BCMA antibodies with Δ-APRIL after simultaneous incubation detected by flow cytometry. The assessment of the eventual competition between Δ-APRIL and anti-BCMA antibodies was performed on H292 cells (NCI-H929, ATCC® CRL9068™) by quantifying the binding of anti-BCMA antibodies (clones 14B11, 13D2, 13A4, 17A5, 83A10) in presence or absence of Δ-APRIL. Briefly, cultured cells were harvested, counted and cell viability evaluated using ViCell. Viable cells were adjusted to 1×10$^6$ cells per ml in BSA-containing FACS Stain Buffer (BD Biosciences). 100 μl of this cell suspension were further aliquoted per well into a round-bottom 96-well plate and incubated with 30 μl of the anti-BCMA antibodies or corresponding IgG control and 30 μl of Δ-APRIL tagged with hemagglutinin (HA) (R&D Systems Europe, #7907-AP-010) for 40 min at 4° C. All anti-BCMA antibodies and isotype control were analyzed at final concentrations 20 ug/ml; Δ-APRIL at final concentrations 2.5 ug/ml. Cells were then centrifuged (5 min, 350×g) and washed with 120 μl/well FACS Stain Buffer (BD Biosciences). After that, cells were incubated with with Alexa.Fluor 647-conjugated anti-human Fc antibody (Jackson Immuno Research Lab, #109-606-008) and FITC-conjugated anti-HA antibody (Sigma Aldrich, #H7411) for 30 min at 4° C. At the end of incubation time, cells were washed with 120 μl/well FACS Buffer, fixed using 100 ul BD Fixation buffer per well (#BD Biosciences, 554655) at 4° C. for 20 min, resuspended in 80 μl FACS buffer and analyzed using BD FACS CantoII. FIG. 9A shows the mean fluorescence intensity and the relative fluorescence signal of the anti-BCMA antibody clone (Alexa.Fluor 647 signal) and FIG. 9B shows the mean fluorescence intensity and the relative fluorescence signal of Δ-APRIL (FITC signal) and the anti-BCMA antibody clone (Alexa.Fluor 647 signal). Detection of anti-BCMA antibody in presence of Δ-APRIL with FITC-conjugated anti-human Fc antibody was normalized to the signal of anti-BCMA antibody clone in absence Δ-APRIL. Detection of Δ-APRIL in presence of the anti-BCMA antibody clone with Alexa.Fluor 647-conjugated anti-HA antibody was normalized to Δ-APRIL signal in presence of the isotype control. Reduction in binding of anti-BCMA antibodies (20 μg/mL) clones 14B11, 13D2, 13A4, 17A5 and 83A10 in presence of Δ-APRIL (2.5 μg/mL) as detected with fluorochrome-conjugated anti-human Fc antibody is summarized in Table 9.

TABLE 9

Reduction in binding of anti-BCMA antibodies to H929 cells inpresence of APRIL

| Anti-BCMA antibody clones | Reduction (↓) in binding of anti-BCMA antibodies in presence of APRIL |
|---|---|
| 14B11 | 50% |
| 13D2 | 25% |
| 13A4 | 25% |
| 17A5 | 20% |
| 83A10 | 10% |

Example 1H3. BCMA Antibody does not Block or Increase APRIL-Dependent NF-κB Activation a) Antibodies selected as non-competing in step (Example 1H2) above (i.e., their BCMA binding curve is not affected by the presence of 100 ng/ml, preferably 1000 ng/mL of APRIL and is also not affected by the presence of 100 ng/ml, preferably 1000 ng/mL of BAFF) are then tested in step (Example 1H3) for effects on APRIL, BAFF, and BCMA mediated NF-κB activation. As APRIL is the high affinity ligand to BCMA, the blocking or agonist properties of anti-BCMA antibodies on APRIL signaling is first examined. As described in Ryan 2007 (Mol Cancer Ther; 6 (11): 3009-18), to verify whether anti-BCMA antibodies block or increase APRIL downstream signaling, NCI-H929 human multiple myeloma (MM) cells are washed and incubated in serum free RPMI for 24 h before treatment. The cells are then untreated or treated with 0.1 μg/mL TNF-α (used as positive control), 100 ng/mL, preferably 1000 ng/mL heat-treated HT-truncated-APRIL, 100 ng/mL, preferably 1000 ng/mL truncated-APRIL, 0.1 pM to 200 nM isotype control, or 0.1 pM to 200 nM anti-BCMA antibodies for 20 min. To evaluate APRIL blockade, cells pre-treated for 20 min with 0.1 pM to 200 nM of anti-BCMA antibodies or a respective isotype control antibody are treated with 100 ng/mL, preferably 1000 ng/mL of truncated-APRIL. Cells are then harvested, washed, and lysed with 50 mmol/L Tris-HCl (pH 7.5), 1% NPκ0, 150 mmol/L NaCl, 1 mmol/L EDTA, 1 mmol/L EGTA supplemented with protease, and phosphatase inhibitors. Protein extracts are then analyzed for NF-κB activity using a TransAM® chemiluminescent assay kit (Active Motif) and the luminescent signal reading is performed with a Fusion HT plate reader (Packard Instruments).

As NF-κB activity is assayed using a functional ELISA that detects chemiluminescent signal from p65 bound to the NF-κB consensus sequence, anti-BCMA antibodies that do not alter APRIL-mediated downstream signaling and NF-κB activation (i.e. that the mean luminescent signal detected by ELISA in nuclear extracts from NCI-H929 MM cells treated with APRIL alone is similar, not significantly reduced or increased, to that of nuclear extracts from NCI-H929 MM cells treated with APRIL and anti-BCMA antibodies) are selected for the next steps below.

b) It was assessed whether binding of anti-BCMA antibodies interferes with APRIL-induced NFkB activation, a known signaling pathway downstream of BCMA. Briefly, H929 cells were starved in RPMI 1640 with 0.25% FCS for 24 h at 37° C. in cell incubator. At the end of the starvation time, cells were harvested, counted and cell viability evaluated using ViCell. Viable cells were adjusted to 4×10⁶ cells per ml in BSA-containing FACS Stain Buffer (BD Biosciences). 30 μl of this cell suspension were further aliquoted per well into a round-bottom 96-well plate and pre-incubated with anti-BCMA antibodies (15 or 50 ug/ml) or isotype control antibodies (10, 20 and 40 ug/ml) for 20 min in cell incubator. Cells were then supplemented with 1 ug/ml recombinant mouse Δ-APRIL tagged with hemagglutinin (HA) (R&D Systems Europe, #7907-AP-010) for 40 min at 37° C. Heat inactivated Δ-APRIL (HI APRIL) was used in the assay to confirm the specificity of Δ-APRIL-induced NFkB signal (heat inactivation was performed by treatment of Δ-APRIL at 60° C. for 1 h). At the end of incubation time, cells were harvested, washed, lysed, and processed according to the manufacturer's protocol of the Nuclear Extract Kit (Active Motif, #40410). Protein extracts were analyzed for NF-kB activity using a TransAm© NFkB p65 Chemi Assay kit (Active Motif, #40097) following manufacturer's instructions. Luminescent signal was read using the Spectra Max M5 luminometer (Molecular Devices). The relative luminescence signal intensity obtained using H929 cells treated as described above was measured. The luminescence signal obtained upon binding of Δ-APRIL in presence of the isotype control was set to one; the other signals were normalized to it.

Example 1H4. BCMA Antibody does not Block or Increase BAFF-Dependent NF-κB Activation Antibodies selected as non-blocking and non-increasing APRIL-dependent NF-κB activation in step (Example 1H3) above are then tested in step (Example 1H3) for effects on BAFF mediated NF-κB activation. As described in Ryan 2007, (Mol Cancer Ther; 6 (11): 3009-18), to verify whether BCMA antibodies block or increase BAFF downstream signaling leading to NF-κB activation, NCI-H929 MM cells (CRL9068™) are washed and incubated in serum free RPMI medium for 24 h before treatment, as described in Ryan 2007, (Mol Cancer Ther; 6 (11): 3009-18), The cells are then untreated or treated with 0.1 μg/mL TNF-α, 100 ng/mL, preferably 1000 ng/mL heat-treated HT-truncated-BAFF, 100 ng/mL, preferably 1000 ng/mL truncated-BAFF, 0.1 pM to 200 nM isotype control, or 0.1 pM to 200 nM anti-BCMA antibodies for 20 min. To evaluate BAFF blockade, cells pre-treated for 20 min with 0.1 pM to 200 nM of anti-BCMA antibodies or a respective isotype control antibody are treated with 1 μg/mL of truncated-BAFF. Cells are then harvested, washed, and lysed with 50 mmol/L Tris-HCl (pH 7.5), 1% NP₄0, 150 mmol/L NaCl, 1 mmol/L EDTA, 1 mmol/L EGTA supplemented with protease, and phosphatase inhibitors. Protein extracts are then analyzed for NF-κB activity using a TransAM® chemiluminescent assay kit (Active Motif) and the luminescent signal reading is performed with a Fusion HT plate reader (Packard Instruments). Anti-BCMA antibodies that do not alter BAFF-mediated downstream signaling and NF-κB activation (i.e. that the mean luminescent signal from p65 bound to the NF-κB consensus sequence detected by ELISA in nuclear extracts from NCI-H929 MM cells treated with BAFF alone is similar, not significantly reduced or increased, to that of nuclear extracts from NCI-H929 MM cells treated with BAFF and anti-BCMA antibodies) are selected for the next steps below.

Example 1H5. BCMA Antibody does not Induce NF-κB Activation by Itself a) Antibodies selected as non-blocking and non-increasing BAFF-dependent NF-κB activation in step (Example 1H4) above are then tested in step (Example 1H5) for their intrinsic agonistic effects to mediate NF-κB activation. To verify whether BCMA antibodies are agonistic and induce downstream signaling by themselves, NCI-H929 cells are washed and incubated in serum-free RPMI medium for 24 h before treatment. The cells are then untreated or treated with 0.1 μg/mL TNF-α, 0.1 pM to 200 nM isotype control or 0.1 pM to 200 nM anti-BCMA antibodies for 20 min. Cells are then harvested, washed, and lysed with 50 mmol/L Tris-HCl (pH 7.5), 1% NP0, 150 mmol/L NaCl, 1 mmol/L EDTA, 1 mmol/L EGTA supplemented with protease, and phosphatase inhibitors. Protein extracts are then analyzed for NF-κB activity using a TransAM® chemiluminescent assay kit (Active Motif) and the luminescent signal reading is performed with a Fusion HT plate reader (Packard Instruments). Anti-BCMA antibodies that do not induce downstream signaling and NF-κB activation (i.e. that the mean luminescent signal from p65 bound to the NF-κB consensus sequence detected by ELISA in nuclear extracts from NCI-H929 MM cells treated with anti-BCMA antibodies alone is similar, not significantly increased, to that of nuclear extracts from NCI-H929 MM cells treated with isotype control antibody) are finally selected for further production and in vitro and in vivo characterization. They represent the anti-BCMA antibodies that are non-ligand blocking, non-competing, and non-signaling (see Table 10).

b) It was assessed whether binding of anti-BCMA antibodies to BCMA-expressing H929 cells induces NFkB activation, a known signaling pathway downstream of BCMA. Briefly, H929 cells were starved in RPMI 1640 with 0.25% FCS for 24 h at 37° C. in cell incubator. At the end of the starvation time, cells were harvested, counted and cell viability evaluated using ViCell. Viable cells were adjusted to 4×10⁶ cells per ml in BSA-containing FACS Stain Buffer (BD Biosciences). 30 μl of this cell suspension were further aliquoted per well into a round-bottom 96-well plate and incubated with 30 μl of the anti-BCMA antibodies at 100 or 350 nM (14 or 50 ug/ml) for 20 min at 37° C. As negative controls, cells were either left untreated or incubated with the corresponding IgG isotype control antibodies 100 nM (14 ug/ml) for 20 min at 37° C. As positive controls, cells were incubated with 1 ug/ml recombinant mouse Δ-APRIL tagged with hemagglutinin (HA) (R&D Systems Europe, #7907-AP-010) for 20 min at 37° C. At the end of incubation time, cells were harvested, washed, lysed, and processed according to the manufacturer's protocol of the Nuclear Extract Kit (Active Motif, #40410). Protein extracts were analyzed for NFkB activity using a TransAm© NFkB p65 Chemi Assay kit (Active Motif, #40097) following manufacturer's instructions. Luminescent signal was read using the Spectra Max M5 luminometer (Molecular Devices). The relative luminescence signal intensity obtained from H929 cells treated as described above was measured. The luminescence signal obtained upon binding of Δ-APRIL in presence of the isotype control was set to one; the other signals were normalized to it.

TABLE 10

Screening paradigm for BCMA antibody selection

| Evaluation step (in chronologic order) | Selection criteria | Description of technique |
|---|---|---|
| 1) Binding to BCMA | Binding | Binding to plate-bound-BCMA cells (ELISA) |
| 2) Binding to BCMA not reduced by 100 ng/mL, preferably 1000 ng/mL APRIL or BAFF | No reduction | Binding to plate-bound-BCMA is not affected by 100 ng/mL, preferably 1000 ng/mL of APRIL or BAFF (ELISA) |
| 3) Non-Activation of NF-κB downstream signaling | No change in all three cases | APRIL/BAFF-dependent activation in MM cell line NCI-H929 (chemiluminescent ELISA) |
| 3.1) Does anti-BCMA antibody block or increase APRIL-dependent NF-κB activation? | | |
| 3.2) Does anti-BCMA antibody block or increase BAFF-dependent NF-κB activation? | | |
| 3.3) Does anti-BCMA antibody induce NF-κB activation by itself? | | |

Example 2—Production of Therapeutic Anti-BCMA Antibodies that do not Block Ligand (APRIL, BAFF) Binding and Neither Promote Nor Block Signaling Via the BCMA Intracellular Domain and Whose Binding to BCMA is not Affected by 100 ng/ml, Preferably 1000 ng/mL of APRIL or by 100 ng/ml, Preferably 1000 ng/mL of BAFF If the selected antibodies after step (Example 1H5) above are derived from the in vitro selection out of the recombinant antibody library, then they are already unconjugated human IgG1 antibodies. Those selected antibodies after step (Example 1H5) above that are derived from immunization are in a rat-human chimeric format and are then preferably humanized to be able to apply them for therapy. In that case, standard antibody humanization methods are applied by transferring the complementarity-determining regions of those rat variable regions into human antibody variable region frameworks. Additional mutations are introduced into the variable regions, if necessary, to recover binding to BCMA as compared to the chimeric, parental antibody.

For the production of the antibody, the cells are co-transfected with two plasmids, (one for expression of the heavy chain of the antibody and another for expression of the light chain of the antibody), at a ratio of 1:1, respectively. Cells are grown as adherent monolayer cultures in T flasks using DMEM culture medium supplemented with 10% FCS, and are transfected when they are between 50 and 80% confluent. For the transfection of a T75 flask, 8 million cells are seeded 24 hours before transfection in 14 ml DMEM culture medium supplemented with FCS (at 10% V/V final), 250 µg/ml neomycin, and cells are placed at 37° C. in an incubator with a 5% $CO_2$ atmosphere overnight. For each T75 flask to be transfected, a solution of DNA, $CaCl_2$ and water is prepared by mixing 47 µg total plasmid vector DNA divided equally between the light and heavy chain expression vectors, 235 µl of a 1M $CaCl_2$ solution, and adding water to a final volume of 469 µl. To this solution, 469 µl of a 50 mM HEPES, 280 mM NaCl, 1.5 mM $Na_2HPO_4$ solution at pH 7.05 are added, mixed immediately for 10 sec and left to stand at room temperature for 20 sec. The suspension is diluted with 12 ml of DMEM supplemented with 2% FCS, and added to the T75 in place of the existing medium. The cells are incubated at 37° C., 5% $CO_2$ for about 17 to 20 hours, then medium is replaced with 12 ml DMEM, 10% FCS. The conditioned culture medium is harvested 5 to 7 days post-transfection centrifuged for 5 min at 1200 rpm, followed by a second centrifugation for 10 min at 4000 rpm and kept at 4° C.

The secreted antibodies are purified by Protein A affinity chromatography, followed by cation exchange chromatography and a final size exclusion chromatographic step on a Superdex® 200 column (Amersham Pharmacia) exchanging the buffer to phosphate buffer saline and collecting the pure monomeric IgG1 antibodies. Antibody concentration is estimated using a spectrophotometer from the absorbance at 280 nm. The antibodies were formulated in a 25 mM potassium phosphate, 125 mM sodium chloride, 100 mM glycine solution of pH 6.7.

Example 3—Generation of Anti-BCMA/Anti-CD3 T Cell Bispecific Antibodies

Example 3A. Generation of Anti-CD3 Antibodies

The following protein sequences of the VH and VL regions are used to generate human and cynomolgus monkey cross reactive CD3E antibodies as described in WO2007/042261.

H2C_VH (SEQ ID NO:7):

EVQLVESGGGLVQPGGSLKLSCAASGFTFNKYAMNWVRQAPGKGLEWVAR

IRSKYNNYATYYADSVKDRFTISRDDSKNTAYLQMNNLKTEDTAVYYCVR

HGNFGNSYISYWAYWGQGTLVTVSS

H2C_VL (SEQ ID NO:8)

QTVVTQEPSLTVSPGGTVTLTCGSSTGAVTSGYYPNWVQQKPGQAPRGLI

GGTKFLAPGTPARFSGSLLGGKAALTLSGVQPEDEAEYYCALWYSNRWVF

GGGTKLTVL

Briefly, oligonucleotides encoding the above sequences are joined together via PCR to synthesize cDNAs encoding the VH are VL sequences, respectively, of the anti-CD3 antibody.

Example 3B. Generation of Anti-BCMA/Anti-CD3 T Cell Bispecific 1+1 Format with Fc Anti-BCMA/anti-CD3 T cell bispecific are produced for the human or humanized anti-BCMA antibodies selected after step (Example 1H5). cDNAs encoding the full heavy and light chains of the corresponding anti-BCMA IgG1 antibodies, as described in Example 2, as well as the anti-CD3 VH and VL cDNAs describe in Example 3A, are used as the starting materials. For each bispecific antibody, four protein chains are involved comprising the heavy and light chains of the corresponding anti-BCMA antibody and the heavy and light chains of the anti-CD3 antibody described above, respectively. In order to minimize the formation of side-products with mispaired heavy chains, for example with two heavy chains of the anti-CD3 antibody, a mutated heterodimeric Fc region is used carrying "knob-into-hole mutations" and an engineered disulphide bond, as described in WO2009080251 and in WO2009080252. In order to minimize the formation of side-products with mispaired light chains, for example with two light chains of the anti-BCMA antibody, a CH1× constant kappa crossover is applied to the heavy and light chains of the anti-CD3 antibody using the methodology described in WO2009080251 and in WO2009080252.

Briefly, each bispecific antibody is produced by simultaneous cotransfection of four mammalian expression vectors encoding, respectively: a) the full light chain cDNA of the corresponding BCMA antibody, b) the full heavy chain cDNA of the corresponding BCMA antibody carrying the "hole mutations" in the Fc region to produce a heterodimeric antibody (see details below), c) a fusion cDNA generated by standard molecular biology methods, such as splice-overlap-extension PCR, encoding a fusion protein made of (in N- to C-terminal order) secretory leader sequence, VL of the anti-CD3 antibody described above and human CH1 domain of an IgG1 antibody and d) a fusion cDNA generated by standard molecular biology methods, such as splice-overlap-extension PC, encoding a fusion protein made of (in N- to C-terminal order) secretory leader sequence, VH of the anti-CD3 antibody described above, constant kappa domain of a human light chain cDNA, hinge region of a human IgG1 antibody, and Fc region (CH2 and CH3 domains) of a human IgG1 antibody including a "knob mutation" (see details below) in the Fc region to produce a heterodimeric antibody. Co-transfection of mammalian cells and antibody production and purification using the methods described above for production of human or humanized IgG1 antibodies (see Example 2). The "knob-into-hole mutations" in the human IgG1 Fc region consist of: T366W, known as the "knob mutation"; and T366S, L368A, and Y407V, collectively known as the "hole mutations". In addition, a disulfide can be included to increase the stability and yields as well as additional residues forming ionic bridges and increasing the heterodimerization yields (EP 1870459A1).

Example 4—Simultaneous Binding of Anti-BCMA/Anti-CD3 T Cell Bispecific Antibodies to BCMA and CD3 (Surface Plasmon Resonance)

The binding properties to BCMA and CD3 of bispecific anti-BCMA/anti-CD3 T cell bispecific antibodies generated in Example 3 are analyzed by surface plasmon resonance (SPR) technology using a Biacore® T100 instrument (Biacore AB) with HBS-EP as running buffer (0.01 M HEPES pH 7.4, 0.15 M NaCl, 3 mM EDTA, 0.005% Surfactant P20, Biacore). This system is well established for the study of molecule interactions. It allows a continuous real-time monitoring of ligand/analyte bindings and thus the determination of association rate constants (ka), dissociation rate constants (kd), and equilibrium constants (KD) in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to immobilized ligand on the surface the mass increases, in case of dissociation the mass decreases.

Capturing anti-His tag antibody is immobilized on the surface of a CM5 biosensorchip using amine-coupling chemistry. Flow cells are activated with a 1:1 mixture of 0.1 M N-hydroxysuccinimide and 0.1 M 3-(N,N-dimethylamino)propyl-N-ethylcarbodiimide at a flow rate of 5 µl/min anti-human IgG antibody is injected in sodium acetate, pH 5.0 at 10 µg/ml, which resulted in a surface density of approximately 12000 resonance units (RU). A reference control flow cell is treated in the same way but with vehicle buffers only instead of the capturing antibody. Surfaces are blocked with an injection of 1 M ethanolamine/HCl pH 8.5. The anti-BCMA/anti-CD3 T cell bispecific antibodies are diluted in HBS-P and injected at a flow rate of 5 µl/min. The contact time (association phase) is 1 min for the antibodies at a concentration between 1 and 100 nM for the BCMA-ECD binding and 1 and 200 nM for the CD3 interaction. BCMA-ECD is injected at increasing concentrations of 3.125, 6.25, 12.5, 25, 50 and 100 nM, CD3 at concentrations of 0.21, 0.62, 1.85, 5.6, 16.7, 50, 100 and 200 nM. The contact time (association phase) is 3 min, the dissociation time (washing with running buffer) 5 min for both molecules at a flowrate of 30 µl/min. All interactions are performed at 25° C. (standard temperature). The regeneration solution of 3 M Magnesium chloride is injected for 60 s at 5 µl/min flow to remove any non-covalently bound protein after each binding cycle. Signals are detected at a rate of one signal per second. Samples are injected at increasing concentrations. SPR graphs showing the rate of signal (i.e. resonance unit) plotted against contact time are determined.

Example 5—Binding of Anti-BCMA/Anti-CD3 T Cell Bispecific Antibodies to BCMA on MM Cells or CD3 on T Cells (Flow Cytometry)

Anti-BCMA/anti-CD3 T cell bispecific antibodies generated in Example 3 are also analyzed by flow cytometry for their binding properties to human BCMA expressed on NCI-H929 multiple myeloma cells or human CD3 expressed on human leukemic T cells Jurkat (ATCC). Briefly, cultured cells are harvested, counted and cell viability is evaluated using the Trypan Blue exclusion method. Viable cells are then adjusted to $2\times10^6$ cells per ml in PBS containing 0.1% BSA. 90 µl of this cell suspension are further aliquoted per well into a round-bottom 96-well plate. 10 µl of the T cell bispecific antibody or corresponding IgG control are added to the cell-containing wells to obtain final concentrations of 0.1 pM to 200 nM. Anti-BCMA/anti-CD3 T cell bispecific antibodies and control IgG are used at the same molarity. After incubation for 30 min at 4° C., cells are centrifuged (5 min, 350×g), washed with 150 µl/well BSA-containing FACS Stain Buffer (BD Biosciences), resuspended and incubated for an additional 30 min at 4° C. with 12 µl/well fluorochrome-conjugated anti-His antibody (Lucerna) for detection of the T cell bispecific antibody. Cells are then washed by addition of 120 µl/well FACS Stain Buffer and centrifugation at 350×g for 5 min. A second washing step is performed with 150 µl/well FACS Stain Buffer. The samples are resuspended in 200 µl/well FACS Stain Buffer, acquired and analyzed using an LSR II flow cytometer with FACSDiva® software (BD Biosciences). Binding of the anti-BCMA/anti-CD3 T cell bispecific antibodies to MM cells and T cells are evaluated and the mean fluorescence intensity is determined gated on either BCMA-expressing NCI-H929 MM cells or CD3-expressing Jurkat T cells and plotted in histograms or dot plots.

Example 6—Activation of T Cells Upon Engagement of Anti-BCMA/Anti-CD3 T Cell Bispecific Antibodies (Flow Cytometry)

Anti-BCMA/anti-CD3 T cell bispecific antibodies generated in Example 3 are also analyzed by flow cytometry for their potential to induce T cell activation by evaluating the surface expression of the early activation marker CD69, or the late activation marker CD25 on $CD4^+$ and $CD8^+$ T cells in the presence or absence of human BCMA-expressing MM cells. Briefly, BCMA-expressing NCI-H929 MM cells are harvested with Cell Dissociation buffer, counted and cell viability is verified using Trypan Blue. Viable MM cells are adjusted to $0.2 \times 10^6$ cells/mL in complete RPMI-1640 medium, 100 μl of this cell suspension per well is pipetted into a round-bottom 96-well plate. 50 μl of the T cell bispecific constructs are added to the MM cells-containing wells to obtain a final concentration of 1 nM. The 96-well plate is set aside and kept at 37° C., 5% $CO_2$ until further manipulations.

PBMC are isolated from fresh blood using density gradient centrifugation using Cell Preparation Tubes with Sodium citrate (Vacutainer CPT tubes, BD Biosciences). Total human T cells are then isolated using the Pan T Cell Isolation Kit II (Miltenyi Biotec), according to the manufacturer's instructions. Human total T cells (effector) are then adjusted to $2 \times 10^6$ cells per ml in complete RPMI-1640 medium. 50 μl of this cell suspension is added per well in the assay plate containing already BCMA-expressing MM cells to obtain a final E:T ratio of 5:1. To test whether the T cell bispecific constructs are able to activate T cells only in the presence of BCMA-expressing MM tumor target cells, wells containing final concentration(s) in the range of 0.1 pM to 200 nM of the respective bispecific molecules with effector cells but without MM tumor target cells are also included. After incubation for five days at 37° C., 5% $CO_2$, cells are pelleted down by centrifugation (5 min, 350×g) and washed twice with 150 μl/well of FACS Stain Buffer (BD Biosciences). Surface staining of the effector cells with selected fluorochrome-conjugated antibodies against human CD4, CD8, CD69 or CD25 (BD Biosciences) is performed at 4° C. for 30 min, protected from light, in FACS Stain Buffer (BD Biosciences) according to the manufacturer's protocol. Cells are washed twice with 150 μl/well FACS Stain Buffer, resuspended in 200 μl/well FACS Stain Buffer, and acquired and analyzed using a LSRII flow cytometer complemented with FACSDiva® software (BD Biosciences). The expression of CD69 and CD25 activation markers are determined by measuring the mean fluorescence intensity gated on $CD4^+$ and $CD8^+$ T cell populations as represented in histograms or dot plots.

Example 7—Proliferation of T Cells Upon Engagement of Anti-BCMA/Anti-CD3 T Cell Bispecific Antibodies (CFSE Dilution)

Anti-BCMA/anti-CD3 T cell bispecific antibodies generated in Example 3 are also analyzed by flow cytometry for their potential to induce proliferation of $CD8^+$ or $CD4^+$ T cells in the presence or absence of human BCMA-expressing MM cells. Briefly, BCMA-expressing NCI-H929 MM cells are harvested with Cell Dissociation buffer, counted and looked for viability using Trypan Blue. Viable MM cells are adjusted to $0.2 \times 10^6$ cells per ml in complete RPMI medium, 100 μl of this cell suspension are pipetted per well into a round-bottom 96-well plate. 50 μl of the T cell bispecific constructs are added to the MM cell-containing wells to obtain final concentration(s) in the range of 0.1 pM to 200 nM. The well plate is set aside and kept at 37° C., 5% $CO_2$.

PBMC are isolated from fresh blood using density gradient centrifugation using Cell Preparation Tubes with Sodium citrate (Vacutainer CPT tubes, BD Biosciences). Total human T cells are then isolated using the Pan T Cell Isolation Kit II (Miltenyi Biotec), according to the manufacturer's instructions. The total T cells are then adjusted to 1 million cells per ml in pre-warm RPMI without serum (37° C.) and stained with 1 μM CFSE at room temperature for 6 min, protected from light. The staining volume is then doubled by addition of RPMI-1640 medium supplemented with 10% FCS and 1% GlutaMax to stop CFSE staining. After incubation at room temperature for further 20 min, the cells are washed three times with pre-warmed serum-containing medium to remove remaining CFSE. CFSE-stained total T cells (effector) are then adjusted to $2 \times 10^6$ cells/mL in complete RPMI-1640 medium. 50 μl of this cell suspension is added per well in the assay plate already containing BCMA-expressing NCI-H929 MM cells to obtain a final E:T ratio of 5:1. To test whether the T cell bispecific constructs are able to activate T cells only in the presence of BCMA-expressing MM tumor target cells, wells containing 1 nM of the T cell bispecific antibodies with effector cells but without MM tumor target cells are also included. After incubation for five days at 37° C., 5% $CO_2$, cells are pelleted down by centrifugation (5 min, 350×g) and washed twice with 150 μl/well of FACS Stain Buffer (BD Biosciences). Surface staining of the effector cells with selected fluorochrome-conjugated antibodies against human CD4, CD8 or CD25 (BD) is performed at 4° C. for 30 min, protected from light, in FACS Stain Buffer according to the manufacturer's protocol. Cells are washed twice with 150 μl/well FACS Stain Buffer, resuspended in 200 μl/well FACS Stain Buffer, and acquired and analyzed using a LSR II flow cytometer complemented with FACSDiva® software (BD). The percentage of non-proliferating cells is determined by gating on the far right undiluted CFSE peak in the group which the wells contain BCMA-expressing MM cells and CFSE-stained T cells but without the T cell bispecific antibodies, and compared that to other experimental groups (wells). The percentage of proliferating cells is measured by gating all the diluted CFSE peaks excluding the far right peak (if observable). The proliferation level of $CD4^+$ and $CD8^+$ T cells is determined by gating on that population first then to further look at the CFSE dilution peaks.

Example 8—Cytokine Production from Activated T Cells Upon Engagement of Anti-BCMA/Anti-CD3 T Cell Bispecific Antibodies Example 8A. Interferon-γ Production Anti-BCMA/anti-CD3 T cell bispecific antibodies generated in Example 3 are also analyzed for their potential to induce interferon-γ (IFN-γ) production by the T cells in the presence or absence of human BCMA-expressing MM cells. Briefly, BCMA-expressing NCI-H929 MM cells are harvested with Cell Dissociation buffer, counted and looked for viability using Trypan Blue. Approximately 20,000 viable cells per well are plated in a round-bottom 96-well-plate and the respective antibody dilution is added to obtain final concentration(s) in the range of 0.1 pM to 200 nM. Anti-human BCMA and anti-CD3 IgGs adjusted to the same molarity are used as controls. Human total T effector cells are added to obtain a final E:T ratio of 5:1. After 20 h incubation at 37° C., 5% $CO_2$, human IFN-γ levels in the supernatant are measured by ELISA, according to the manufacturer's instructions (human IFN-γ ELISA Kit II, BD Biosciences). The levels of IFN-γ produced by T cells in the presence of anti-BCMA/anti-CD3 T cell bispecific antibody and BCMA-expressing MM cells is measured and plotted in histograms and compared to that produced by T cells in the presence of anti-BCMA/anti-CD3 T cell bispecific antibody and but without BCMA-expressing MM cells.

Example 8B. Cytokine Release Assay (CBA Analysis)

Anti-BCMA/anti-CD3 T cell bispecific antibodies generated in Example 3 are also analyzed for their potential to induce T-cell mediated cytokine production in the presence or absence of human BCMA-expressing MM cells. PBMC are isolated from fresh blood using density gradient centrifugation using Cell Preparation Tubes with Sodium citrate (Vacutainer CPT tubes, BD Biosciences) and a final cell concentration of 0.3 million cells/well are plated into a round-bottom 96-well plate. BCMA-expressing NCI-H929 MM cells are then added to obtain a final E:T-ratio of 10:1, as well as T cell bispecific constructs and IgG controls are added to obtain final concentration(s) in the range of 0.1 pM to 200 nM, for a 24 h incubation at 37° C., 5% $CO_2$. The next day, the cells are centrifuged for 5 min at 350×g and the supernatant is transferred into a new deep-well 96-well-plate for the further analysis. The CBA analysis is performed according to manufacturer's instructions for ISR II flow cytometer, using the Human Th1/Th2 Cytokine Kit II (BD Biosciences) including human IL-2, human IL-4, human IL-6, human IL-10, human TNF-α, and human IFN-γ. The levels of cytokines produced by T cells in the presence of anti-BCMA/anti-CD3 T cell bispecific antibody and BCMA-expressing MM cells is measured and plotted in histograms and compared to that produced by T cells in the presence of anti-BCMA/anti-CD3 T cell bispecific antibody and but without BCMA-expressing MM cells.

Example 9—Redirected T Cell Cytotoxicity of MM Cells Upon Cross-Linking of Anti-BCMA/Anti-CD3 T Cell Bispecific Antibodies to CD3 on T Cells and BCMA on MM Cells (LDH Release Assay)

Anti-BCMA/anti-CD3 T cell bispecific antibodies generated in Example 3 are also analyzed for their potential to induce T cell-mediated apoptosis in BCMA-expressing MM cells upon crosslinking of the construct via binding of the antigen binding moieties to BCMA on cells. Briefly, human BCMA-expressing NCI-H929 multiple myeloma target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 200 nM. For an appropriate comparison, all T cell bispecific constructs and controls are adjusted to the same molarity. Human total T cells (effector) are added into the wells to obtain a final E:T ratio of 5:1. When human PBMC are used as effector cells, a final E:T ratio of 10:1 is used. PHA-L (Sigma) is used as positive control for human T cell activation at a concentration of 1 μg/ml. Negative control groups are represented by effector or target cells only. For normalization, maximal lysis of the NCI-H929 MM target cells (=100%) is determined by incubation of the target cells with a final concentration of 1% Triton X-100, inducing cell death. Minimal lysis (=0%) is represented by target cells co-incubated with effector cells only, i.e. without any T cell bispecific antibody. After 20 h incubation at 37° C., 5% $CO_2$, LDH release from the apoptotic/necrotic MM target cells into the supernatant is then measured with the LDH detection kit (Roche Applied Science), following the manufacturer's instructions. The percentage of LDH release is plotted against the concentrations of anti-BCMA/anti-CD3 T cell bispecific antibodies in concentration-response curves. The $IC_{50}$ values are measured using Prism software (GraphPad) and determined as the T cell bispecific antibody concentration that results in 50% of LDH release.

Example 10—Comparison of T Cell Bispecifics Containing a Non-Ligand Blocking/Non-Competing Anti-BCMA Antibody vs. a Ligand-Blocking/Competing Anti-BCMA Antibody on the Killing Potency of BCMA-Expressing MM Cells In certain hematological malignancies such as multiple myeloma, the level of circulating BCMA-ligands APRIL and BAFF can be elevated (Moreaux et al. 2004; Blood 103(8): 3148-3157). Thus, the inventors recognize that high levels of ligands in the serum may interfere with the binding of anti-BCMA antibodies to BCMA on the tumor cells. In comparison to healthy donors, the levels of circulating APRIL (the high affinity ligand to BCMA) in MM patient are ~100 ng/mL vs. ~10 ng/mL. For BAFF (the low affinity ligand to BCMA), the levels can fluctuate from 1-1000 ng/mL as compared to ~3 ng/mL in healthy donors. Close to the tumor cells APRIL/BAFF concentrations may be well even higher than measured in the serum. In certain autoimmune diseases such as systemic lupus erythematosus, the levels of circulating APRIL are also elevated with ~85 ng/mL (Koyama et al. 2005; Ann Rheum Dis 64: 1065-1067).

Anti-BCMA/anti-CD3 T cell bispecific antibodies generated in Example 3 containing a non-ligand blocking/non-competing anti-BCMA antibody are also analyzed for their potential to induce T cell-mediated apoptosis in BCMA-expressing MM cells upon crosslinkage of the construct via binding of the antigen binding moieties to BCMA on cells in the presence of elevated concentrations (i.e. 100 ng/mL to 1000 ng/mL) of APRIL or BAFF in comparison to anti-BCMA/anti-CD3 T cell bispecific antibodies containing a ligand blocking/competing anti-BCMA antibody of the same format.

As shown in FIG. 1, the increasing concentrations (i.e. 10, 100, 1000 ng/mL) of soluble APRIL or BAFF representative of the levels found in the blood and bone marrow of multiple myeloma patients do not alter the binding of a non-ligand blocking/non-competing anti-BCMA antibody to plate-bound-BCMA (continuous line). In contrast, the high concentrations of soluble APRIL or BAFF representative of the levels (i.e. 100 ng/mL to 1000 ng/mL) found in the blood and bone marrow of multiple myeloma patients decrease the binding of a ligand blocking/competing anti-BCMA antibody to plate-bound-BCMA (dotted line).

Figure 2:
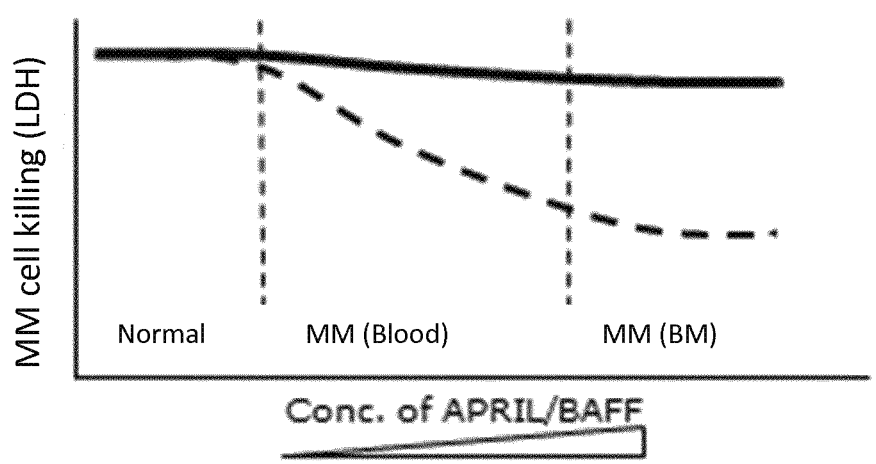
FIG. 2. Superior potency in redirected T cell cytotoxicity of BCMA-expressing MM cells mediated by a T cell bispecific antibody containing a non-ligand blocking/non-competing anti-BCMA antibody vs. a ligand-blocking/competing anti-BCMA antibody in a LDH release assay. In this graph, increasing concentrations (i.e. 10, 100, 1000 ng/mL) of soluble APRIL or BAFF representative of the levels found in the blood and bone marrow of multiple myeloma patients does not alter the killing potency of a T cell bispecific antibody containing a non-ligand blocking/non-competing anti-BCMA antibody specific to BCMA-expressing MM cells (continuous line). In contrast, the high concentrations (i.e. 100 ng/mL to 1000 ng/mL) of soluble APRIL or BAFF representative of the levels found in the blood and bone marrow of multiple myeloma patients decrease the killing potency of a T cell bispecific antibody containing a ligand blocking/competing anti-BCMA antibody specific to BCMA-expressing MM cells (dotted line). The concentration of T cell bispecifics with anti-BCMA antibody with different properties is preferably concentration(s) ranging from 0.1 pM to 200 nM as the levels of add-on circulating APRIL or BAFF range from 1 ng/mL (healthy normal) to 100 ng/mL (MM, blood) and beyond (MM, tumor in bone marrow).
Figure 3:
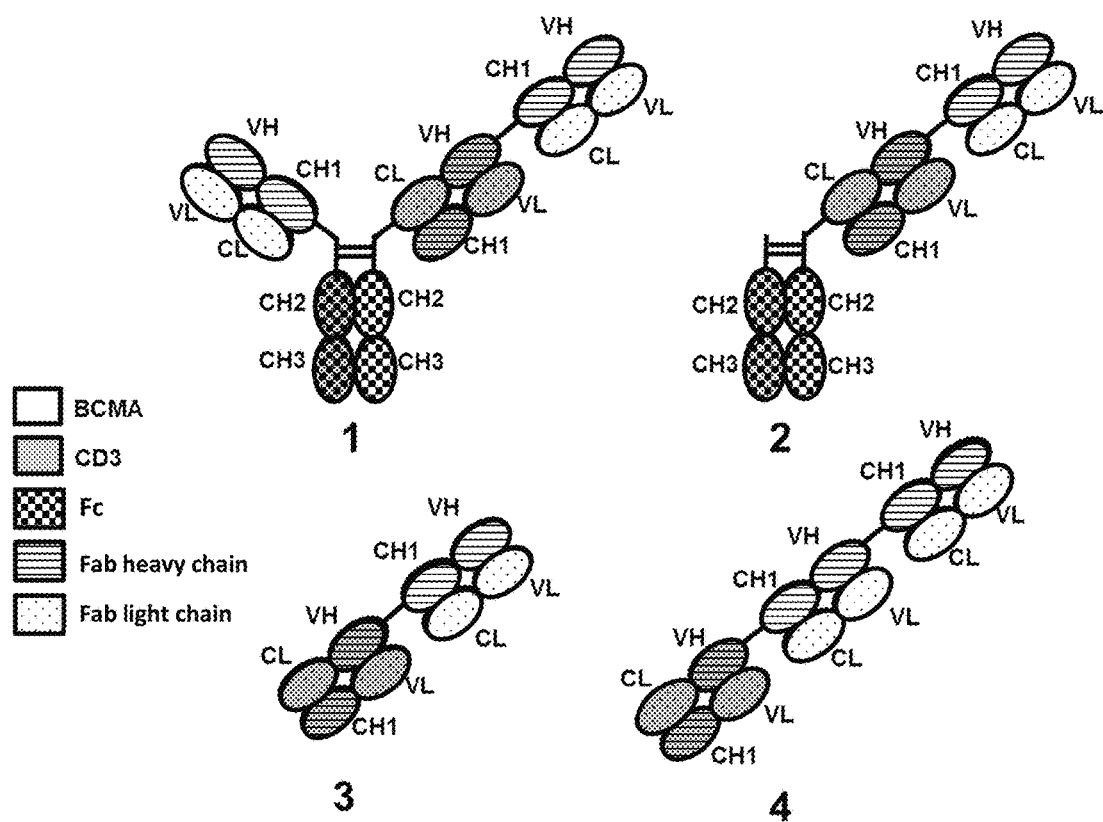
FIG. 3. Preferred bispecific antibodies comprising only the Fab fragments (specific to CD3 and BCMA) and the Fc part as specified: (1) Fab BCMA-Fc-Fab CD3-Fab BCMA; (2) Fc-Fab CD3-Fab BCMA; (3) Fab CD3-Fab BCMA; (4) Fab CD3-Fab BCMA-Fab BCMA. Preferably, the Fabs CD3 include a CH1-CL crossover to reduce LC mispairing and side-products. Fab CD3 and Fab BCMA are linked to each other with flexible linkers.

As shown in FIG. 2, the increasing concentrations (i.e. 10, 100, 1000 ng/mL) of soluble APRIL or BAFF representative of the levels found in the blood and bone marrow of multiple myeloma patients do not alter the killing potency of a T cell bispecific antibody containing a non-ligand blocking/non-competing anti-BCMA antibody specific to BCMA-expressing MM cells (continuous line). In contrast, the high concentrations (i.e. 100 ng/mL to 1000 ng/mL) of soluble APRIL or BAFF representative of the levels found in the blood and bone marrow of multiple myeloma patients decrease the killing potency of a T cell bispecific antibody containing a ligand blocking/competing anti-BCMA antibody specific to BCMA-expressing MM cells (dotted line).

Example 10A. Binding Properties of Anti-BCMA/Anti-CD3 T Cell Bispecific Antibodies to BCMA-Expressing MM Cells with a Non-Ligand Binding/Blocking, Non-Competing Anti-BCMA Antibody in the Presence of 10, 100, 1000 ng/mL of APRIL or BAFF (Flow Cytometry)

Anti-BCMA/anti-CD3 T cell bispecific antibodies with a non-ligand binding/blocking, non-competing anti-BCMA antibody generated in Example 3 are analyzed by flow cytometry for their binding properties to human BCMA expressed on NCI-H929 multiple myeloma cells in the presence of 10, 100 and 1000 ng/mL of APRIL or BAFF. Briefly, cultured cells are harvested, counted and cell viability is evaluated using the Trypan Blue exclusion method. Viable cells are then adjusted to $2 \times 10^6$ cells per ml in PBS containing 0.1% BSA. 90 µl of this cell suspension are further aliquoted per well into a round-bottom 96-well plate. 10 µl of the T cell bispecific antibody or corresponding IgG control are added to the cell-containing wells to obtain preferably final concentrations ranging from 0.1 pM to 200 nM. Anti-BCMA/anti-CD3 T cell bispecific antibodies and control IgG are used at the same molarity. After incubation for 30 min at 4° C., cells are centrifuged (5 min, 350×g), washed with 150 µl/well BSA-containing FACS Stain Buffer (BD Biosciences), resuspended and incubated for an additional 30 min at 4° C. with 12 µl/well fluorochrome-conjugated anti-His antibody (Lucerna) for detection of the T cell bispecific antibody. Cells are then washed by addition of 120 µl/well FACS Stain Buffer and centrifugation at 350×g for 5 min. A second washing step is performed with 150 µl/well FACS Stain Buffer. The samples are resuspended in 200 µl/well FACS Stain Buffer, acquired and analyzed using an LSR II flow cytometer with FACSDiva® software (BD Biosciences). Binding of the anti-BCMA/anti-CD3 T cell bispecific antibodies to MM cells and T cells are evaluated and the mean fluorescence intensity is determined gated on BCMA-expressing NCI-H929 MM cells and plotted in histograms or dot plots. The binding (e.g. MFI) of an anti-BCMA/anti-CD3 T cell bispecific antibodies with a non-ligand binding/blocking, non-competing anti-BCMA antibody to MM cells is then compared to that of an anti-BCMA/anti-CD3 T cell bispecific antibodies with a ligand binding/blocking, competing anti-BCMA antibody in the presence of 0, 10, 100, 1000 ng/mL of APRIL or BAFF.

Example 10B. Killing Properties of Anti-BCMA/Anti-CD3 T Cell Bispecific Antibodies with a Non-Ligand Binding/Blocking, Non-Competing Anti-BCMA Antibody in the Presence of 10, 100, 1000 Ng/mL of APRIL or BAFF: Redirected T Cell Cytotoxicity of BCMA-Expressing MM Cells (LDH Release Assay)

Anti-BCMA/anti-CD3 T cell bispecific antibodies with a non-ligand binding/blocking, non-competing anti-BCMA antibody generated in Example 3 are analyzed for their potential to induce T cell-mediated apoptosis in BCMA-expressing MM cells upon crosslinking of the construct via binding of the antigen binding moieties to BCMA on cells, in the presence or absence of increasing concentrations (i.e. 10, 100, 1000 ng/mL) of APRIL or BAFF. Briefly, human BCMA-expressing NCI-H929 multiple myeloma target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the T cell bispecific antibody is added preferably for concentration(s) in the range of 0.1 pM to 200 nM (in triplicates). For an appropriate comparison, all T cell bispecific antibodies and controls are adjusted to the same molarity. Increasing concentrations (i.e. 10, 100, 1000 ng/mL) of soluble human recombinant APRIL or BAFF are added to the cell cultures. Wells without addition of APRIL or BAFF are also included in the plate as controls. Human total T cells (effector) are then added into the wells to obtain a final E:T ratio of 5:1. When human PBMC are used as effector cells, a final E:T ratio of 10:1 is used. PHA-L (Sigma) is used as positive control for human T cell activation at a concentration of 1 µg/ml. Negative control groups are represented by effector or target cells only. For normalization, maximal lysis of the NCI-H929 MM target cells (=100%) is determined by incubation of the target cells with a final concentration of 1% Triton X-100, inducing cell death. Minimal lysis (=0%) is represented by target cells co-incubated with effector cells only, i.e. without any construct or antibody. After 20 h incubation at 37° C., 5% $CO_2$, LDH release from the apoptotic/necrotic MM target cells into the supernatant is then measured with the LDH detection kit (Roche Applied Science), following the manufacturer's instructions. The percentage of LDH release is plotted against the concentrations of APRIL or BAFF in the presence of concentration(s) of anti-BCMA/anti-CD3 T cell bispecific antibodies preferably in the concentration range of 0.1 pM to 200 nM in concentration-response curves. The $IC_{50}$ values are then measured using Prism software (GraphPad). The $IC_{50}$ values of an anti-BCMA/anti-CD3 T cell bispecific antibodies with a non-ligand binding/blocking, non-competing anti-BCMA antibody is then compared to that of an anti-BCMA/anti-CD3 T cell bispecific antibodies with a ligand binding/blocking, competing anti-BCMA antibody in the presence of 0, 10, 100, 1000 ng/mL of APRIL or BAFF.

Example 11—Evaluation of Therapeutic Efficacy of Anti-BCMA/Anti-CD3 T Cell Bispecific Antibody in the Vk*MYC Multiple Myeloma Mouse Model Murine cross-reactive anti-BCMA/anti-CD3 T cell bispecific antibodies are tested for their potential to prevent multiple myeloma in Vk*MYC multiple myeloma prone mice as described in Chesi, 2012 (Chesi et al. 2012; Blood 120: 376-385). Multiple myeloma is a hematological malignancy involving an uncontrolled expansion of plasma cells in the bone marrow. Since BCMA is strongly expressed on malignant plasma cells, we hypothesize that an anti-BCMA/anti-CD3 T cell bispecific will be efficacious for the treatment of multiple myeloma. The Vk*MYC multiple myeloma mouse model is highly representative of human myeloma and predictive of drug response used in the clinic; representing an excellent tool for testing the preclinical proof-of-concept of anti-BCMA/anti-CD3 T cell bispecific antibodies. Briefly, Vk*MYC mice obtained from an academic collaboration at Mayo Clinic Arizona are crossed with human CD3E transgenic (huCD3ε Tg) mice. T cells from huCD3ε Tg×Vk*MYC mice express both human CD3E and mouse CD3E on the cell surface and the mice are therefore responsive to anti-BCMA/anti-CD3 T cell bispecifics. Vk*MYC mice uniformly develop a monoclonal gammopathy initiated at around 30 weeks of age that progresses slowly over time associated with clinical signs representative of human myeloma such as anemia, osteoporosis and renal disease. Mice are periodically bled by tail grazing and blood is collected into Microtainer tubes (BD Biosciences), let coagulate at room temperature then spun for 10 min at 2,300 g. Sera are diluted 1:2 in normal saline buffer and analyzed on a QuickGel Chamber apparatus using pre-casted QuickGels (Helena Laboratories) according to manufacturer's instruction. Gamma/albumin ratio and serum fractions are measured by densitometric analysis.

For therapeutic studies, Vk*MYC mice are enrolled and randomized into different treatment groups (n=5-8/group): for example, 1) control IgGs; 2) anti-BCMA/anti-CD3 T cell bispecific antibodies; 500 Kg/kg/week or 10 Kg/mouse/week administered intravenously via the tail vein; 3) bortezomib 1 mg/kg/i.p. on days 1, 4, 8, 11 used as standard of care. Preferably, the dose(s) of anti-BCMA/anti-CD3 T cell bispecific antibodies could be multiple and range from 200 to 1000 Kg/kg/week. In each group, at least three aged (>1 year old) Vk*MYC mice with gamma/albumin ratio between 0.3-2.0, corresponding to a predominant M-spike between approximately 10-70 g/l as measured by densitometry. Serum protein electrophoresis (SPEP) is performed on day 0 and day 14 post treatment to measure treatment-mediated reduction in the M-spike as a marker of tumor response, as done in the clinic. In some therapeutic studies, transplanted Vk*MYC mice with an M-spike approximately 10-70 g/l and a bone marrow plasmacytosis of greater than 5% are enrolled and assigned to different treatment groups. The efficacy of anti-BCMA/anti-CD3 T cell bispecific antibodies to reduce M-spike is evaluated.

Example 12—Evaluation of Therapeutic Efficacy in the NZB/W Lupus Prone Mouse Model of Systemic Lupus Erythematosus Murine cross-reactive anti-BCMA/anti-CD3 T cell bispecific antibodies are tested for their potential to prevent systemic lupus erythematosus (SLE) in the NZB/W prone mice, a well-characterized model (Hass et al. 2010; J Immunol 184(9): 4789-4800). There is accumulating evidence suggesting that autoreactive plasma cells play an important role in SLE and depletion of the autoreactive plasma cells with an anti-BCMA/anti-CD3 T cell bispecific could be beneficial to SLE patients. Briefly, NZB and NZW mice are purchased from the Jackson Laboratory and crossed with huCD3ε Tg mice. NZB×huCD3ε Tg mice and NZW× huCD3ε Tg mice are then crossed with each other and female huCD3ε Tg×NZB/W F1 mice are selected for future studies. Mice are tested semiquantitatively for proteinuria with Albustix reagent strips (Siemens Healthcare Diagnostics Inc.) every other week, and scored on a scale from 0 to 4 according to protein concentration (from 0 to ≥20 g/l). huCD3ε Tg×NZB/W F1 female mice of 7-8 months of age are enrolled in therapeutic studies and randomized into different treatment groups (n=16/group): for example, 1) control IgGs; 2) anti-BCMA/anti-CD3 T cell bispecific antibodies; 500 µg/kg/week or 10 Kg/mouse/week administered intravenously via the tail vein; 3) anti-BAFF 20 mg/kg/week used as standard of care. Preferably, the dose(s) of anti-BCMA/anti-CD3 T cell bispecific antibodies could be multiple and range from 200 to 1000 µg/kg/week. The baseline protein levels at the start of the therapeutic studies are between 30 and 300 mg/dL.

The clinical endpoints representative of SLE consist of proteinuria, kidney diseases and manifestations such as glomerulonephritis, glomerular cellularity and size increase, periodic acid-Schiff (PAS)-positive deposits, and appearance of autoantibodies in sera such as dsDNA, total IgA, IgG and IgM as measured by ELISA.

The invention claimed is:

1. A bispecific antibody, in the format Fab BCMA-Fc-Fab CD3-Fab BCMA, specifically binding to the two targets human CD3ε and human BCMA (B-cell maturation antigen), wherein said bispecific antibody comprises
   (a) a first Fab fragment of an antibody specifically binding to human BCMA (first Fab fragment of the anti-BCMA antibody);
   (b) a second Fab fragment of the antibody specifically binding to human BCMA (second Fab fragment of the anti-BCMA antibody);
   (c) an Fc part;
   (d) a Fab fragment of an antibody specifically binding to human CD3ε (Fab fragment of the anti-CD3ε antibody), wherein the variable domains VL and VH or the constant domains CL and CH1 of the Fab fragment of the anti-CD3ε antibody are replaced by each other; and,
   wherein the first Fab fragment of the anti-BCMA antibody is linked via its C-terminus to the N-terminus of the hinge region of the Fc part, the Fab fragment of the anti-CD3ε antibody is linked via its C-terminus to the N-terminus of the hinge region of the Fc part, and the second Fab fragment of the anti-BCMA antibody is chemically linked via its C-terminus to the N-terminus of the Fab fragment of the anti-CD3ε antibody.

2. A host cell comprising vectors comprising nucleic acid molecules encoding light chains and heavy chains of a bispecific antibody according to claim 1.

3. A pharmaceutical composition comprising a bispecific antibody according to claim 1 and a pharmaceutically acceptable excipient.

4. A method of treating multiple myeloma comprising administering the bispecific antibody according to claim 1 to a subject in need thereof.

5. The bispecific antibody according to claim 1, wherein the Fc part is an Fc variant of a wild-type human IgG1 Fc region and wherein the Fc variant comprises an amino acid substitution at position Pro329 with glycine or arginine and at least one further amino acid substitution at position L234A or L235A.

* * * * *

SEQUENCE LISTING

```
<160> NUMBER OF SEQ ID NOS: 96

<210> SEQ ID NO 1
<211> LENGTH: 14
<212> TYPE: PRT
<213> ORGANISM: Mus musculus

<400> SEQUENCE: 1

Gly Ser Ser Thr Gly Ala Val Thr Ser Gly Tyr Tyr Pro Asn
1               5                   10

<210> SEQ ID NO 2
<211> LENGTH: 7
<212> TYPE: PRT
<213> ORGANISM: Mus musculus

<400> SEQUENCE: 2

Gly Thr Lys Phe Leu Ala Pro
1               5

<210> SEQ ID NO 3
<211> LENGTH: 9
<212> TYPE: PRT
<213> ORGANISM: Mus musculus

<400> SEQUENCE: 3

Ala Leu Trp Tyr Ser Asn Arg Trp Val
1               5
```

<210> SEQ ID NO 4
<211> LENGTH: 10
<212> TYPE: PRT
<213> ORGANISM: Mus musculus

<400> SEQUENCE: 4

Gly Phe Thr Phe Asn Lys Tyr Ala Met Asn
1               5                   10

<210> SEQ ID NO 5
<211> LENGTH: 19
<212> TYPE: PRT
<213> ORGANISM: Mus musculus

<400> SEQUENCE: 5

Arg Ile Arg Ser Lys Tyr Asn Asn Tyr Ala Thr Tyr Tyr Ala Asp Ser
1               5                   10                  15

Val Lys Asp

<210> SEQ ID NO 6
<211> LENGTH: 14
<212> TYPE: PRT
<213> ORGANISM: Mus musculus

<400> SEQUENCE: 6

His Gly Asn Phe Gly Asn Ser Tyr Ile Ser Tyr Trp Ala Tyr
1               5                   10

<210> SEQ ID NO 7
<211> LENGTH: 109
<212> TYPE: PRT
<213> ORGANISM: Mus musculus

<400> SEQUENCE: 7

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
                20                  25                  30

Tyr Tyr Pro Asn Trp Val Gln Gln Lys Pro Gly Gln Ala Pro Arg Gly
                35                  40                  45

Leu Ile Gly Gly Thr Lys Phe Leu Ala Pro Gly Thr Pro Ala Arg Phe
            50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
                100                 105

<210> SEQ ID NO 8
<211> LENGTH: 125
<212> TYPE: PRT
<213> ORGANISM: Mus musculus

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
    35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 9
<211> LENGTH: 105
<212> TYPE: PRT
<213> ORGANISM: Mus musculus

<400> SEQUENCE: 9

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 10
<211> LENGTH: 103
<212> TYPE: PRT
<213> ORGANISM: Mus musculus

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 11
<211> LENGTH: 39

```
<212> TYPE: DNA
<213> ORGANISM: Artificial Sequence
<220> FEATURE:
<223> OTHER INFORMATION: unassigned DNA primer

<400> SEQUENCE: 11
aagcttggat ccatgttgca gatggctggg cagtgctcc                              39

<210> SEQ ID NO 12
<211> LENGTH: 49
<212> TYPE: DNA
<213> ORGANISM: Artificial Sequence
<220> FEATURE:
<223> OTHER INFORMATION: unassigned DNA primer

<400> SEQUENCE: 12
gaattcgcgg ccgctcatcc tttcactgaa ttggtcacac ttgcattac                   49

<210> SEQ ID NO 13
<211> LENGTH: 42
<212> TYPE: DNA
<213> ORGANISM: Artificial Sequence
<220> FEATURE:
<223> OTHER INFORMATION: unassigned DNA primer

<400> SEQUENCE: 13
acgttagatc tccactcagt cctgcatctt gttccagtta ac                          42

<210> SEQ ID NO 14
<211> LENGTH: 33
<212> TYPE: DNA
<213> ORGANISM: Artificial Sequence
<220> FEATURE:
<223> OTHER INFORMATION: unassigned DNA primer

<400> SEQUENCE: 14
aacgttgcgg ccgctagttt cacaaacccc agg                                    33

<210> SEQ ID NO 15
<211> LENGTH: 45
<212> TYPE: DNA
<213> ORGANISM: Artificial Sequence
<220> FEATURE:
<223> OTHER INFORMATION: unassigned DNA primer

<400> SEQUENCE: 15
gaattcaagc ttgccaccat gttgcagatg gctgggcagt gctcc                       45

<210> SEQ ID NO 16
<211> LENGTH: 48
<212> TYPE: DNA
<213> ORGANISM: Artificial Sequence
<220> FEATURE:
<223> OTHER INFORMATION: unassigned DNA primer

<400> SEQUENCE: 16
gaattctcta gattacctag cagaaattga tttctctatc tccgtagc                    48

<210> SEQ ID NO 17
<211> LENGTH: 118
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Val Arg Gly Ala Phe Asp Tyr Trp Gly Gln Gly Thr
            100                 105                 110

Leu Val Thr Val Ser Ser
        115
```

<210> SEQ ID NO 18
<211> LENGTH: 119
<212> TYPE: PRT
<213> ORGANISM: Homo sapiens

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Pro Tyr Phe Ala Pro Phe Asp Tyr Trp Gly Gln Gly
            100                 105                 110

Thr Leu Val Thr Val Ser Ser
        115
```

<210> SEQ ID NO 19
<211> LENGTH: 116
<212> TYPE: PRT
<213> ORGANISM: Homo sapiens

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Val Leu Gly Trp Phe Asp Tyr Trp Gly Gln Gly Thr Leu Val
            100                 105                 110

Thr Val Ser Ser
        115

<210> SEQ ID NO 20
<211> LENGTH: 116
<212> TYPE: PRT
<213> ORGANISM: Homo sapiens

<400> SEQUENCE: 20

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 21
<211> LENGTH: 118
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ser Phe Gly Gly Gly Phe Asp Tyr Trp Gly Gln Gly Thr
            100                 105                 110

Leu Val Thr Val Ser Ser
        115

<210> SEQ ID NO 22
<211> LENGTH: 117
<212> TYPE: PRT
<213> ORGANISM: Homo sapiens

<400> SEQUENCE: 22

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Ser Gly Tyr Phe Asp Tyr Trp Gly Gln Gly Thr Leu
            100                 105                 110

Val Thr Val Ser Ser
            115

<210> SEQ ID NO 23
<211> LENGTH: 117
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ser Ser Gly Tyr Phe Asp Tyr Trp Gly Gln Gly Thr Leu
            100                 105                 110

Val Thr Val Ser Ser
            115

<210> SEQ ID NO 24
<211> LENGTH: 118
<212> TYPE: PRT
<213> ORGANISM: Homo sapiens

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Phe Trp Gly Ser Leu Val Tyr Trp Gly Gln Gly Thr
            100                 105                 110

Leu Val Thr Val Ser Ser
        115

<210> SEQ ID NO 25
<211> LENGTH: 117
<212> TYPE: PRT
<213> ORGANISM: Homo sapiens

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Asn Phe Gly Tyr Phe Asp Tyr Trp Gly Gln Gly Thr Leu
            100                 105                 110

Val Thr Val Ser Ser
        115

<210> SEQ ID NO 26
<211> LENGTH: 121
<212> TYPE: PRT
<213> ORGANISM: Homo sapiens

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Tyr Ser Ala Ser Gly Gly Phe Asp Tyr Trp Gly
            100                 105                 110

Gln Gly Thr Leu Val Thr Val Ser Ser
        115                 120

<210> SEQ ID NO 27
<211> LENGTH: 109
<212> TYPE: PRT
<213> ORGANISM: Homo sapiens

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Arg Val Thr Phe Gly Gln Gly Thr Lys Val Glu Ile Lys
            100                 105

<210> SEQ ID NO 28
<211> LENGTH: 109
<212> TYPE: PRT
<213> ORGANISM: Homo sapiens

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Pro Pro
                85                  90                  95

Leu Tyr Thr Phe Gly Gln Gly Thr Lys Val Glu Ile Lys
            100                 105

<210> SEQ ID NO 29
<211> LENGTH: 109
<212> TYPE: PRT
<213> ORGANISM: Homo sapiens

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys

<210> SEQ ID NO 30
<211> LENGTH: 111
<212> TYPE: PRT
<213> ORGANISM: Homo sapiens

<400> SEQUENCE: 30

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Met Gln Ile Pro Thr Phe Gly Gln Gly Thr Lys Val Glu Ile Lys
            100                 105                 110

<210> SEQ ID NO 31
<211> LENGTH: 109
<212> TYPE: PRT
<213> ORGANISM: Homo sapiens

<400> SEQUENCE: 31

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Tyr Pro Pro
                85                  90                  95
Ser Phe Thr Phe Gly Gln Gly Thr Lys Val Glu Ile Lys
            100                 105

<210> SEQ ID NO 32
<211> LENGTH: 109
<212> TYPE: PRT
<213> ORGANISM: Homo sapiens

<400> SEQUENCE: 32

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60

-continued

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Phe Asn Pro Pro
                85                  90                  95

Ser Ile Thr Phe Gly Gln Gly Thr Lys Val Glu Ile Lys
            100                 105

<210> SEQ ID NO 33
<211> LENGTH: 109
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Ala Phe Thr Phe Gly Gln Gly Thr Lys Val Glu Ile Lys
            100                 105

<210> SEQ ID NO 34
<211> LENGTH: 109
<212> TYPE: PRT
<213> ORGANISM: Homo sapiens

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Pro Pro
                85                  90                  95

Leu Phe Thr Phe Gly Gln Gly Thr Lys Val Glu Ile Lys
            100                 105

<210> SEQ ID NO 35
<211> LENGTH: 109
<212> TYPE: PRT
<213> ORGANISM: Mus musculus

<400> SEQUENCE: 35

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Phe Phe Thr Phe Gly Gln Gly Thr Lys Val Glu Ile Lys
            100                 105

<210> SEQ ID NO 36
<211> LENGTH: 113
<212> TYPE: PRT
<213> ORGANISM: Homo sapiens

<400> SEQUENCE: 36

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Thr Thr Pro Thr Tyr Thr Phe Gly Gln Gly Thr Lys Val Glu Ile
            100                 105                 110

Lys

<210> SEQ ID NO 37
<211> LENGTH: 5
<212> TYPE: PRT
<213> ORGANISM: Homo sapiens

<400> SEQUENCE: 37

Ser Tyr Ala Met Ser
1               5

<210> SEQ ID NO 38
<211> LENGTH: 5
<212> TYPE: PRT
<213> ORGANISM: Homo sapiens

<400> SEQUENCE: 38

Ser Tyr Ala Met Ser
1               5

<210> SEQ ID NO 39
<211> LENGTH: 5
<212> TYPE: PRT
<213> ORGANISM: Homo sapiens

<400> SEQUENCE: 39

Ser Tyr Ala Met Ser
1               5

<210> SEQ ID NO 40
<211> LENGTH: 5
<212> TYPE: PRT
<213> ORGANISM: Homo sapiens

<400> SEQUENCE: 40

Ser Tyr Trp Ile Gly
1               5

<210> SEQ ID NO 41
<211> LENGTH: 5
<212> TYPE: PRT
<213> ORGANISM: Homo sapiens

<400> SEQUENCE: 41

Ser Tyr Ala Met Ser
1               5

<210> SEQ ID NO 42
<211> LENGTH: 5
<212> TYPE: PRT
<213> ORGANISM: Homo sapiens

<400> SEQUENCE: 42

Ser Tyr Ala Met Ser
1               5

<210> SEQ ID NO 43
<211> LENGTH: 5
<212> TYPE: PRT
<213> ORGANISM: Homo sapiens

<400> SEQUENCE: 43

Ser Tyr Ala Met Ser
1               5

<210> SEQ ID NO 44
<211> LENGTH: 5
<212> TYPE: PRT
<213> ORGANISM: Homo sapiens

<400> SEQUENCE: 44

Ser Tyr Ala Met Ser
1               5

<210> SEQ ID NO 45
<211> LENGTH: 5
<212> TYPE: PRT
<213> ORGANISM: Homo sapiens

<400> SEQUENCE: 45

Ser Tyr Ala Met Ser
1               5

<210> SEQ ID NO 46
<211> LENGTH: 5
<212> TYPE: PRT
<213> ORGANISM: Homo sapiens

<400> SEQUENCE: 46

Ser Tyr Ala Met Ser
1               5

```
<210> SEQ ID NO 47
<211> LENGTH: 17
<212> TYPE: PRT
<213> ORGANISM: Homo sapiens

<400> SEQUENCE: 47

Ala Ile Ser Gly Ser Gly Gly Ser Thr Tyr Tyr Ala Asp Ser Val Lys
 1               5                  10                  15

Gly

<210> SEQ ID NO 48
<211> LENGTH: 17
<212> TYPE: PRT
<213> ORGANISM: Homo sapiens

<400> SEQUENCE: 48

Ala Ile Ser Gly Ser Gly Gly Ser Thr Tyr Tyr Ala Asp Ser Val Lys
 1               5                  10                  15

Gly

<210> SEQ ID NO 49
<211> LENGTH: 17
<212> TYPE: PRT
<213> ORGANISM: Homo sapiens

<400> SEQUENCE: 49

Ala Ile Ser Gly Ser Gly Gly Ser Thr Tyr Tyr Ala Asp Ser Val Lys
 1               5                  10                  15

Gly

<210> SEQ ID NO 50
<211> LENGTH: 17
<212> TYPE: PRT
<213> ORGANISM: Homo sapiens

<400> SEQUENCE: 50

Ile Ile Tyr Pro Gly Asp Ser Asp Thr Arg Tyr Ser Pro Ser Phe Gln
 1               5                  10                  15

Gly

<210> SEQ ID NO 51
<211> LENGTH: 17
<212> TYPE: PRT
<213> ORGANISM: Homo sapiens

<400> SEQUENCE: 51

Ala Ile Ser Gly Ser Gly Gly Ser Thr Tyr Tyr Ala Asp Ser Val Lys
 1               5                  10                  15

Gly

<210> SEQ ID NO 52
<211> LENGTH: 17
<212> TYPE: PRT
<213> ORGANISM: Homo sapiens

<400> SEQUENCE: 52

Ala Ile Ser Gly Ser Gly Gly Ser Thr Tyr Tyr Ala Asp Ser Val Lys
 1               5                  10                  15

Gly
```

<210> SEQ ID NO 53
<211> LENGTH: 17
<212> TYPE: PRT
<213> ORGANISM: Homo sapiens

<400> SEQUENCE: 53

Ala Ile Ser Gly Ser Gly Gly Ser Thr Tyr Tyr Ala Asp Ser Val Lys
1               5                   10                  15
Gly

<210> SEQ ID NO 54
<211> LENGTH: 17
<212> TYPE: PRT
<213> ORGANISM: Homo sapiens

<400> SEQUENCE: 54

Ala Ile Ser Gly Ser Gly Gly Ser Thr Tyr Tyr Ala Asp Ser Val Lys
1               5                   10                  15
Gly

<210> SEQ ID NO 55
<211> LENGTH: 17
<212> TYPE: PRT
<213> ORGANISM: Homo sapiens

<400> SEQUENCE: 55

Ala Ile Ser Gly Ser Gly Gly Ser Thr Tyr Tyr Ala Asp Ser Val Lys
1               5                   10                  15
Gly

<210> SEQ ID NO 56
<211> LENGTH: 17
<212> TYPE: PRT
<213> ORGANISM: Homo sapiens

<400> SEQUENCE: 56

Ala Ile Ser Gly Ser Gly Gly Ser Thr Tyr Tyr Ala Asp Ser Val Lys
1               5                   10                  15
Gly

<210> SEQ ID NO 57
<211> LENGTH: 9
<212> TYPE: PRT
<213> ORGANISM: Homo sapiens

<400> SEQUENCE: 57

Leu Ser Val Arg Gly Ala Phe Asp Tyr
1               5

<210> SEQ ID NO 58
<211> LENGTH: 10
<212> TYPE: PRT
<213> ORGANISM: Homo sapiens

<400> SEQUENCE: 58

Val Ala Pro Tyr Phe Ala Pro Phe Asp Tyr
1               5                   10

<210> SEQ ID NO 59
<211> LENGTH: 7
<212> TYPE: PRT
<213> ORGANISM: Homo sapiens

<400> SEQUENCE: 59

Val Leu Gly Trp Phe Asp Tyr
1               5

<210> SEQ ID NO 60
<211> LENGTH: 7
<212> TYPE: PRT
<213> ORGANISM: Homo sapiens

<400> SEQUENCE: 60

Asn Gly Tyr Leu Gly Asp Tyr
1               5

<210> SEQ ID NO 61
<211> LENGTH: 9
<212> TYPE: PRT
<213> ORGANISM: Homo sapiens

<400> SEQUENCE: 61

Val Ser Phe Gly Gly Gly Phe Asp Tyr
1               5

<210> SEQ ID NO 62
<211> LENGTH: 8
<212> TYPE: PRT
<213> ORGANISM: Homo sapiens

<400> SEQUENCE: 62

Val Arg Ser Gly Tyr Phe Asp Tyr
1               5

<210> SEQ ID NO 63
<211> LENGTH: 8
<212> TYPE: PRT
<213> ORGANISM: Homo sapiens

<400> SEQUENCE: 63

Val Ser Ser Gly Tyr Phe Asp Tyr
1               5

<210> SEQ ID NO 64
<211> LENGTH: 9
<212> TYPE: PRT
<213> ORGANISM: Homo sapiens

<400> SEQUENCE: 64

Val Ser Phe Trp Gly Ser Leu Val Tyr
1               5

<210> SEQ ID NO 65
<211> LENGTH: 8
<212> TYPE: PRT
<213> ORGANISM: Homo sapiens

<400> SEQUENCE: 65

Val Asn Phe Gly Tyr Phe Asp Tyr
1               5

<210> SEQ ID NO 66
<211> LENGTH: 12
<212> TYPE: PRT
<213> ORGANISM: Homo sapiens

<400> SEQUENCE: 66

Ser Tyr Gly Tyr Ser Ala Ser Gly Gly Phe Asp Tyr
1               5                   10

<210> SEQ ID NO 67
<211> LENGTH: 12
<212> TYPE: PRT
<213> ORGANISM: Homo sapiens

<400> SEQUENCE: 67

Arg Ala Ser Gln Ser Val Ser Ser Ser Tyr Leu Ala
1               5                   10

<210> SEQ ID NO 68
<211> LENGTH: 12
<212> TYPE: PRT
<213> ORGANISM: Homo sapiens

<400> SEQUENCE: 68

Arg Ala Ser Gln Ser Val Ser Ser Ser Tyr Leu Ala
1               5                   10

<210> SEQ ID NO 69
<211> LENGTH: 12
<212> TYPE: PRT
<213> ORGANISM: Homo sapiens

<400> SEQUENCE: 69

Arg Ala Ser Gln Ser Val Ser Ser Ser Tyr Leu Ala
1               5                   10

<210> SEQ ID NO 70
<211> LENGTH: 16
<212> TYPE: PRT
<213> ORGANISM: Homo sapiens

<400> SEQUENCE: 70

Arg Ser Ser Gln Ser Leu Leu His Ser Asn Gly Tyr Asn Tyr Leu Asp
1               5                   10                  15

<210> SEQ ID NO 71
<211> LENGTH: 12
<212> TYPE: PRT
<213> ORGANISM: Homo sapiens

<400> SEQUENCE: 71

Arg Ala Ser Gln Ser Val Ser Ser Ser Tyr Leu Ala
1               5                   10

<210> SEQ ID NO 72
<211> LENGTH: 12
<212> TYPE: PRT
<213> ORGANISM: Homo sapiens

<400> SEQUENCE: 72

Arg Ala Ser Gln Ser Val Ser Ser Ser Tyr Leu Ala
1               5                   10

<210> SEQ ID NO 73
<211> LENGTH: 12
<212> TYPE: PRT
<213> ORGANISM: Homo sapiens

<400> SEQUENCE: 73

Arg Ala Ser Gln Ser Val Ser Ser Ser Tyr Leu Ala

```
<210> SEQ ID NO 74
<211> LENGTH: 12
<212> TYPE: PRT
<213> ORGANISM: Homo sapiens

<400> SEQUENCE: 74

Arg Ala Ser Gln Ser Val Ser Ser Tyr Leu Ala
1               5                   10

<210> SEQ ID NO 75
<211> LENGTH: 12
<212> TYPE: PRT
<213> ORGANISM: Mus musculus

<400> SEQUENCE: 75

Arg Ala Ser Gln Ser Val Ser Ser Tyr Leu Ala
1               5                   10

<210> SEQ ID NO 76
<211> LENGTH: 16
<212> TYPE: PRT
<213> ORGANISM: Homo sapiens

<400> SEQUENCE: 76

Arg Ser Ser Gln Ser Leu Leu His Ser Asn Gly Tyr Asn Tyr Leu Asp
1               5                   10                  15

<210> SEQ ID NO 77
<211> LENGTH: 7
<212> TYPE: PRT
<213> ORGANISM: Homo sapiens

<400> SEQUENCE: 77

Gly Ala Ser Ser Arg Ala Thr
1               5

<210> SEQ ID NO 78
<211> LENGTH: 7
<212> TYPE: PRT
<213> ORGANISM: Homo sapiens

<400> SEQUENCE: 78

Gly Ala Ser Ser Arg Ala Thr
1               5

<210> SEQ ID NO 79
<211> LENGTH: 7
<212> TYPE: PRT
<213> ORGANISM: Homo sapiens

<400> SEQUENCE: 79

Gly Ala Ser Ser Arg Ala Thr
1               5

<210> SEQ ID NO 80
<211> LENGTH: 7
<212> TYPE: PRT
<213> ORGANISM: Mus musculus

<400> SEQUENCE: 80

Leu Gly Ser Asn Arg Ala Ser
1               5
```

```
<210> SEQ ID NO 81
<211> LENGTH: 7
<212> TYPE: PRT
<213> ORGANISM: Mus musculus

<400> SEQUENCE: 81

Gly Ala Ser Ser Arg Ala Thr
1               5

<210> SEQ ID NO 82
<211> LENGTH: 7
<212> TYPE: PRT
<213> ORGANISM: Mus musculus

<400> SEQUENCE: 82

Gly Ala Ser Ser Arg Ala Thr
1               5

<210> SEQ ID NO 83
<211> LENGTH: 7
<212> TYPE: PRT
<213> ORGANISM: Homo sapiens

<400> SEQUENCE: 83

Gly Ala Ser Ser Arg Ala Thr
1               5

<210> SEQ ID NO 84
<211> LENGTH: 7
<212> TYPE: PRT
<213> ORGANISM: Homo sapiens

<400> SEQUENCE: 84

Gly Ala Ser Ser Arg Ala Thr
1               5

<210> SEQ ID NO 85
<211> LENGTH: 7
<212> TYPE: PRT
<213> ORGANISM: Homo sapiens

<400> SEQUENCE: 85

Gly Ala Ser Ser Arg Ala Thr
1               5

<210> SEQ ID NO 86
<211> LENGTH: 7
<212> TYPE: PRT
<213> ORGANISM: Homo sapiens

<400> SEQUENCE: 86

Leu Gly Ser Asn Arg Ala Ser
1               5

<210> SEQ ID NO 87
<211> LENGTH: 10
<212> TYPE: PRT
<213> ORGANISM: Homo sapiens

<400> SEQUENCE: 87

Gln Gln Tyr Gly Tyr Pro Pro Arg Val Thr
1               5                   10

<210> SEQ ID NO 88
```

```
<211> LENGTH: 10
<212> TYPE: PRT
<213> ORGANISM: Homo sapiens

<400> SEQUENCE: 88

Gln Gln Tyr Gly Asn Pro Pro Leu Tyr Thr
1               5                   10

<210> SEQ ID NO 89
<211> LENGTH: 10
<212> TYPE: PRT
<213> ORGANISM: Homo sapiens

<400> SEQUENCE: 89

Gln Gln Tyr Gly Tyr Pro Pro Asp Phe Thr
1               5                   10

<210> SEQ ID NO 90
<211> LENGTH: 8
<212> TYPE: PRT
<213> ORGANISM: Homo sapiens

<400> SEQUENCE: 90

Met Gln Ala Met Gln Ile Pro Thr
1               5

<210> SEQ ID NO 91
<211> LENGTH: 10
<212> TYPE: PRT
<213> ORGANISM: Mus musculus

<400> SEQUENCE: 91

Gln Gln Tyr Gly Tyr Pro Pro Ser Phe Thr
1               5                   10

<210> SEQ ID NO 92
<211> LENGTH: 10
<212> TYPE: PRT
<213> ORGANISM: Homo sapiens

<400> SEQUENCE: 92

Gln Gln Tyr Phe Asn Pro Pro Ser Ile Thr
1               5                   10

<210> SEQ ID NO 93
<211> LENGTH: 10
<212> TYPE: PRT
<213> ORGANISM: Homo sapiens

<400> SEQUENCE: 93

Gln Gln Tyr Gly Tyr Pro Pro Ala Phe Thr
1               5                   10

<210> SEQ ID NO 94
<211> LENGTH: 10
<212> TYPE: PRT
<213> ORGANISM: Homo sapiens

<400> SEQUENCE: 94

Gln Gln Tyr Gly Asn Pro Pro Leu Phe Thr
1               5                   10

<210> SEQ ID NO 95
<211> LENGTH: 10
<212> TYPE: PRT
```

```
<213> ORGANISM: Homo sapiens

<400> SEQUENCE: 95

Gln Gln Tyr Gly Tyr Pro Pro Phe Phe Thr
1               5                   10

<210> SEQ ID NO 96
<211> LENGTH: 10
<212> TYPE: PRT
<213> ORGANISM: Homo sapiens

<400> SEQUENCE: 96

Met Gln Ala Leu Thr Thr Pro Thr Tyr Thr
1               5                   10
```